US012661104B2

(12) United States Patent
Han et al.

(10) Patent No.: US 12,661,104 B2
(45) Date of Patent: Jun. 23, 2026

(54) SURGICAL PADS AND SPACERS

(71) Applicant: Edwards Lifesciences Corporation, Irvine, CA (US)

(72) Inventors: Jingjia Han, Irvine, CA (US); Austin Engelbrecht, Trabuco Canyon, CA (US); Yin Fang, Irvine, CA (US); Hui-Chi Yang, Irvine, CA (US); Felino V. Cortez, Jr., Bowie, MD (US); Megan Cortez, Costa Mesa, CA (US); Luke Anthony Zanetti, Parkton, MD (US)

(73) Assignee: Edwards Lifesciences Corporation, Irvine, CA (US)

( * ) Notice: Subject to any disclaimer, the term of this patent is extended or adjusted under 35 U.S.C. 154(b) by 468 days.

(21) Appl. No.: 18/047,983

(22) Filed: Oct. 19, 2022

(65) Prior Publication Data

US 2023/0056175 A1 Feb. 23, 2023

Related U.S. Application Data

(63) Continuation of application No. PCT/US2021/028547, filed on Apr. 22, 2021.
(Continued)

(51) Int. Cl.
*A61B 17/04* (2006.01)
*A61B 17/00* (2006.01)
(52) U.S. Cl.
CPC .................... *A61B 17/0401* (2013.01); *A61B 2017/00004* (2013.01); *A61B 2017/0061* (2013.01);
(Continued)

(58) Field of Classification Search
CPC ...... A61B 17/0401; A61B 2017/00004; A61B 2017/0061; A61B 2017/0404;
(Continued)

(56) References Cited

U.S. PATENT DOCUMENTS 3,131,957 A 5/1964 Musto
3,752,516 A 8/1973 Mumma
(Continued)

FOREIGN PATENT DOCUMENTS

EP 0791330 A3 11/1997
EP 3505077 A1 7/2019
(Continued)

OTHER PUBLICATIONS

Alfieri, 0. el al., "The double-orifice technique in mitral valve repair: a +A198:A225simple solution for complex problems," (2001) J. Thome. Cardiovasc. Surg., 122(4):674-681.
(Continued)

*Primary Examiner* — Kathleen S Holwerda
*Assistant Examiner* — James R McGinnity
(74) *Attorney, Agent, or Firm* — Chang and Hale LLP

(57) ABSTRACT
A surgical pad can comprise a flexible pad portion configured to be positioned over an opening in a target tissue. A plurality of elongate ribs can be distributed across a surface of the flexible pad portion oriented away from the target tissue and can be coupled to the flexible pad portion. A surgical pad can comprise a central opening configured to be aligned with an opening in a target tissue, and a plurality of edge openings distributed around an outer edge portion. A method can comprise positioning a spacer between a target tissue and a surgical pad to adjust the tension of surgical cords secured to surgical pad. A method can comprise positioning a spacer between a surface of a surgical pad oriented away from a target tissue and portions of surgical cords secured over the surface of the surgical pad, to adjust the tension of the surgical cords.

17 Claims, 26 Drawing Sheets

Related U.S. Application Data

(60) Provisional application No. 63/148,246, filed on Feb. 11, 2021, provisional application No. 63/015,356, filed on Apr. 24, 2020.

(52) U.S. Cl.
CPC ................. *A61B 2017/0404* (2013.01); *A61B 2017/0409* (2013.01); *A61B 2017/0414* (2013.01); *A61B 2017/042* (2013.01); *A61B 2017/0464* (2013.01); *A61B 2017/0495* (2013.01)

(58) Field of Classification Search
CPC .... A61B 2017/0409; A61B 2017/0414; A61B 2017/042; A61B 2017/0464; A61B 2017/0495; A61F 2/0063–2/0095
See application file for complete search history.

(56) References Cited

U.S. PATENT DOCUMENTS

| | | | |
|---|---|---|---|
| 4,403,797 A | 9/1983 | Ragland, Jr. | |
| 4,662,376 A | 5/1987 | Belanger | |
| 4,807,625 A | 2/1989 | Singleton | |
| 5,144,961 A | 9/1992 | Chen et al. | |
| 5,147,316 A | 9/1992 | Castillenti | |
| 5,312,423 A | 5/1994 | Rosenbluth et al. | |
| 5,391,176 A | 2/1995 | de la Torre | |
| 5,405,352 A | 4/1995 | Weston | |
| 5,454,821 A | 10/1995 | Harm et al. | |
| 5,472,446 A | 12/1995 | de la Torre | |
| 5,507,754 A | 4/1996 | Green et al. | |
| 5,527,323 A | 6/1996 | Jervis et al. | |
| 5,554,184 A | 9/1996 | Machiraju | |
| 5,626,614 A | 5/1997 | Hart | |
| 5,643,293 A | 7/1997 | Kogasaka et al. | |
| 5,681,331 A | 10/1997 | de la Torre et al. | |
| 5,716,368 A | 2/1998 | de la Torre et al. | |
| 5,727,569 A | 3/1998 | Benetti et al. | |
| 5,728,109 A | 3/1998 | Schulze et al. | |
| 5,746,752 A | 5/1998 | Burkhart | |
| 5,769,862 A | 6/1998 | Kammerer et al. | |
| 5,797,928 A | 8/1998 | Kogasaka | |
| 5,824,065 A | 10/1998 | Gross | |
| 5,931,868 A | 8/1999 | Gross | |
| 5,957,936 A | 9/1999 | Yoon et al. | |
| 5,971,447 A | 10/1999 | Steck, III | |
| 6,010,531 A | 1/2000 | Donlon et al. | |
| 6,074,417 A | 6/2000 | Peredo | |
| 6,269,819 B1 | 8/2001 | Oz et al. | |
| 6,332,893 B1 | 12/2001 | Mortier et al. | |
| 6,562,051 B1 | 5/2003 | Bolduc et al. | |
| 6,626,930 B1 | 9/2003 | Allen et al. | |
| 6,629,534 B1 | 10/2003 | Goar et al. | |
| 6,752,810 B1 | 6/2004 | Gao et al. | |
| 6,840,246 B2 | 1/2005 | Downing | |
| 6,921,408 B2 | 7/2005 | Sauer | |
| 6,940,246 B2 | 9/2005 | Mochizuki et al. | |
| 6,978,176 B2 | 12/2005 | Lattouf | |
| 6,991,635 B2 | 1/2006 | Takamoto et al. | |
| 6,997,950 B2 | 2/2006 | Chawla | |
| 7,112,207 B2 | 9/2006 | Allen et al. | |
| 7,291,168 B2 | 11/2007 | Macoviak et al. | |
| 7,294,148 B2 | 11/2007 | McCarthy | |
| 7,309,086 B2 | 12/2007 | Carrier | |
| 7,316,706 B2 | 1/2008 | Bloom et al. | |
| 7,373,207 B2 | 5/2008 | Lattouf | |
| 7,431,692 B2 | 10/2008 | Zollinger et al. | |
| 7,513,908 B2 | 4/2009 | Lattouf | |
| 7,534,260 B2 | 5/2009 | Lattouf | |
| 7,608,091 B2 | 10/2009 | Goldfarb et al. | |
| 7,618,449 B2 | 11/2009 | Tremulis et al. | |
| 7,632,308 B2 | 12/2009 | Loulmet | |
| 7,635,386 B1 | 12/2009 | Gammle | |
| 7,666,196 B1 | 2/2010 | Miles | |
| 7,744,609 B2 | 6/2010 | Allen et al. | |
| 7,837,727 B2 | 11/2010 | Goetz et al. | |
| 7,871,368 B2 | 1/2011 | Zollinger et al. | |
| 7,871,433 B2 | 1/2011 | Lattouf | |
| 7,959,650 B2 | 6/2011 | Kaiser et al. | |
| 8,029,518 B2 | 10/2011 | Goldfarb et al. | |
| 8,029,565 B2 | 10/2011 | Lattouf | |
| 8,043,368 B2 | 10/2011 | Crabtree | |
| 8,147,542 B2 | 4/2012 | Maisano et al. | |
| 8,187,323 B2 | 5/2012 | Mortier et al. | |
| 8,226,711 B2 | 7/2012 | Mortier et al. | |
| 8,241,304 B2 | 8/2012 | Bachman | |
| 8,252,050 B2 | 8/2012 | Maisano et al. | |
| 8,292,884 B2 | 10/2012 | Levine et al. | |
| 8,303,622 B2 | 11/2012 | Alkhatib | |
| 8,333,788 B2 | 12/2012 | Maiorino | |
| 8,382,829 B1 | 2/2013 | Call et al. | |
| 8,439,969 B2 | 5/2013 | Gillinov et al. | |
| 8,454,656 B2 | 6/2013 | Tuval | |
| 8,465,500 B2 | 6/2013 | Speziali | |
| 8,475,525 B2 | 7/2013 | Maisano et al. | |
| 8,500,800 B2 | 8/2013 | Maisano et al. | |
| 8,608,758 B2 | 12/2013 | Singhatat et al. | |
| 8,663,278 B2 | 3/2014 | Mabuchi et al. | |
| 8,771,296 B2 | 7/2014 | Nobles et al. | |
| 8,828,053 B2 | 9/2014 | Sengun et al. | |
| 8,852,213 B2 | 10/2014 | Gammie et al. | |
| 8,888,791 B2 | 11/2014 | Jaramillo et al. | |
| 8,940,008 B2 | 1/2015 | Kunis | |
| 9,131,884 B2 | 9/2015 | Holmes et al. | |
| 9,192,287 B2 | 11/2015 | Saadat et al. | |
| 2002/0013571 A1 | 1/2002 | Goldfarb et al. | |
| 2003/0023254 A1 | 1/2003 | Chiu | |
| 2003/0094180 A1 | 5/2003 | Benetti | |
| 2003/0105519 A1 | 6/2003 | Fasol et al. | |
| 2003/0120264 A1 | 6/2003 | Lattouf | |
| 2003/0120341 A1 | 6/2003 | Shennib et al. | |
| 2004/0044365 A1 | 3/2004 | Bachman | |
| 2004/0093023 A1 | 5/2004 | Allen et al. | |
| 2004/0199183 A1 | 10/2004 | Oz et al. | |
| 2005/0004667 A1 | 1/2005 | Swinford et al. | |
| 2005/0019735 A1 | 1/2005 | Demas | |
| 2005/0075654 A1 | 4/2005 | Kelleher | |
| 2005/0119735 A1 | 6/2005 | Spence et al. | |
| 2005/0149067 A1 | 7/2005 | Takemoto et al. | |
| 2005/0149093 A1 | 7/2005 | Pokorney | |
| 2005/0154402 A1 | 7/2005 | Sauer et al. | |
| 2005/0216036 A1 | 9/2005 | Nakao | |
| 2005/0216077 A1 | 9/2005 | Mathis et al. | |
| 2005/0261710 A1 | 11/2005 | Sakamoto et al. | |
| 2005/0267493 A1 | 12/2005 | Schreck et al. | |
| 2006/0030866 A1 | 2/2006 | Schreck | |
| 2006/0100698 A1 | 5/2006 | Lattouf | |
| 2006/0111739 A1 | 5/2006 | Staufer et al. | |
| 2006/0167541 A1 | 7/2006 | Lattouf | |
| 2006/0189918 A1* | 8/2006 | Barker ............... A61B 17/0057 |
| | | | 604/15 |
| 2006/0190030 A1 | 8/2006 | To et al. | |
| 2006/0282088 A1 | 12/2006 | Ryan | |
| 2007/0001857 A1 | 1/2007 | Hartmann et al. | |
| 2007/0049952 A1 | 3/2007 | Weiss | |
| 2007/0055292 A1 | 3/2007 | Ortiz et al. | |
| 2007/0112422 A1 | 5/2007 | Dehdashtian | |
| 2007/0112425 A1 | 5/2007 | Schaller et al. | |
| 2007/0118151 A1 | 5/2007 | Davidson | |
| 2007/0118154 A1 | 5/2007 | Crabtree | |
| 2007/0149995 A1 | 6/2007 | Quinn et al. | |
| 2007/0185497 A1* | 8/2007 | Cauthen ............. A61B 17/0057 |
| | | | 623/17.11 |
| 2007/0197858 A1 | 8/2007 | Goldfarb et al. | |
| 2007/0213582 A1 | 9/2007 | Zollinger et al. | |
| 2007/0270793 A1 | 11/2007 | Lattouf | |
| 2008/0004597 A1 | 1/2008 | Lattouf et al. | |
| 2008/0009888 A1 | 1/2008 | Ewers et al. | |
| 2008/0065203 A1 | 3/2008 | Khalapyan | |
| 2008/0140093 A1 | 6/2008 | Stone et al. | |
| 2008/0167714 A1 | 7/2008 | St. Goar et al. | |
| 2008/0188893 A1 | 8/2008 | Selvitelli et al. | |
| 2008/0195126 A1 | 8/2008 | Solem | |

(56) References Cited

U.S. PATENT DOCUMENTS

| | | |
|---|---|---|
| 2008/0228223 A1 | 9/2008 | Alkhatib |
| 2008/0249504 A1 | 10/2008 | Lattouf et al. |
| 2008/0269781 A1 | 10/2008 | Funamura et al. |
| 2009/0005863 A1 | 1/2009 | Goetz et al. |
| 2009/0043153 A1 | 2/2009 | Zollinger et al. |
| 2009/0105729 A1 | 4/2009 | Zentgraf |
| 2009/0105751 A1 | 4/2009 | Zentgraf |
| 2009/0276038 A1 | 11/2009 | Tremulis et al. |
| 2010/0023056 A1 | 1/2010 | Johansson et al. |
| 2010/0023117 A1 | 1/2010 | Yoganathan et al. |
| 2010/0023118 A1 | 1/2010 | Medlock et al. |
| 2010/0042147 A1 | 2/2010 | Janovsky et al. |
| 2010/0174297 A1 | 7/2010 | Speziali |
| 2010/0179574 A1 | 7/2010 | Longoria et al. |
| 2010/0210899 A1 | 8/2010 | Schankereli |
| 2010/0298930 A1 | 11/2010 | Orlov |
| 2011/0015476 A1 | 1/2011 | Franco |
| 2011/0022083 A1 | 1/2011 | DiMatteo et al. |
| 2011/0022084 A1 | 1/2011 | Sengun et al. |
| 2011/0028995 A1 | 2/2011 | Miraki et al. |
| 2011/0029071 A1 | 2/2011 | Zlotnick et al. |
| 2011/0060407 A1 | 3/2011 | Ketal et al. |
| 2011/0106106 A1 | 5/2011 | Meier et al. |
| 2011/0144743 A1 | 6/2011 | Lattouf |
| 2011/0264208 A1 | 10/2011 | Duffy et al. |
| 2011/0270278 A1 | 11/2011 | Overes et al. |
| 2011/0288637 A1 | 11/2011 | De Marchena |
| 2011/0307055 A1 | 12/2011 | Goldfarb et al. |
| 2012/0004669 A1 | 1/2012 | Overes et al. |
| 2012/0143215 A1 | 6/2012 | Corrao et al. |
| 2012/0150223 A1 | 6/2012 | Manos et al. |
| 2012/0179184 A1 | 7/2012 | Orlov |
| 2012/0184971 A1 | 7/2012 | Zentgraf et al. |
| 2012/0203072 A1 | 8/2012 | Lattouf et al. |
| 2012/0226294 A1 | 9/2012 | Tuval |
| 2012/0226349 A1 | 9/2012 | Tuval et al. |
| 2013/0018459 A1 | 1/2013 | Maisano et al. |
| 2013/0035757 A1 | 2/2013 | Zentgraf et al. |
| 2013/0253574 A1* | 9/2013 | Catanese, III ......... A61B 17/42 |
| | | 606/201 |
| 2013/0253641 A1 | 9/2013 | Lattouf |
| 2013/0282059 A1 | 10/2013 | Ketai et al. |
| 2013/0345749 A1 | 12/2013 | Sullivan et al. |
| 2014/0031926 A1 | 1/2014 | Kudlik et al. |
| 2014/0039607 A1 | 2/2014 | Kovach |
| 2014/0067052 A1 | 3/2014 | Chau et al. |
| 2014/0100604 A1* | 4/2014 | Litvack .............. A61B 17/3423 |
| | | 606/213 |
| 2014/0114404 A1 | 4/2014 | Gammie et al. |
| 2014/0214152 A1 | 7/2014 | Bielefeld |
| 2014/0243968 A1 | 8/2014 | Padala |
| 2014/0364938 A1 | 12/2014 | Longoria et al. |
| 2015/0025553 A1* | 1/2015 | Del Nido .............. A61F 2/2487 |
| | | 606/151 |
| 2015/0032127 A1 | 1/2015 | Gammie et al. |
| 2015/0045879 A1 | 2/2015 | Longoria et al. |
| 2015/0209127 A1* | 7/2015 | Cohen .................. A61F 2/0077 |
| | | 606/151 |
| 2017/0273680 A1* | 9/2017 | Sengun ................ A61L 31/044 |
| 2019/0175346 A1 | 6/2019 | Schaffner et al. |
| 2020/0155315 A1 | 5/2020 | Zhang et al. |
| 2021/0212692 A1* | 7/2021 | Aramaki .......... A61B 17/07292 |
| 2021/0228194 A1* | 7/2021 | Mayberg ................ A61L 27/54 |
| 2022/0154370 A1* | 5/2022 | Han ..................... D01D 5/0084 |
| 2022/0313233 A1* | 10/2022 | Roche ............... A61B 17/0057 |

FOREIGN PATENT DOCUMENTS

| | | |
|---|---|---|
| JP | 2013517110 A | 5/2013 |
| WO | 2004037463 A1 | 5/2004 |
| WO | 2006127509 A2 | 11/2006 |
| WO | 2007100268 A2 | 9/2007 |
| WO | 2007119057 A1 | 10/2007 |
| WO | 2008013869 A2 | 1/2008 |
| WO | 2008124110 A3 | 12/2008 |
| WO | 2008143740 A3 | 2/2009 |
| WO | 2006078694 A3 | 4/2009 |
| WO | 2009081396 A2 | 7/2009 |
| WO | 2010070649 A1 | 6/2010 |
| WO | 2010105046 A1 | 9/2010 |
| WO | 2012137208 A1 | 10/2012 |
| WO | 2013003228 A1 | 1/2013 |
| WO | 2014093861 A1 | 6/2014 |
| WO | 2015020816 A1 | 2/2015 |
| WO | 2016192481 A1 | 12/2016 |

OTHER PUBLICATIONS

Barbero-Marcial, M. et al., "Transxiphoid Approach Without Median Sternotomy for the Repair of Atrial Septa! Defects," (1998) Ann. Thome. Surg., 65(3):771-774.

Braunberger, E. et al., "Very long-term results (more than 20 years) of valve repair with Carpentier's echniques in nonheumatic mitral valve insufficiency," (2001) Circulation, I 04:1-8-1-11.

Carpentier, Alain, "Cardiac valve surgery—the 'French coffection'," The Journal of Thoracic and Cardiovascular Surgery, vol. 86, No. 3, Sep. 1983, 15 pages.

David, T. E. et al., "Mitral valve repair by replacement of chordae tendineae with polytetrafluoroethylene sutures," (1991) J. Thorne. Cardiovasc. Surg., 101 (3 ):495-50.

David, T. E. et al., "Replacement of chordae tendineae with Gore-Tex sutures: a ten-year experience," (1996) J. Heart Valve Dis., 5(4 ):352-355.

Doty, D. B. et al., "Full-Spectrum Cardiac Surgery Through a Minimal Incision: Mini-Sternotomy (Lower Half) Technique," (1998) Ann. Thorne. Surg., 65(2):573-577.

Duran, C. M. G. et al., "Techniques for ensuring the correct length of new mitral chords," (2003) .I. Heart Valve Dis., 12(2):156-161.

Eishi, K. et al., "Long-term results of artificial chordae implantation in patients with mitral valve prolapse," (1997) J. Heal1 Valve Dis., 6(6):594-598.

Frater, R. W. M. ct al., "Chordal replacement in mitral valve repair," (1990) Circulation, 82(suppl. IV):IV-125-IV-130.

Frater, R. W. M., "Anatomical rules for the plastic repair of a diseased mitral valve," (1964) Thorax. 19:458-464.

Huber, C.H. et al., "Direct Access Valve Replacement (DAVR)—are we entering a new era in cardiac surgery?" (2006) European Journal ofCardio-thoracic Surgery, 29:380-385.

Hvass, U. et al., "Papillary Muscle Sling: A New Functional Approach to Mitra! Repair in Patients With Ischernic Left Ventricular Dysfunction and Functional Mitral Regurgitation," (2003) Ann. Thorne. Surg., 75:809-811.

Kasegawa, H. ct al., "Simple method for determining proper length of allificial chordae in mitral valve repair," (1994) Ann. Thome. Surg., 57(1 ):237-239.

Kobayashi, J. et al., "Ten-year experience of chordal replacement with expanded polytetrafluoroethylene in mitral valve repair," (2000) Circulation, J 02(19 Suppl 3):1ii-30-Jii-34.

Kunzelman, K. et al., "Replacement of mitral valve posterior chordae tenclincae with expanded polytetrafluorocthylonc suture: a finite element study," (1996) J. Card. Surg., 11(2):136-145.

Langer, F. et al., "RING plus STRING: Papillary muscle repositioning as an adjunctive repair technique for ischemic mitral regurgitation," (2007) J. Thorne. Cardiovasc. Surg., 133( I): 247-249.

Maisano, F. et al., "The double-orifice technique as a standardized approach to treat mitral regurgitation due to severe myxomatous disease: surgical technique." (2000) European Journal of Cardiothomcic Surgery, 17(3):201-205.

Merendino, K. A. et al., "The open con-ection of rheumatic mitral regurgitation and/or stenosis with special reference to regurgitation treated by posteromedial annuloplasty utilizing a pump-oxygenator," (1959) Annals of Surgery, 150(1 ):5-22.

Minatoya, K. et al., "Pathologic aspects of polytetrafluoroethylene sutures in human heart," (1996) Ann. Thorac. Surg., 61 (3 ):883-887.

(56) References Cited

OTHER PUBLICATIONS

Mohty, D. ct al., "Very long-term survival and durability of mitral valve repair for mitral valve prolapse," (2001) Circulation, 104:1-1-1-7.

*Neochord, Inc.* v. *University of Maryland, Bal tim ore,* Case No. JPR2016-00208, Decision on Institution of Inter Faries Review,37 CFR §42. I 08, Paper 6, Entered May 24, 2016, 28 pages.

*Neochord, Inc.* v. *University of Maryland, Baltimore,* Case No. IPR2016-00208, Declaration of Dr. Lishan Aklog, dated Nov. 17, 2015, 91 pages.

*Neochord, Inc.* v. *University of Maryland, Baltimore,* Case No. IPR2016-00208, Petition for inter ParlesReview of U.S. Pat. No. 7,635,386, dated Nov. 18, 2015, 65 pages.

Nigro, J. J. et al., "Neochordal repair of the posterior mitral leaflet," (2004) J. Thorne. Cardiovasc. Surg., 127 (2):440-447.

Phillips, M. R. et al., "Repair of anterior leaflet mitral valve prolapse: chordal replacement versus chordal shrntening," (2000) Ann. Thorac. Surg., 69(1 ):25-29.

Russo, M. J. ct al. "'Transapical Approach for Mitral Valve Repair during Insertion of a Left Ventricular Assist Device," Hindawi Publishing Corporation, The Scientific World Journal, vol. 2013, Article ID 925310, [ online], Retrieved from the internet: <URL: http://dx.doi.org/J 0.1155/2013/92531 O> Apr. 11, 2013, 4 pages.

Sarsam, M.A. I., "Simplified technique for determining the length of artificial clfordae in mitral valve repair," (2002) Ann. Thorac. Surg., 73(5): 1659-1660.

Savage, E. B. et al., Use of mitral valve repair: analysis of contemporary United States experience reported to the society of thoracic surgeons national cardiac database, .. (2003) Ann. Thorne. Surg., 75:820-825.

Speziali, G. et al., "Collection of Mitral Valve Regurgitation by Off-Pump, Transapical Placement of Artificial Chordae Tendinae, Results of the European TACT Trial," AATS 93rd Annual Meeting 2013, www.aats.org, 26 pages.

Suematsu, Y. et al., "Three-dimensional echo-guided beating heall surgery without cardiopulmonary bypass: Atrial septa! defect closure in a swine model," (2005) J. Thorne. Cardiovasc. Surg., 130: 1348-1357.

Von Oppell, U. 0. et al., "Chordal replacement for both minimally invasive and conventional mitral valve surgery using promcasurod Gore-Tex loops," (2000) Ann. Thorne. Surg., 70(6):2166-2168.

Zussa, C. et al., Artificial mitral valve chordae: experimental and clinical experience;• ( 1990) Ann. Thorne. Surg., 50 (3):367-373.

Zussa, C. et al., "Seven-year experience with chordal replacement with expanded polytetrafluoroethylene in floppymitral valve," (1994)1. Thorac. Cardiovasc. Surg., 108(1):37-41.

Zussa, C. et al., "Surgical technique for artificial mitral chordae implantation," ( 1991) Journal of Cardiac Surgery, 6 (4):432-438.

Zussa, C., "Artificial chordae," (1995) J. Heart Valve Dis., 4(2):S249-S256.

* cited by examiner

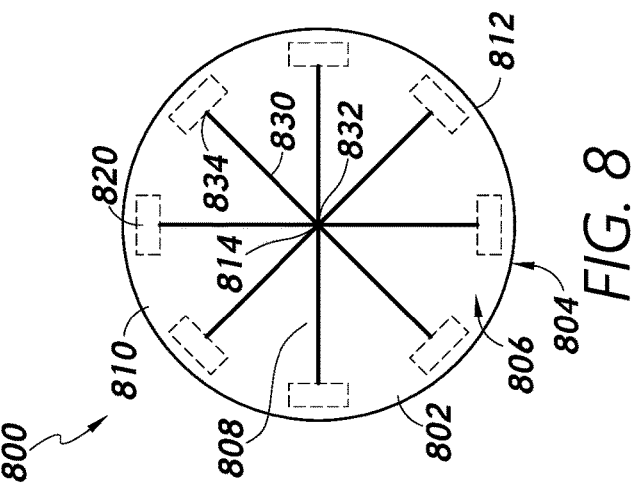
FIG. 8
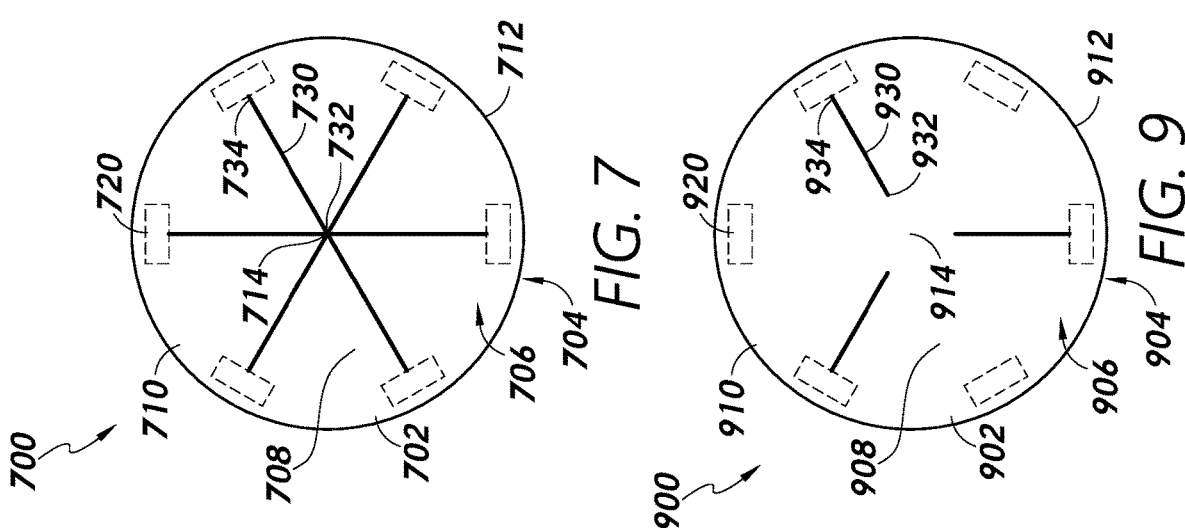
FIG. 7
FIG. 9
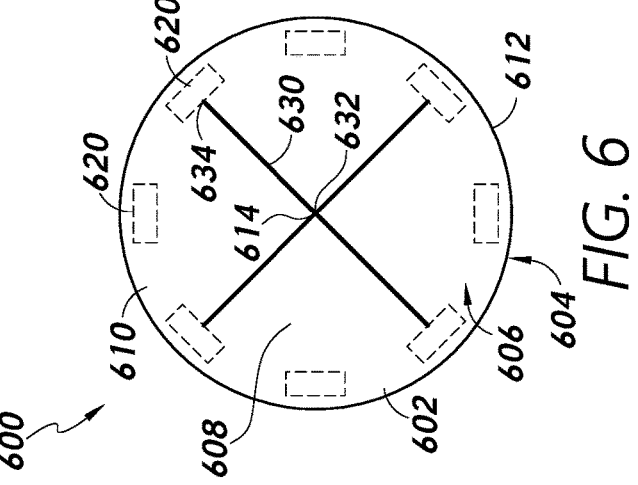
FIG. 6

*1100*

PROVIDE FLEXIBLE PAD PORTION COMPRISING FIRST SURFACE AND SECOND SURFACE, SECOND SURFACE COMPRISING PLURALITY OF ELONGATE RIBS ASSOCIATED THEREWITH       *1102*

POSITION FLEXIBLE PAD PORTION OVER OPENING IN TARGET TISSUE TO ORIENT FIRST SURFACE TOWARD TARGET TISSUE AND SECOND SURFACE AWAY FROM TARGET TISSUE       *1104*

THREAD EACH OF PLURALITY OF TETHERS EXTENDING FROM OPENING IN TARGET TISSUE THROUGH FLEXIBLE PAD PORTION AT CORRESPONDING DESIGNATED LOCATIONS AROUND OUTER EDGE PORTION OF SECOND SURFACE       *1106*

SECURE PLURALITY OF TETHERS TO FLEXIBLE PAD PORTION       *1108*

```
┌─────────────────────────────────────┐
│ PROVIDE SURGICAL PAD COMPRISING      │
│ CENTRAL OPENING IN CENTER PORTION    │──1802
│ AND PLURALITY OF OPENINGS POSITIONED │
│ AROUND OUTER EDGE PORTION            │
└─────────────────────────────────────┘
                  │
                  ▼
┌─────────────────────────────────────┐
│ POSITION SURGICAL PAD OVER TARGET    │
│ TISSUE, CENTRAL OPENING IN ALIGNMENT │──1804
│ WITH OPENING IN TARGET TISSUE        │
└─────────────────────────────────────┘
                  │
                  ▼
┌─────────────────────────────────────┐
│ PROVIDE PLURALITY OF ANCHOR CORDS,   │
│ EACH OF PLURALITY OF ANCHOR CORDS    │
│ COMPRISING PORTION EXTENDING THROUGH │──1806
│ CORRESPONDING EDGE OPENING AND       │
│ ANOTHER PORTION EMBEDDED WITHIN      │
│ TARGET TISSUE                        │
└─────────────────────────────────────┘
                  │
                  ▼
┌─────────────────────────────────────┐
│ TENSION PLURALITY OF ANCHOR CORDS    │
│ EXTENDING THROUGH PLURALITY OF EDGE  │──1808
│ OPENINGS TO REDUCE SIZE OF OPENING   │
└─────────────────────────────────────┘
```

*FIG. 18*

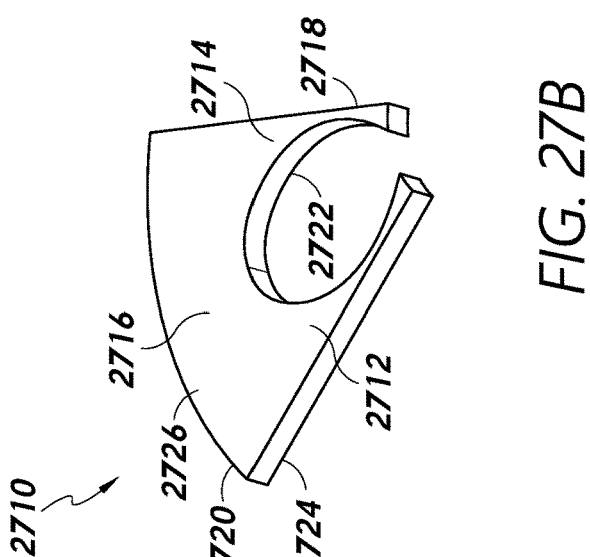
FIG. 27B
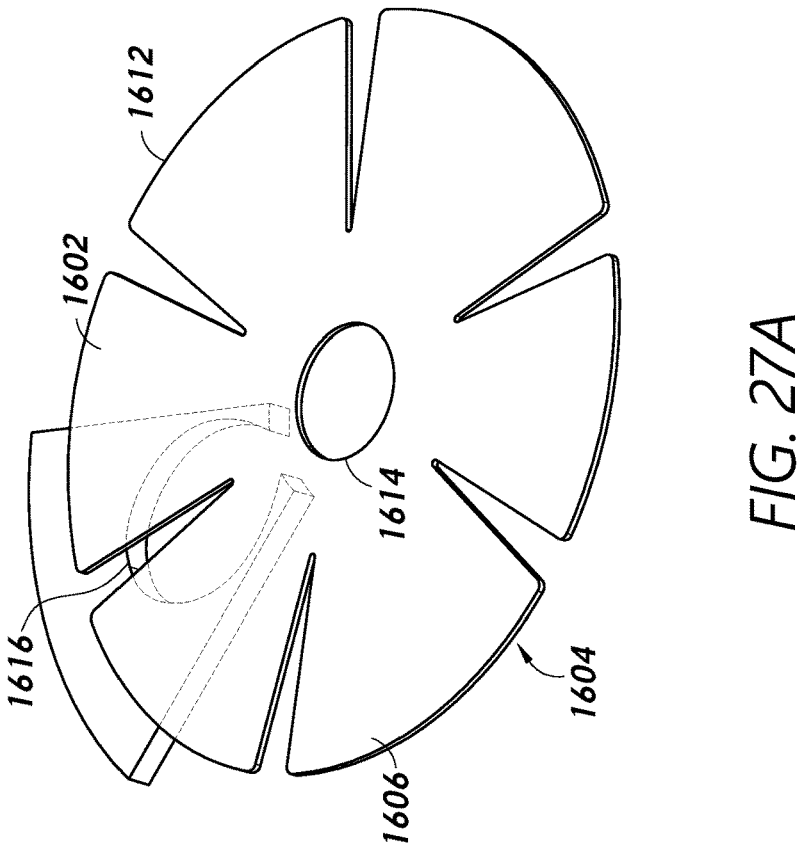
FIG. 27A

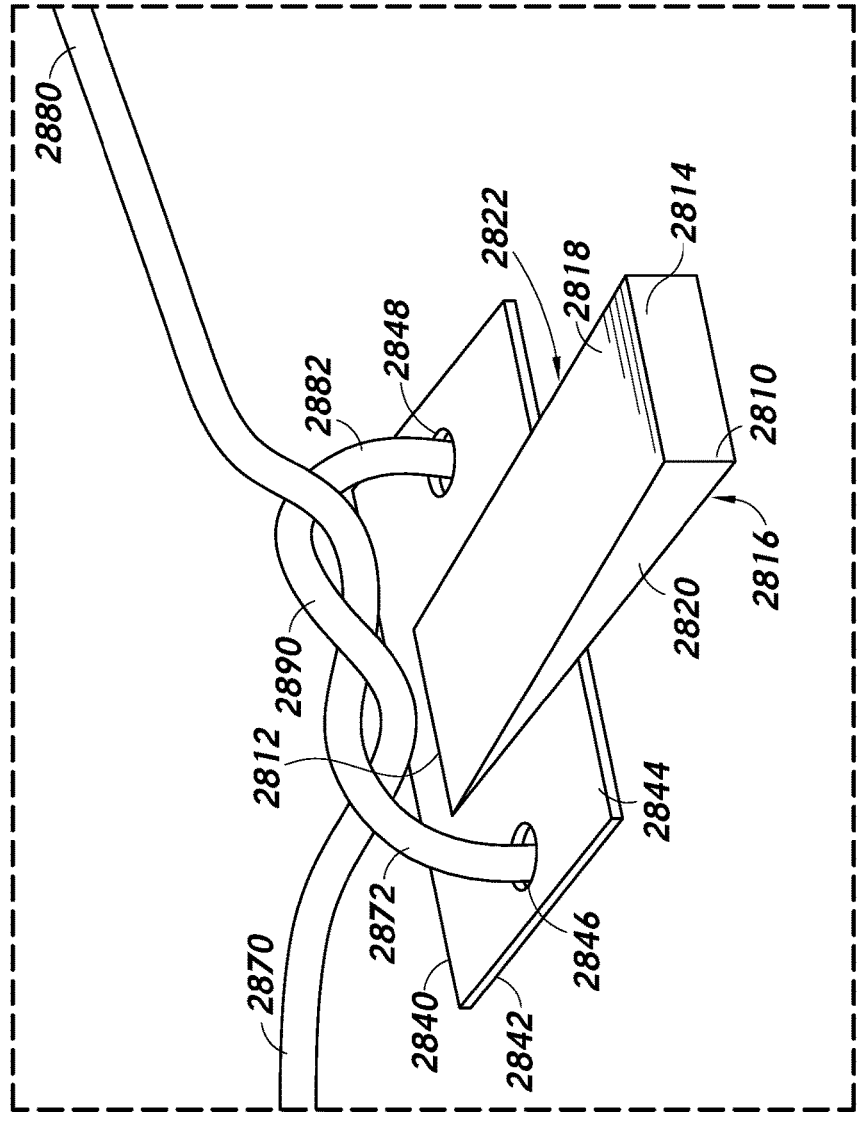
*FIG. 28*

2900

```
┌─────────────────────────────────────────────────────┐
│                                                     │  2902
│      POSITION SURGICAL PAD OVER TARGET TISSUE       │
│                                                     │
└─────────────────────────────────────────────────────┘
                          │
                          ▼
┌─────────────────────────────────────────────────────┐
│    PROVIDE FIRST SURGICAL CORD AND SECOND           │
│    SURGICAL CORD, EACH OF FIRST AND SECOND          │  2904
│    SURGICAL CORDS COMPRISING FIRST PORTION          │
│    EXTENDING EXTERNALLY OF TARGET TISSUE            │
└─────────────────────────────────────────────────────┘
                          │
                          ▼
┌─────────────────────────────────────────────────────┐
│   EXTEND FIRST PORTION OF FIRST SURGICAL CORD       │
│   AND FIRST PORTION OF SECOND SURGICAL CORD         │  2906
│   THROUGH THE SURGICAL PAD FROM THE FIRST           │
│   SURFACE TO THE SECOND SURFACE                     │
└─────────────────────────────────────────────────────┘
                          │
                          ▼
┌─────────────────────────────────────────────────────┐
│     SECURE FIRST SURGICAL CORD AND SECOND           │  2908
│     SURGICAL CORD TO SURGICAL PAD                   │
└─────────────────────────────────────────────────────┘
                          │
                          ▼
┌─────────────────────────────────────────────────────┐
│    POSITION SPACER BETWEEN TARGET TISSUE AND        │  2910
│    SURGICAL PAD                                     │
└─────────────────────────────────────────────────────┘
```

| |
|---|
| POSITION SURGICAL PAD OVER TARGET TISSUE | 3002

↓

| |
|---|
| PROVIDE FIRST SURGICAL CORD AND SECOND SURGICAL CORD, EACH OF FIRST AND SECOND SURGICAL CORDS COMPRISING FIRST PORTION EXTENDING EXTERNALLY OF TARGET TISSUE | 3004

↓

| |
|---|
| EXTEND FIRST PORTION OF FIRST SURGICAL CORD AND FIRST PORTION OF SECOND SURGICAL CORD THROUGH THE SURGICAL PAD FROM THE FIRST SURFACE TO THE SECOND SURFACE | 3006

↓

| |
|---|
| SECURE FIRST SURGICAL CORD AND SECOND SURGICAL CORD TO ONE ANOTHER OVER SECOND SURFACE OF SURGICAL PAD | 3008

↓

| |
|---|
| POSITION SPACER BETWEEN SECOND SURFACE OF SURGICAL PAD AND PORTIONS OF FIRST AND SECOND SURGICAL CORDS POSITIONED OVER SECOND SURFACE OF SURGICAL PAD | 3010

FIG. 30

SURGICAL PADS AND SPACERS

CROSS REFERENCE TO RELATED APPLICATIONS

This application is a continuation of International Patent Application No. PCT/US2021/028547, filed Apr. 22, 2021, which claims the benefit of U.S. Patent Application No. 63/148,246, filed Feb. 11, 2021, and of U.S. Patent Application No. 63/015,356, filed Apr. 24, 2020, the entire disclosures all of which incorporated by reference for all purposes.

BACKGROUND

Field

The present disclosure generally relates to the field of surgical pads and surgical spacers used in proximity to tissue openings.

Description of Related Art

As part of a medical procedure, surgical pads can be positioned over openings formed in any number of types of tissues and/or over an area of the tissues adjacent to the openings. The surgical pads can be used for a variety of purposes, including to facilitate closing of the openings and/or for anchoring one or more tethers extending through the openings.

SUMMARY

In some examples, described herein are systems and methods relating to surgical pads configured to be positioned over openings formed in target tissues, where the surgical pads can demonstrate improved mechanical strength when coupled to one or more tethers extending through the openings. In some examples, described herein are systems and methods relating to surgical pads which can be used in combination with an improved pattern of stitching around an opening to provide desired closure of the opening without or with reduced damage to any tethers extending through the opening.

In some implementations, a surgical pad can comprise a flexible pad portion configured to be positioned over an opening in a target tissue, the flexible pad portion comprising a first surface configured to be oriented toward the target tissue and a second surface configured to be oriented away from the target tissue. The surgical pad can include a plurality of designated locations around an outer edge portion of the second surface, each of the plurality of designated locations being configured to couple to corresponding tethers extending from the opening in the target tissue; and a plurality of elongate ribs associated with the second surface and coupled to the flexible pad portion, the plurality of elongate ribs being configured to provide mechanical reinforcement for the flexible pad portion to counter forces exerted upon the flexible pad portion by the corresponding tethers.

In some examples, the plurality of elongate ribs is arranged in a radially-extending pattern over the second surface. In some examples, the plurality of elongate ribs are coupled to one another over a center portion of the second surface. In some examples, the plurality of elongate ribs are not coupled to one another over a center portion of the second surface. In some examples, the plurality of elongate ribs are parallel to one another. In some examples, the plurality of elongate ribs is distributed evenly across the second surface.

In some examples, each of the plurality of elongate ribs comprises a lumen extending therethrough. In some examples, respective tethers are configured to extend from the opening in the target tissue through corresponding edge portions of the flexible pad portion and through a lumen of a corresponding elongate rib. In some examples, the plurality of elongate ribs is arranged in a radially extending pattern, wherein each of the plurality of elongate ribs comprises a first end over a center portion of the second surface and a second end over an outer edge portion of the flexible pad portion, and wherein respective tethers are configured to extend from the second end to the first end of each of the plurality of elongate ribs, and extend out from the first end.

In some examples, each of the plurality of elongate ribs is solid. In some examples, each of the plurality of elongate ribs comprises a linear rib. In some examples, each of the plurality of elongate ribs comprises cylindrical rods. In some examples, each of the plurality of elongate ribs comprises rods having a non-circular cross section.

In some examples, the plurality of elongate ribs is sutured to the flexible pad portion.

In some examples, the flexible pad portion comprises a plurality of fasteners extending from the second surface and corresponding portions of each of the plurality of elongate ribs is configured to be inserted between a respective fastener and the second surface to couple the plurality of elongate ribs to the flexible pad portion.

In some examples, the plurality of designated locations is evenly distributed around the outer edge portion of the second surface.

In some examples, each of the plurality of elongate ribs comprises a first end at a center portion of the second surface and a second end at a predetermined distance from a nearest portion of an outer edge of the flexible pad portion. In some examples, the plurality of designated locations comprises a designated location between each respective second end of each of the plurality of elongate ribs and a corresponding nearest portion of the outer edge of the flexible pad portion. In some examples, the plurality of designated locations is between the second ends of the plurality of elongate ribs.

In some examples, the flexible pad portion has a circular shape.

In some examples, the flexible pad portion comprises a non-biodegradable cross-linked tissue. The flexible pad portion can comprise bovine tissue treated with anti-thrombotic and anti-calcification treatments. In some examples, the plurality of elongate ribs comprises a non-biodegradable material. The plurality of elongate ribs can comprise at least one of a cobalt-chromium alloy, a nickel-titanium alloy, platinum, and tantalum.

In some examples, the flexible pad portion comprises biodegradable tissue. The flexible pad portion can comprise non-crosslinked decellularized biological material. In some examples, the plurality of elongate ribs comprises a biodegradable material. The plurality of elongate ribs can comprise a metallic alloy comprising at least one of magnesium, iron and zinc. The plurality of elongate ribs comprises at least one of a polylactic acid, a polyanhydride and a polyester.

In some examples, the surgical pad is configured to assume a reduced profile state for placement within a delivery catheter for transcatheter delivery to the target tissue, wherein the reduced profile state comprises the surgical pad in a folded state and first ends of the plurality of elongate ribs being oriented in a first direction and second ends of the plurality of elongate ribs being oriented in a second opposing direction. In some examples, the plurality of elongate ribs is arranged in a radial pattern and the surgical pad assumes an umbrella configuration in the reduced profile state. In some examples, the plurality of elongate ribs is parallel to one another and the surgical pad assumes an elongate configuration in the reduced profile state.

In some implementations, a method of deploying a surgical pad can comprise positioning a flexible pad portion over an opening in a target tissue, a first surface of the flexible pad portion being oriented toward the target tissue and a second surface of the flexible pad portion being oriented away from the target tissue, and wherein a plurality of elongate ribs is associated with the second surface and coupled to the flexible pad portion. The method can include threading each of a plurality of tethers extending from the opening in the target tissue through the flexible pad portion at a corresponding designated location distributed around an outer edge portion of the second surface, and securing the plurality of tethers to the flexible pad portion.

In some examples, threading each of the plurality of tethers through the flexible pad portion comprises threading a pair of tethers extending from the opening in the target tissue to the corresponding designated location.

In some examples, positioning the flexible pad portion over the opening in the target tissue comprises positioning the flexible pad portion over an opening in a heart wall, and wherein threading the plurality of tethers through the flexible pad portion comprises threading a pair of tethers extending from a location on a heart valve leaflet through the corresponding designated location.

In some examples, securing the plurality of tethers to the flexible pad portion comprises securing the plurality of tethers to the corresponding designated location. In some examples, securing the plurality of tethers to the flexible pad portion comprises tying a suture knot over the second surface with a pair of tethers at the corresponding designated location.

In some examples, each of the plurality of elongate ribs comprises a lumen extending therethrough from a first end to a second end, and wherein the method further comprises threading each of the plurality of tethers through a lumen of a respective elongate rib from a first end to a second end of the respective elongate rib after threading each of the plurality of tethers through the flexible pad portion at the corresponding designated location. In some examples, securing the plurality of tethers to the flexible pad portion comprises tying a suture knot over the second surface with a pair of tethers after threading the pair of tethers through the lumen of the respective elongate rib from the first end to the second end of the respective elongate rib. In some examples, the plurality of elongate ribs is in a radial pattern over the second surface, the first end of each of the plurality of elongate ribs is over a center portion of the second surface and the second end of each of the plurality of elongate ribs are over an outer edge portion of the second surface, and wherein securing the plurality of tethers comprises tying the suture knot over the center portion of the second surface.

In some examples, the method further comprises transporting the surgical pad in a reduced profile state to the target tissue using a transcatheter delivery approach, wherein the reduced profile state comprises a folded flexible pad portion, first ends of the plurality of elongate ribs being oriented in a first direction and second ends of the plurality of elongate ribs being oriented in a second opposing direction.

In some implementations, a suture system can comprise a surgical pad configured to be positioned over a target tissue, the surgical pad comprising: a central opening in a center portion aligned with an opening in the target tissue and being configured to allow extension therethrough of surgical instrumentation, and a plurality of edge openings distributed around an outer edge portion of the surgical pad. The suture system can include a plurality of anchor cords comprising a portion configured to be deployed into the target tissue and another portion configured to be extending through the plurality of edge openings.

In some examples, each of the plurality of edge openings comprises a radially extending slit which opens up to an outer edge of the surgical pad.

In some examples, the plurality of edge openings is distributed evenly around the outer edge portion. In some examples, the plurality of edge openings is distributed in a circular pattern around the outer edge portion of the surgical pad.

In some examples, the surgical pad comprises a circular outer edge and wherein the central opening comprises a circular shape.

In some examples, each of the plurality of anchor cords comprises an eyelet configured to be positioned over a corresponding edge opening and a secondary cord is configured to be threaded through eyelets of the plurality of anchor cords.

In some implementations, a surgical pad can comprise a central opening in a center portion of the surgical pad configured to be aligned with an opening in a target tissue over which the surgical pad is positioned, and a plurality of edge openings around an outer edge portion of the surgical pad.

In some examples, each of the plurality of edge openings comprises a slit which opens up to an outer edge of the surgical pad.

In some examples, the plurality of edge openings is distributed evenly around the outer edge portion.

In some examples, the surgical pad comprises a circular outer edge and wherein the central opening comprises a circular shape. In some examples, the plurality of edge openings is at positions that form a circular pattern around the outer edge portion of the surgical pad.

In some examples, the surgical pad is a pledget.

In some implementations, a method can comprise providing a surgical pad comprising a central opening in a center portion of the surgical pad and a plurality of edge openings around an outer edge portion of the surgical pad, and positioning the surgical pad over a target tissue, the central opening in alignment with an opening in the target tissue. The method can include providing a plurality of anchor cords, each of the plurality of anchor cords comprising a portion extending through a corresponding edge opening and another portion embedded within the target tissue, and tensioning the plurality of anchor cords extending through the plurality of edge openings to reduce a size of the opening.

In some examples, the method can further comprise extending the plurality of anchor cords through the plurality of edge openings prior to positioning the surgical pad over the target tissue.

In some examples, each of the plurality of edge openings comprises a slit and wherein the method further comprises extending the plurality of anchor cords through corresponding slits after positioning the surgical pad over the target tissue.

In some examples, the surgical pad comprises edge openings on opposing edge portions, and the method further comprising threading the plurality of anchor cords through a second opening on an opposing edge portion prior to tensioning the plurality of anchor cords to reduce the size of the opening.

In some examples, the method further comprises threading the plurality of anchor cords through a second edge opening prior to tensioning the plurality of anchor cords, the second edge opening being selected to provide an opening in routing of the plurality of anchor cords, the opening in the routing of the plurality of anchor cords aligning with the opening in the target tissue and the central opening of the surgical pad.

In some examples, each of the plurality of anchor cords comprises an eyelet configured to be positioned over a respective edge opening, and the method further comprising threading a secondary cord through eyelets of the plurality of anchor cords. In some examples, the method further comprises tensioning the secondary cord to reduce the size of the opening.

In some examples, providing the plurality of anchor cords comprises providing a number of pairs of anchor cords that corresponds to a number of edge openings, each of the pairs of anchor cords comprising a portion embedded within a portion of a heart wall beneath the corresponding edge opening.

In some examples, the method can further comprise deploying each of the plurality of anchor cords into the target tissue through a corresponding edge opening of the surgical pad subsequent to positioning the central opening of the surgical pad in alignment with the opening in the target tissue to provide the plurality of anchor cords each comprising the portion extending through the corresponding edge opening and the other portion embedded within the target tissue.

In some examples, described herein are systems, devices and methods related to one or more spacers which can be used in combination with one or more surgical pads, such as one or more surgical pads as described herein. The one or more spacers can facilitate adjustment in the tension of one or more surgical cords secured to a surgical pad.

In some implementations, a method can comprise positioning a surgical pad over a target tissue, a first surface of the surgical pad being oriented toward the target tissue and a second surface of the surgical pad being oriented away from the target tissue. The method can include providing a first surgical cord and a second surgical cord, each of the first and second surgical cords comprising a first portion extending externally of the target tissue and a second portion embedded within the target tissue; and extending the first portion of the first surgical cord through the surgical pad from the first surface to the second surface and extending the first portion of the second surgical cord through the surgical pad from the first surface to the second surface. The method can include securing the first surgical cord and the second surgical cord to the surgical pad; and positioning a spacer between the target tissue and the surgical pad to provide a corresponding separation between the target tissue and the surgical pad and to tension the first and second surgical cords secured to the surgical pad.

In some examples, positioning the surgical pad over the target tissue can comprise positioning the surgical pad over an opening in the target tissue, wherein providing the first surgical cord and the second surgical cord comprises providing a first tether and a second tether, the first portion of the first tether and the first portion of the second tether extending through the opening in the target tissue, and wherein extending the first portion of the first surgical cord through the surgical pad comprises extending the first portion of the first tether from the first surface to the second surface at a first location on the surgical pad and extending the first portion of the second surgical cord through the surgical pad comprises extending the first portion of the second tether from the first surface to the second surface at a second location on the surgical pad.

In some examples, the method can further comprise providing a third tether and a fourth tether, and a fifth tether and a sixth tether, wherein each of the third and fourth tethers, and the fifth and sixth tethers comprises a respective first portion extending from the opening and a second portion embedded within the target tissue; extending the third tether and the fourth tether through the surgical pad from the first surface to the second surface at a respective third location and fourth location on the surgical pad and extending the fifth tether and the sixth tether through the surgical pad from the first surface to the second surface at a respective fifth and sixth location on the surgical pad; and securing the third and fourth tethers to the surgical pad, and securing the fifth and sixth tethers to the surgical pad.

In some examples, the first and second locations are laterally spaced from one another along a first lateral dimension and form a first pair of locations, the third and fourth locations are laterally spaced from one another along a second lateral dimension and form a second pair of locations, the fifth and sixth locations are laterally spaced from one another along a third lateral dimension and form a third pair of locations, wherein the first, second and third lateral dimensions are parallel to one another, wherein the first, third and fifth locations are aligned with one another along a first longitudinal direction perpendicular to the first, second and third lateral dimensions, and wherein the second, fourth and sixth locations are aligned with one another along a second longitudinal dimension parallel with the first longitudinal dimension and perpendicular to the first, second and third lateral dimensions.

In some examples, the spacer can comprise a first protrusion laterally spaced from a second protrusion, an intermediate portion extending perpendicularly between the first and second protrusions, and the first and second protrusions extending from a same side of the intermediate portion.

In some examples, positioning the spacer between the target tissue and the surgical pad can comprise positioning the first protrusion adjacent to and in contact with a first portion of the first surface of the surgical pad on a first side of the first location; and positioning the second protrusion adjacent to and in contact with a second portion of the first surface of the surgical pad to a second side of the second location oriented away from the first side, wherein the first protrusion and second protrusion comprise an orientation parallel to the first and second longitudinal dimensions.

In some examples, positioning the spacer between the target tissue and the surgical pad can comprise positioning the first protrusion adjacent to and in contact with a first portion of the first surface of the surgical pad on a first side of the first and second locations; and positioning the second protrusion adjacent to and in contact with a second portion of the first surface of the surgical pad to a second side of the first and second locations oriented away from the first side, wherein the first protrusion and second protrusion comprise an orientation parallel to the first, second and third lateral dimensions.

In some examples, the spacer can comprise a first protrusion laterally spaced from a second protrusion, a third protrusion laterally spaced from the second protrusion, a first intermediate portion extending perpendicularly between the first and second protrusions and a second intermediate portion extending perpendicularly between the second and third protrusions, and the first, second and third protrusions extending from a same side of the first and second intermediate portions. Positioning a spacer between the target tissue and the surgical pad can comprises positioning the first protrusion adjacent to and in contact with a first portion of the first surface of the surgical pad on a first side of the first pair of locations; positioning the second protrusion adjacent to and in contact with a second portion of the first surface of the surgical pad on a second side of the first pair of locations and between the first pair of locations and the second pair of locations; and positioning the third protrusion adjacent to and in contact with a third portion of the first surface of the surgical pad to a second side of the second pair of locations oriented away from the second side of the first pair of locations, wherein the first protrusion, second protrusion, and third protrusion comprise an orientation parallel to the first, second and third lateral dimensions.

In some examples, the first and second locations are a first pair of locations, the third and fourth locations are a second pair of locations, the fifth and sixth locations are a third pair of locations, and wherein the first pair of locations, second pair of locations, and third pair of locations are at respective positions along a curved path.

In some examples, the spacer can comprise a first protrusion laterally spaced from a second protrusion, and an intermediate portion comprising a curved configuration and extending between the first and second protrusions, the first and second protrusions extending from a same side of the intermediate portion and being oriented toward one another. Positioning the spacer between the target tissue and the surgical pad can comprise positioning the first protrusion adjacent to and in contact with a first portion of the first surface of the surgical pad to a first side of the second pair of locations between the first pair of locations and the second pair of locations; and positioning the second protrusion adjacent to and in contact with a second portion of the first surface of the surgical pad to a second side of the second pair of locations between the third pair of locations and the second pair of locations.

In some examples, positioning the spacer between the target tissue and the surgical pad comprises positioning the spacer adjacent to and in contact with a first portion of the first surface of the surgical pad between the first pair of locations and the second pair of locations or adjacent to and in contact with a second portion of the first surface of the surgical pad between the second pair of locations and the third pair of locations.

In some examples, the method can further comprise extending the first tether and second tether through a lumen of a first elongate rib over the second surface of the surgical pad from an outer edge distal end to a center portion distal end of the first elongate rib; extending the third tether and fourth tether through a lumen of a second elongate rib over the second surface of the surgical pad from an outer edge distal end to a center portion distal end of the second elongate rib; extending the fifth tether and sixth tether through a lumen of a third elongate rib over the second surface of the surgical pad from an outer edge distal end to a center portion distal end of the third elongate rib; and securing the first, second, third, fourth, fifth and sixth tethers to one another over the center portion of the second surface, wherein positioning the spacer between the target tissue and the surgical pad comprises positioning the spacer adjacent to and in contact with a center portion of the first surface of the surgical pad.

In some examples, positioning the surgical pad over the target tissue comprises positioning the surgical pad over a portion of the target tissue surrounding an opening in the target tissue and aligning a central opening of the surgical pad with the opening, wherein providing the first surgical cord and the second surgical cord comprises providing a first anchor cord and a second anchor cord, the first portion of the first anchor cord and the first portion of the second anchor cord extending from within the target tissue from a respective position adjacent to the opening in the target tissue, and wherein extending the first portion of the first surgical cord through the surgical pad and extending the first portion of the second surgical cord through the surgical pad comprises extending the first portion of the first anchor cord and the first portion of the second anchor cord from the first surface to the second surface through a first location on the surgical pad.

In some examples, the method can further comprise providing a third anchor cord and a fourth anchor cord, and a fifth anchor cord and a sixth anchor cord, wherein each of the third and fourth anchor cord, and the fifth and sixth anchor cords comprises a respective first portion extending from a respective position adjacent to the opening in the target tissue and a second portion embedded within the target tissue; extending the third anchor cord and the fourth anchor cord through the surgical pad from the first surface to the second surface at second location on the surgical pad and extending the fifth anchor cord and the sixth anchor cord through the surgical pad from the first surface to the second surface at a third location on the surgical pad; and securing the third and fourth anchor cords to the surgical pad, and securing the fifth and sixth anchor cords to the surgical pad, wherein the first location, second location, and third location are at respective positions along a curved path.

In some examples, the spacer can comprise a first protrusion laterally spaced from a second protrusion, and an intermediate portion comprising a curved configuration and extending between the first and second protrusions, the first and second protrusions extending from a same side of the intermediate portion and being oriented toward one another. Positioning the spacer between the target tissue and the surgical pad can comprise positioning the first protrusion adjacent to and in contact with a first portion of the first surface of the surgical pad to a first side of the second location between the first location and the second location; and positioning the second protrusion adjacent to and in contact with a second portion of the first surface of the surgical pad to a second side of the second location between the third location and the second location.

In some examples, positioning the spacer between the target tissue and the surgical pad comprises positioning the spacer adjacent to and in contact with a first portion of the first surface of the surgical pad between the first location and the second location or adjacent to and in contact with a second portion of the first surface of the surgical pad between the second location and the third location.

In some examples, the method can further comprise positioning a plurality of spacers between the target tissue and the surgical pad, wherein positioning the plurality of spacers comprises positioning at least some of the plurality of spacers to share a vertical plane. In some examples, the method can further comprise positioning a plurality of spacers between the target tissue and the surgical pad, wherein positioning the plurality of spacers comprises positioning the plurality of spacers laterally relative to one another, at least some of the plurality of spacers being positioned adjacent to and in contact with a respective portion of the first surface of the surgical pad. In some examples, positioning the plurality of spacers can comprise positioning a plurality of identical spacers. In some examples, positioning the plurality of spacers can comprise positioning at least one spacer comprising a feature different from that of another of the plurality of spacers.

In some implementations, a method can comprise positioning a surgical pad over a target tissue, a first surface of the surgical pad being oriented toward the target tissue and a second surface of the surgical pad being oriented away from the target tissue; providing a first surgical cord and a second surgical cord, each of the first and second surgical cords comprising a first portion extending externally of the target tissue and a second portion embedded within the target tissue; extending the first portion of the first surgical cord through the surgical pad from the first surface to the second surface and extending the first portion of the second surgical cord through the surgical pad from the first surface to the second surface; securing the first surgical cord and the second surgical cord to one another over the second surface of the surgical pad; and positioning a spacer between the second surface of the surgical pad and portions of the first and second surgical cords positioned over the second surface of the surgical pad to provide a corresponding separation between the surgical pad and to tension the first and second surgical cords.

In some examples, extending the first surgical cord through the surgical pad and extending the second surgical cord through the surgical pad comprises extending the first and second surgical cords through the surgical pad at a respective first and second location on the surgical pad, and wherein securing the first and second surgical cords comprises forming a knot over the second surface of the surgical pad using respective portions of the first and second surgical cords.

In some examples, positioning the spacer between the second surface of the surgical pad and the portions of the first and second surgical cords positioned over the second surface of the surgical pad comprises positioning the spacer between the knot and the second surface of the surgical pad.

In some examples, the method can further comprise positioning a plurality of spacers between the target tissue and the surgical pad, wherein positioning the plurality of spacers comprises positioning the plurality of spacers to share a vertical plane. In some examples, positioning the plurality of spacers comprises positioning a plurality of identical spacers. In some examples, positioning the plurality of spacers comprises positioning at least one spacer comprising a feature different from that of another of the plurality of spacers.

In some implementations, a system can comprise a surgical pad configured to be positioned over a target tissue, a first surface of the surgical pad being configured to be oriented toward the target tissue and a second surface of the surgical pad being configured to be oriented away from the target tissue; a first surgical cord and a second surgical cord configured to be secured to the surgical pad, each of the first and second surgical cords comprising a first portion configured to be extending externally of the target tissue and a second portion configured to be embedded within the target tissue; and a spacer configured to be positioned between the target tissue and the surgical pad, to provide a separation between the surgical pad and the target tissue and to tension the first and second surgical cords.

In some examples, the surgical pad can comprise a first location at which the first portion of the first surgical cord is configured to be extended therethrough and a second location at which the first portion of the second surgical cord is configured to be extended therethrough, wherein the spacer comprises a first protrusion laterally spaced from a second protrusion and an intermediate portion extending perpendicularly between the first and second protrusions, the first and second protrusions extending from a same side of the intermediate portion, and wherein is the first protrusion is configured to be positioned adjacent to and in contact with a first portion of the first surface of the surgical pad on a first side of the first location and the second protrusion is configured to be positioned adjacent to and in contact with a second portion of the first surface of the surgical pad on a second side of the second location oriented away from the first location.

In some examples, the first and second locations on the surgical pad are laterally spaced from one another along a first lateral dimension and form a first pair of locations, and wherein the surgical pad can further comprise a third location and fourth location laterally spaced from one another along a second lateral dimension and forming a second pair of locations, each of the third and fourth locations being configured to allow extension therethrough of a respective surgical cord; a fifth location and sixth location laterally spaced from one another along a third lateral dimension and forming a third pair of locations, each of the fifth and sixth locations being configured to allow extension therethrough of a respective surgical cords; wherein the first, second and third lateral dimensions are parallel to one another, wherein the first, third and fifth locations are aligned with one another along a first longitudinal direction perpendicular to the first, second and third lateral dimensions, and wherein the second, fourth and sixth locations are aligned with one another along a second longitudinal dimension parallel with the first longitudinal dimension and perpendicular to the first, second and third lateral dimensions.

In some examples, the spacer can comprise a first protrusion laterally spaced from a second protrusion; an intermediate portion extending perpendicularly between the first and second protrusions, the first and second protrusions extending from a same side of the intermediate portion, wherein first protrusion is configured to be positioned adjacent to and in contact with a first portion of the first surface of the surgical pad on a first side of the first location and the second protrusion is configured to be positioned adjacent to and in contact with a second portion of the first surface of the surgical pad on a second side of the second location oriented away from the first location, and wherein the first protrusion and second protrusion comprise an orientation parallel to the first and second longitudinal dimensions.

In some examples, the spacer can comprise a first protrusion laterally spaced from a second protrusion; an intermediate portion extending perpendicularly between the first and second protrusions, the first and second protrusions extending from a same side of the intermediate portion, wherein first protrusion is configured to be positioned adjacent to and in contact with a first portion of the first surface of the surgical pad on a first side of the first location and the second protrusion is configured to be positioned adjacent to and in contact with a second portion of the first surface of the surgical pad on a second side of the second location oriented away from the first location, and wherein the first protrusion and second protrusion comprise an orientation parallel to the first, second and third lateral dimensions.

In some examples, the spacer can comprise a first protrusion laterally spaced from a second protrusion; a third protrusion laterally spaced from the second protrusion; a first intermediate portion extending perpendicularly between the first and second protrusions; and a second intermediate portion extending perpendicularly between the second and third protrusions, wherein the first, second and third protrusions extend from a same side of the first and second intermediate portions, wherein the first protrusion is configured to be positioned adjacent to and in contact with a first portion of the first surface of the surgical pad on a first side of the first pair of locations, wherein the second protrusion is configured to be positioned adjacent to and in contact with a second portion of the first surface of the surgical pad on a second side of the first pair of locations and between the first pair of locations and the second pair of locations, wherein the third protrusion is configured to be positioned adjacent to and in contact with a third portion of the first surface of the surgical pad to a second side of the second pair of locations oriented away from the second side of the first pair of locations, and wherein the first protrusion, second protrusion, and third protrusion comprise an orientation parallel to the first, second and third lateral dimensions.

In some examples, the spacer can comprise a U-shape. In some examples, the first protrusion and the second protrusion can each comprise an elongate portion.

In some examples, the surgical pad can comprise a first location at which the first portion of the first surgical cord is configured to be extended therethrough and a second location at which the first portion of the second surgical cord is configured to be extended therethrough, wherein the first and second locations on the surgical pad are laterally spaced from one another and form a first pair of locations. The surgical pad can further comprise a third location and fourth location laterally spaced from one another and forming a second pair of locations, each of the third and fourth locations being configured to allow extension therethrough of a respective surgical cord; a fifth location and sixth location laterally spaced from one another and forming a third pair of locations, each of the fifth and sixth locations being configured to allow extension therethrough of a respective surgical cord, and wherein the first pair of locations, second pair of locations, and third pair of locations are at respective positions along a curved path.

In some examples, the spacer can comprise a first protrusion laterally spaced from a second protrusion, the first and second protrusions extending from a same side of the intermediate portion and being oriented toward one another, and an intermediate portion comprising a curved configuration and extending between the first and second protrusions, wherein the first protrusion is configured to be positioned adjacent to and in contact with a first portion of the first surface of the surgical pad to a first side of the second pair of locations between the first pair of locations and the second pair of locations; and wherein the second protrusion is configured to be positioned adjacent to and in contact with a second portion of the first surface of the surgical pad to a second side of the second pair of locations between the third pair of locations and the second pair of locations.

In some examples, the spacer can be configured to be positioned adjacent to and in contact with a first portion of the first surface of the surgical pad between the first pair of locations and the second pair of locations or adjacent to and in contact with a second portion of the first surface of the surgical pad between the second pair of locations and the third pair of locations.

In some examples, the first protrusion and the second protrusion can each comprise a wedge shape.

In some examples, the surgical pad can further comprise a first elongate rib over the second surface of the surgical pad comprising a first lumen extending therethrough, wherein a first respective pair of surgical cords is configured to extend from an outer edge distal end to a center portion distal end of the first elongate rib; and a second elongate rib over the second surface of the surgical pad comprising a second lumen extending therethrough, wherein a second respective pair of surgical cords is configured to extend from an outer edge distal end to a center portion distal end of the second elongate rib, wherein the first and second pairs of surgical cords are configured to be secured over a center portion of the second surface of the surgical pad, and wherein the spacer is configured to be positioned adjacent to and in contact with a center portion of the first surface of the surgical pad.

In some examples, the spacer can comprise a partial ring shape.

In some examples, the surgical pad can further comprise a first location configured to allow extension therethrough of the first surgical cord and second surgical cord; a second location configured to allow extension therethrough of a third surgical cord and fourth surgical cord; and a third location configured to allow extension therethrough of a fifth surgical cord and sixth surgical cord, wherein the first location, second location, and third location are at respective positions along a curved path.

In some examples, the spacer can comprise a first protrusion laterally spaced from a second protrusion; and an intermediate portion comprising a curved configuration and extending between the first and second protrusions, the first and second protrusions extending from a same side of the intermediate portion and being oriented toward one another, wherein the first protrusion is configured to be positioned adjacent to and in contact with a first portion of the first surface of the surgical pad to a first side of the second location between the first location and the second location, and wherein the second protrusion is configured to be positioned adjacent to and in contact with a second portion of the first surface of the surgical pad to a second side of the second location between the third location and the second location.

In some examples, the spacer can be configured to be positioned adjacent to and in contact with a first portion of the first surface of the surgical pad between the first location and the second location or adjacent to and in contact with a second portion of the first surface of the surgical pad between the second location and the third location.

In some examples, the spacer can comprise a partial ring shape.

In some implementations, a system can comprise a surgical pad configured to be positioned over a target tissue, a first surface of the surgical pad being configured to be oriented toward the target tissue and a second surface of the surgical pad being configured to be oriented away from the target tissue; a first surgical cord and a second surgical cord, each of the first and second surgical cords comprising a first portion configured to be extending externally of the target tissue and a second portion configured to be embedded within the target tissue, the first and second surgical cords being configured to be secured to one another over the second surface of the surgical pad; and a spacer configured to be positioned between the second surface of the surgical pad and portions of the first and second surgical cords positioned over the second surface of the surgical pad, to provide a separation between the surgical pad and the target tissue and to tension the first and second surgical cords.

In some examples, the spacer can comprise an elongate configuration.

In some examples, the spacer can comprise a wedge configuration.

Each method disclosed herein also encompass one or more simulations of the method, which are useful, for example, for teaching, demonstration, testing, device development, and procedure development. For example, methods for treating or diagnosing a patient include corresponding simulated methods performed on simulated patients. Suitable simulated patients or anthropogenic ghosts can include any combination of physical and virtual elements. Examples of physical elements include whole human or animal cadavers, or any portion thereof, including, organ systems, individual organs, or tissue; and manufactured cadaver, organ system, organ, or tissue simulations. Examples of virtual elements include visual simulations, which can be displayed on a screen; projected on a screen, surface, space, or volume; and holographic images. The simulation can also include one or more of another type of sensory input, for example, auditory, tactile, and olfactory stimuli.

For purposes of summarizing the disclosure, certain aspects, advantages and novel features have been described herein. It is to be understood that not necessarily all such advantages may be achieved in accordance with any particular example. Thus, the disclosed examples may be carried out in a manner that achieves or optimizes one advantage or group of advantages as taught herein without necessarily achieving other advantages as may be taught or suggested herein.

BRIEF DESCRIPTION OF THE DRAWINGS

Various examples are depicted in the accompanying drawings for illustrative purposes and should in no way be interpreted as limiting the scope of the disclosure. In addition, various features of different disclosed examples can be combined to form additional examples, which are part of this disclosure. Throughout the drawings, reference numbers may be reused to indicate correspondence between reference elements. However, it should be understood that the use of similar reference numbers in connection with multiple drawings does not necessarily imply similarity between respective examples associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some examples or configurations.

FIG. 6 is a plan view of an example of a surgical pad comprising four elongate ribs and eight designated locations.

FIG. 7 is a plan view of an example of a surgical pad comprising six elongate ribs and six designated locations.

FIG. 8 is a plan view of an example of a surgical pad comprising eight elongate ribs and eight designated locations.

FIG. 9 is a plan view of an example of a surgical pad comprising a plurality of elongate ribs which are not coupled to one another.

FIG. 11 is a process flow diagram of an example of a process to deploy a surgical pad.

FIG. 18 is a process flow diagram of an example of a deployment process for deploying a suture system as described herein.

FIG. 27A is a perspective view of an example of a suture system comprising a spacer, and FIG. 27B is a perspective view of the spacer of FIG. 27A.

FIG. 28 is a perspective view of an example of a suture system comprising a spacer configured to be positioned between a surgical pad and portions of surgical cords secured to the surgical pad.

FIG. 29 is a process flow diagram of an example of a deployment process for deploying a spacer as described herein.

FIG. 30 is a process flow diagram of another example of a deployment process for deploying a spacer as described herein.

DETAILED DESCRIPTION

Figure 1:
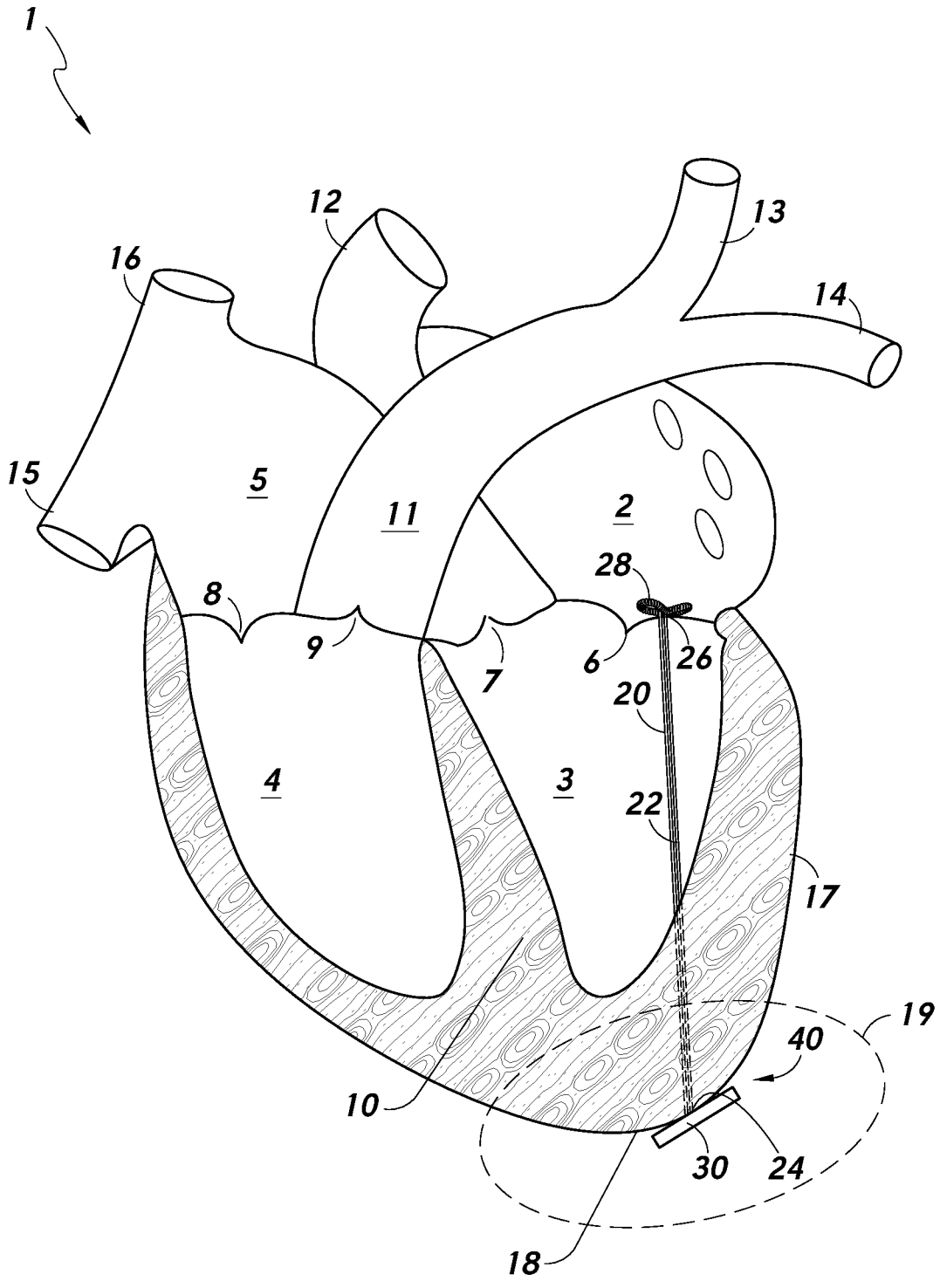
FIG. 1 is a cross-sectional view of a human heart.

The headings provided herein are for convenience only and do not necessarily affect the scope or meaning of the claims.

In some examples, the present disclosure relates to systems and methods for surgical pads configured to be positioned over tissue openings, where the surgical pads can demonstrate improved mechanical strength when coupled to one or more tethers extending through the tissue openings. In some examples, the present disclosure relates to systems and methods for surgical pads which can be used in combination with an improved pattern of stitching around an opening to provide desired closure of the opening without or with reduced damage to any tethers extending through the opening.

Although certain preferred examples are disclosed below, inventive subject matter extends beyond the specifically disclosed examples to other alternative examples and/or uses and to modifications and equivalents thereof. Thus, the scope of the claims that may arise herefrom is not limited by any of the particular examples described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain examples; however, the order of description should not be construed to imply that these operations are order dependent. Additionally, the structures, systems, and/or devices described herein may be embodied as integrated components or as separate components. For purposes of comparing various examples, certain aspects and advantages of these examples are described. Not necessarily all such aspects or advantages are achieved by any particular example. Thus, for example, various examples may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred examples. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element (s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Openings can be formed at various target tissue sites, for example to access a lumen and/or chamber through the tissue. In some cases, openings can be formed in the heart wall. For example, the openings can be formed in the heart wall to provide access to one or more heart chambers so as to treat various heart conditions, including any number of heart valve abnormalities. An opening can be formed in the ventricular heart wall, including the left ventricular heart wall, to perform heart valve repair and/or replacement.

FIG. 1 shows various features of a human heart 1. The heart 1 includes four chambers, namely the left atrium 2, the left ventricle 3, the right ventricle 4, and the right atrium 5. A wall of muscle, referred to as the septum 10, separates the left atrium 2 and right atrium 5, and the left ventricle 3 and right ventricle 4. Blood flow through the heart 1 is at least partially controlled by four valves, the mitral valve 6, aortic valve 7, tricuspid valve 8, and pulmonary valve 9. The mitral valve 6 separates the left atrium 2 and the left ventricle 3 and controls blood flow therebetween. The aortic valve 7 separates and controls blood flow between the left ventricle 3 and the aorta 12. The tricuspid valve 8 separates the right atrium 5 and the right ventricle 4 and controls blood flow therebetween. The pulmonary valve 9 separates the right ventricle 4 and the pulmonary artery 11, controlling blood flow therebetween.

In a healthy heart, the heart valves can properly open and close in response to a pressure gradient present during various stages of the cardiac cycle (e.g., relaxation and contraction) to at least partially control the flow of blood to a respective region of the heart and/or to blood vessels. Deoxygenated blood arriving from the rest of the body generally flows into the right side of the heart for transport to the lungs, and oxygenated blood from the lungs generally flows into the left side of the heart for transport to the rest of the body. During ventricular diastole, deoxygenated blood arrive in the right atrium 5 from the inferior vena cava 15 and superior vena cava 16 to flow into the right ventricle 4, and oxygenated blood arrive in the left atrium 2 from the pulmonary veins to flow into the left ventricle 3. During ventricular systole, deoxygenated blood from the right ventricle 4 can flow into the pulmonary artery 11 for transport to the lungs (e.g., via the left 14 and right 13 pulmonary arteries), and oxygenated blood can flow from the left ventricle 3 to the aorta 12 for transport to the rest of the body.

A number of conditions can contribute to a higher than normal pressure in the left atrium. Dysfunction of the mitral valve can contribute to elevated left atrial pressure. Conditions such as mitral valve regurgitation and/or stenosis may result in difficulty in pumping blood from the left atrium to the left ventricle, contributing to elevated pressure in the left atrium. Valve stenosis can cause a valve to become narrowed or obstructed. Mitral valve stenosis can restrict blood flow from the left atrium to the left ventricle. Valve regurgitation occurs when a valve does not close properly. For example, regurgitation can occur due to improper coaptation of the valve leaflets, such as due to prolapse of one or more of the valve leaflets. Mitral valve regurgitation can result in blood flow leakage back into the left atrium 2 from the left ventricle 3 when the left ventricle 3 contracts. Restricted flow of blood from the left atrium 2 into the left ventricle 3, and blood flow leakage from the left ventricle 3 back into the left atrium 2 can both contribute to elevated atrial pressure. Dysfunction in the left ventricle 3 can also contribute to elevated left atrial pressure. Elevated left atrial pressure may lead to left atrial enlargement, producing symptoms such as shortness of breath during exertion, fatigue, chest pain, fainting, abnormal heartbeat, and swelling of the legs and feet.

Forming an opening 40 through the heart wall 17 can be used to access a heart valve for treating various heart valve irregularities. Heart valve repair and/or replacement procedures can be performed to improve or restore valve function. For example, mitral valve repair procedures can be performed to alleviate mitral valve dysfunction, including mitral valve prolapse. In some cases, a transapical approach can be used to gain access into the heart 1. For example, mitral valve repair procedures can include accessing the mitral valve 6 from within the left ventricle 3, where entry into the left ventricle 3 can be achieved through the apex region 19 of the heart 1. The heart wall 17 can be punctured in the apex region 19 to form the opening 40 so as to allow delivery of medical devices and/or therapy to the mitral valve 6. The apex region 19 is schematically shown in FIG. 1 as the area within the dashed circle. As used herein, the "apex region" can include the true apex 18 of the heart 1 and an area of the heart wall 17 covering up to about 5 centimeters (cm) around the true apex 18. For example, the opening in the left ventricular portion of the heart wall 17 about 2 centimeters (cm) to about 4 centimeters (cm) from the true apex 18.

Mitral valve repair and/or replacement procedures can be performed to improve or restore mitral valve function. FIG. 1 shows a tether 20 coupling a leaflet of the mitral valve 6 to the heart wall 17. Mitral valve repair surgeries can comprise deploying one or more tethers onto a mitral valve leaflet for tethering the leaflet to the heart wall 17. Coupling the leaflet to the heart wall 17 can facilitate reshaping of the mitral valve 6, such as to reduce or eliminate leaflet prolapse. The tether 20 can serve to improve coaptation of the leaflet. In some examples, the tether 20 can be configured to couple the leaflet to a left ventricular portion of the heart wall 17. In some examples, more than one tether can be used to couple the leaflet to the heart wall 17. These tethers can be made from a variety of materials. One or more of these tethers can comprise for example expanded polytetrafluoroethylene (ePTFE). For example, the tether 20 can be an ePTFE suture.

The tether 20 can comprise an elongate portion 22 which extends between a proximal end 24 and a distal end 26. The proximal end 24 of the tether 20 can be coupled to the heart wall 17. The distal end 26 of the tether 20 can be coupled to the leaflet of the mitral valve 6. In some examples, the distal end 26 can be coupled to a suture knot 28 to facilitate securing the tether 20 to the leaflet. The suture knot 28 can be positioned at least partially over an upper surface of the leaflet. For example, the suture knot 28 can be positioned over an atrial facing surface of the mitral valve leaflet. The proximal end 24 can be anchored to a portion of the heart wall 17 at or proximate to the apex 18 of the heart 1, such as in the apex region 19. In some examples, a portion of the elongate portion 22 can extend at least partially through the heart wall 17. FIG. 1 shows the tether 20 extending through an entire thickness of the heart wall 17. In some cases, the proximal end 24 can be anchored at a position adjacent to an externally facing surface of the pericardium. In some cases, the proximal end 24 can be anchored at a position external to the heart 1. In some cases, the tether 20 can extend partially through the heart wall 17 such that the proximal end 24 is anchored within or adjacent to a layer of the heart wall 17, including for example the epicardium or the myocardium.

The proximal end 24 can be coupled to a pad 30. The tether 20 can couple the mitral valve leaflet to the pad 30, extending from the leaflet through the left ventricle 3 and opening 40 in the heart wall 17 to the pad 30. In some cases, the pad 30 can be positioned over and/or adjacent to an exterior surface of the heart 1. In some cases, the pad 30 can be positioned over and/or adjacent to the pericardium. For example, the proximal end 24 can be coupled to a pad 30 on and in contact with the pericardium to facilitate anchoring the proximal end 24 to the target location within the apex region 19 and maintain desired tension in the tether 20. In some cases, the pad 30 can be positioned within, over and/or adjacent to a layer of the heart wall 17, such as the myocardium or epicardium.

The pad 30 can be positioned over the opening 40 formed in the heart wall 17. For example, the tether 20 can extend through the opening 40 and coupled to the pad 30. The opening 40 can be closed and/or sealed and the pad 30 can be positioned at least partially over the closed and/or sealed opening 40 to anchor the proximal end 24 of the tether 20. Surgical instrumentation can be advanced and/or retracted through, and/or positioned within the opening 40 for a surgical procedure. For example, an introducer instrument can be positioned through the opening 40 formed in the heart wall 17 during a mitral valve repair procedure to facilitate deployment of the tether 20 to the mitral valve leaflet.

Traditionally, one or more purse-string sutures can be stitched around an opening, such as an opening formed in the heart wall, to close the opening. A purse-string suture can be formed in the target tissue to surround the opening such that the purse-string suture can be tensioned to reduce the size of the opening. The size of the opening can be reduced to close the opening around any surgical instruments extending through the opening during a procedure to provide hemostasis. As described herein, more than one tether can be deployed to the mitral valve leaflet. The purse-string suture can be tensioned to close the opening around any surgical instrumentation and one or more deployed tethers during a procedure, such as while one or more additional tethers are deployed. After completion of the procedure, the purse-string suture can be tensioned to seal the opening. In some examples, the purse-string suture can be used to close the opening around the one or more tethers extending therethrough.

Pads typically used for anchoring one or more tethers to a portion of the heart wall can be prone to damage and/or deformation. These pads may have insufficient mechanical strength to withstand forces exerted thereupon by the tethers. For example, these pads can be susceptible to indentation due to forces exerted thereupon by the tethers. Damage and/or deformation of the pads can contribute to migration of the pads through heart wall tissue, reduced tension maintained in the tethers and/or tethering failure.

Described herein are systems, devices and methods relating to a surgical pad which can demonstrate improved mechanical strength when coupled to one or more tethers. In some examples, the surgical pad can comprise a flexible pad portion and a plurality of elongate ribs associated with a surface of the flexible pad portion. The plurality of elongate ribs can be configured to provide mechanical reinforcement for the flexible pad portion so as to reduce or eliminate undesired deformation of the flexible pad portion. In some examples, the flexible pad portion can have a circular or substantially circular shape. In some examples, the plurality of elongate ribs can comprise cylindrical rods.

The surgical pad can be positioned over an opening in a target tissue, and can be coupled to one or more tethers extending through the opening in the target tissue. For example, the opening can be formed in the left ventricular heart wall, and a plurality of tethers can be coupled to one or more mitral valve leaflets. The opening can be closed around the plurality of tethers extending therethrough and the tethers can be coupled to the surgical pad positioned at least partially over the opening. A first surface of the flexible pad portion can be oriented toward the target tissue and the plurality of elongate ribs can be associated with a second surface of the flexible pad portion oriented away from the target tissue. The plurality of elongate ribs can be positioned at least partially over the second surface. In some examples, the plurality of elongate ribs can be positioned on and in contact with the second surface and coupled to the flexible pad portion. The plurality of tethers can be coupled to the flexible pad portion at a plurality of predetermined designated locations. A designated location can comprise a pattern and/or marker on the second surface which can indicate to a surgeon or operator a location at which a tether can be threaded through the flexible pad portion. In some examples, the plurality of tethers can comprise a plurality of pairs of tethers. Each pair of tethers can be configured to be coupled to a corresponding one of the designated locations.

The pattern in which the plurality of elongate ribs is arranged on the second surface and/or the positions of the plurality of designated locations can be selected to provide desired distribution of forces exerted thereupon by the tethers across the flexible pad portion. In some examples, the pattern of arrangement for the elongate ribs and the positions of the plurality of designated locations can be selected to more evenly distribute the forces across the flexible pad portion. Improved distribution of forces across the flexible pad portion can reduce or eliminate undesired deformation of the surgical pad.

The plurality of elongate ribs can be evenly distributed across the second surface. In some examples, the plurality of elongate ribs can be in a radial pattern on the second surface, extending radially outward from a center portion of the second surface. For example, the surgical pad can comprise three, four, six or eight elongate ribs on the second surface in an evenly distributed radially-extending pattern. In some examples, the plurality of elongate ribs can be parallel to one another on the second surface. The surgical pad can comprise three, four, six or eight elongate ribs parallel or substantially parallel to and evenly spaced from one another on the second surface.

In some examples, the plurality of designated locations can be at evenly spaced positions in a circular or substantially circular pattern on the second surface. The plurality of designated locations can be evenly distributed around an edge portion of the second surface of the flexible pad portion. In some examples, the plurality of designated locations on an edge portion of the second surface between a distal end of one or more of the plurality of elongate ribs and an edge of the flexible pad portion and/or on the edge portion between distal ends of neighboring elongate ribs.

In some examples, each of the plurality of elongate ribs can be hollow, comprising a lumen extending therethrough. Each of a plurality of tethers or pairs of tethers can be extended through the flexible pad portion at a corresponding one of the plurality of designated locations, and through a lumen of a corresponding one of the plurality of elongate ribs from a first end to a second end of the elongate rib. For example, a surgical pad comprising a plurality of elongate ribs in a radial pattern can be configured to receive a plurality of tethers or pairs of tethers at the designated locations and the tethers or pairs of tethers can be threaded through lumens of corresponding elongate ribs such that the tethers or pairs of tethers extend out from an end of the elongate ribs at a center portion of the second surface. In some examples, the plurality of tethers or pairs of tethers can be secured to the flexible pad portion at the center portion.

The surgical pad can provide desired interaction with a target tissue to promote integration with the target tissue. The plurality of elongate ribs can demonstrate desired biocompatibility and mechanical strength. The flexible pad portion and/or plurality of elongate ribs can be made from a variety of biocompatible and/or biodegradable materials.

Tensioning of traditional purse-string sutures to close an opening can result in damage to portions of tethers extending through the opening, resulting in abrasive damage to and/or breakage of the tethers. Tensioning of traditional purse-string sutures can cause undesired folding of the tissue proximate and/or adjacent to the opening. The undesired folding of the tissue can in turn result in concentrated loading on portions of the tethers proximate to and/or extending through the opening, leading to damage and/or breakage of the tethers. Tensioning of traditional purse-string sutures may result in the purse-string sutures cutting through the tissue. Movement of the purse-string sutures through the tissue can result in contact between the tethers and the purse-string sutures, thereby leading to damage and/or breakage of the tethers.

Described herein are systems, devices and methods relating to a surgical pad which can be used with an improved pattern of stitching configured to surround an opening formed in a target tissue. The improved pattern of stitching can reduce or eliminate damage to the tethers. In some examples, the improved pattern of stitching can comprise a plurality of anchors deployed into a target tissue in a pattern to surround an opening in the target tissue. A corresponding anchor cord or pair of anchor cords can comprise a distal portion extending at least partially within the target tissue to couple to a respective anchor, and a proximal portion extending from the target tissue. The proximal portions of the plurality of anchor cords can extend externally of the target tissue and in a pattern to surround the opening. Tensioning the anchor cords can cause the opening in the target tissue to close. Described herein are surgical pads that can be used in combination with the plurality of anchor cords to provide desired closing of the openings in target tissues while reducing or eliminating damage to the tethers extending through the openings. The surgical pads can prevent or reduce abrasive damage to the target tissue caused by tensioning the plurality of anchor cords. In some examples, the monolithic structure of the surgical pads can provide added stability to the target tissue adjacent to the opening.

In some examples, a surgical pad configured to be used with the improved pattern of stitching can have a central opening at a center portion of the pad and a plurality of edge openings around an outer edge portion of the pad. While positioned over the target tissue, the central opening can be configured to be aligned with an opening in the target tissue, and allow extension therethrough of surgical instrumentation and/or tethers extending through the opening. In some examples, the plurality of edge openings can be distributed evenly around the outer edge portion. The plurality of edge openings can be in a circular or substantially circular pattern around the outer edge portion of the pad. Each of the plurality of anchor cords or each pair of anchor cords can be extended through a corresponding one of the plurality of edge openings.

Adjusting the tension of one or more surgical cords as described herein after the surgical cords have already been secured to a surgical pad may be difficult. Adjustment in the tension of the surgical cords, such as a tether, may be desired to provide desired heart valve leaflet coaptation. For example, tension in a tether already secured to a surgical pad may be fine-tuned after additional tethers have been deployed to the heart valve and/or secured to the surgical pad to ensure that the heart valve, such as a mitral valve, can properly coapt. Tension in one or more anchor cords can be adjusted after the anchor cords have already been secured to a surgical pad to provide desired closure of an opening in a target tissue. Undoing and/or redoing the coupling mechanism used to secure the surgical cords to the surgical pads may be challenging and/or time consuming, increasing procedure duration and possibly contributing to additional patient trauma. For example, unfastening and/or refastening the coupling mechanism used to secure surgical cords to a surgical pad may be difficult to achieve and/or lead to damage in the surgical cords and/or target tissue. For example, untying a knot used to tie a pair of tethers together so as to secure the pair of tethers and/or a pair of anchor cords to a surgical pad may be difficult to achieve.

Described herein are systems, devices and methods relating to one or more spacers which can be used in combination with a surgical pad, including one or more surgical pads as described herein, to facilitate adjustment in the tension of one or more surgical cords already secured to a surgical pad. As described herein, a surgical pad can be positioned over a target tissue and one or more surgical cords can be secured to the surgical pad. For example, a surgical pad can comprise a pair of tethers or a pair of anchor cords secured thereto. The pair of tethers or pair of anchor cords can be threaded through the surgical pad from a first surface configured to be oriented toward the target tissue to a second surface configured to be oriented away from the target tissue. Respective portions of the pair of tethers or pair of anchor cords can be secured together to one another over the second surface of the surgical pad, such as tied to one another to form a knot over the second surface. In some examples, one or more spacers can be inserted between the surgical pad and the target tissue to facilitate adjustment in tension of the surgical cords. In some examples, the spacer can be positioned such that a first surface can be configured to be adjacent to and in contact with the target tissue and a second surface adjacent to and in contact with the surgical pad. In some examples, one or more spacers can be inserted between the surgical pad and respective portions of the surgical cords positioned over the second surface of the surgical pad. Positioning a spacer between the surgical pad and the target tissue and/or a spacer between the surgical pad and respective portions of the surgical cords can provide a separation between the surgical pad and the target tissue or between the surgical pad and respective portions of the surgical cords, respectively. The separation can add tension to the surgical cords, thereby facilitating adjustment in the tension of the surgical cords without having to redo the coupling of the surgical cords to the surgical pad. In some examples, the spacer can be secured to the target tissue and/or the surgical pad, such as after the spacer has been placed at its desired position.

The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

Although the target tissue is described primarily herein as comprising heart ventricular wall tissue, it will be understood that the target tissue can comprise any number of different types of tissues in the heart and/or in other organs.

In some examples, systems, devices and methods for deploying one or more tethers, as described herein, can comprise one or more features as described in U.S. Patent Application No. 63/014,083, filed Apr. 22, 2020, and entitled "Controlled Suture Tensioning", which is incorporated herein by reference in its entirety for all purposes.

The methods, operations, steps, etc. described herein can be performed on a living animal or on a non-living cadaver, cadaver heart, simulator (e.g., with the body parts, tissue, etc. being simulated), etc. For example, methods for treating a patient include methods for simulating the treatment on a simulated patient or anthropogenic ghost, which can include any combination of physical and virtual elements. Examples of physical elements include human or animal cadavers; any portions thereof, including organ systems, whole organs, or tissue; and manufactured elements, which can simulate the appearance, texture, resistance, or other characteristic. Virtual elements can include visual elements provided on a screen, or projected on a surface or volume, including virtual reality and augmented reality implementations. Virtual elements can also simulate other sensory stimuli, including sound, feel, and/or odor.

Figures 2A, 2B, 2C, 2D:
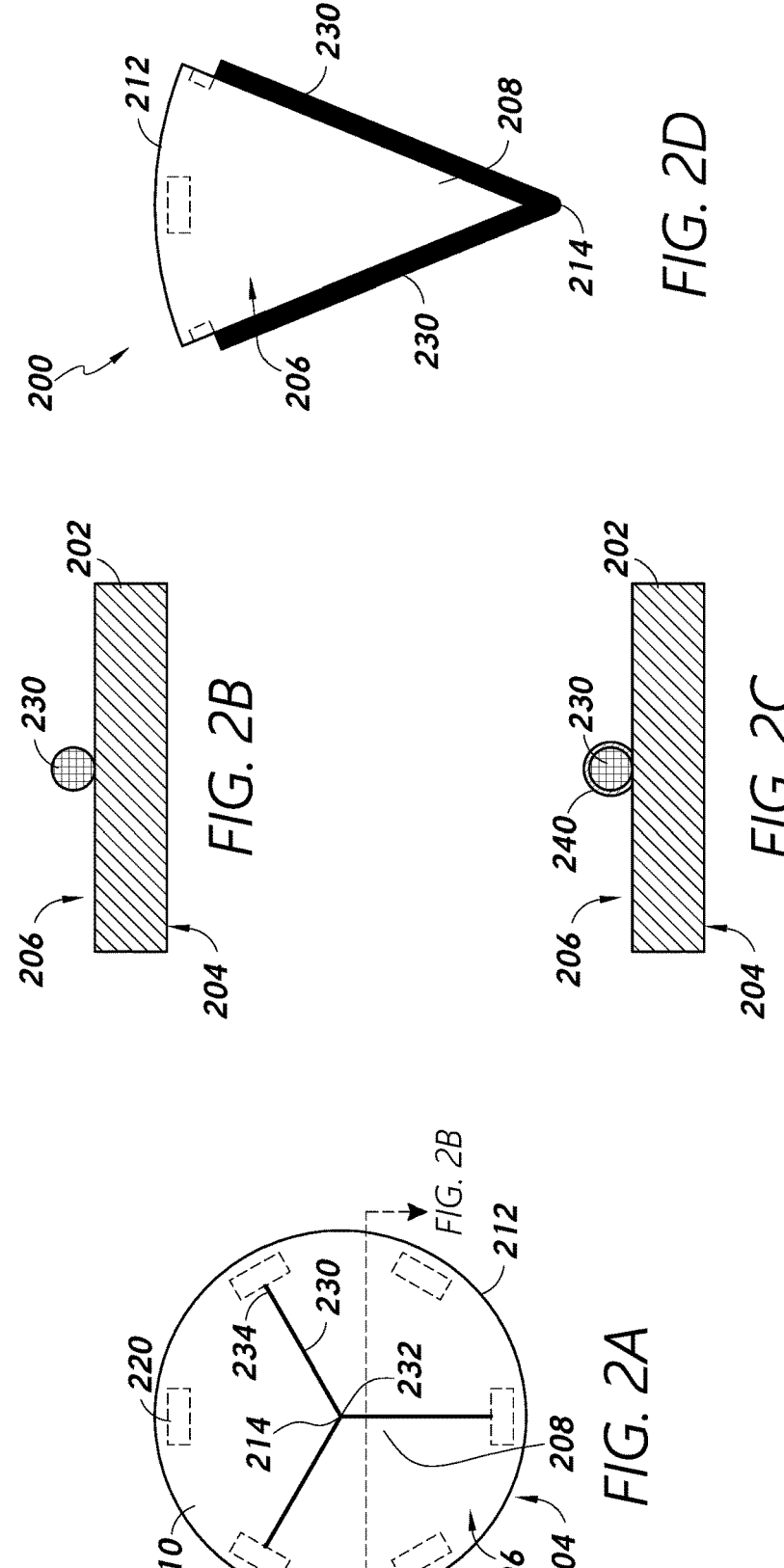
FIG. 2A is a plan view of a surgical pad comprising a plurality of elongate ribs in a radial pattern over a flexible pad portion.
FIG. 2B is a cross-sectional view along the line A-A of the surgical pad of FIG. 2A.
FIG. 2C is a cross-sectional view of the surgical pad along the A-A line of FIG. 2A, where the surgical pad comprises a fastener to couple the elongate rib shown to the flexible pad portion.
FIG. 2D is a side view of the surgical pad of FIG. 2A in a reduced profile state.

FIGS. 2A-2D show examples of a surgical pad 200 comprising a flexible pad portion 202 and a plurality of elongate ribs 230 associated with a second surface 206 of the flexible pad portion 202. The surgical pad 200 can be configured to be positioned over an opening in a target tissue and coupled to a plurality of tethers extending through the opening. The surgical pad 200 can assume an expanded state and a reduced profile state. FIG. 2A is a plan view of the surgical pad 200. The configuration shown in FIG. 2A can be the expanded state. The surgical pad 200 can assume the expanded state at a target site. FIG. 2B is a cross-sectional view of the surgical pad 200 along the line A-A shown in FIG. 2A. FIG. 2C is a cross-sectional view of the surgical pad 200 along the line A-A shown in FIG. 2A, where a fastener 240 is used to couple an elongate rib 230 to the flexible pad portion 202. FIG. 2D is a side view of the surgical pad 200 in a reduced profile state. In some examples, the surgical pad 200 can assume the reduced profile state for transcatheter delivery to the target site.

The surgical pad 200 can be configured to be positioned over a closed opening in a target tissue. For example, the opening can be in a portion of the heart wall, such as in an apex region of a ventricular wall. The flexible pad portion 202 can be configured to be positioned over the opening in the target tissue. For example, at least a portion of the flexible pad portion 202 can be positioned over a closed opening in the target tissue and at least a portion of the flexible pad portion 202 can be positioned over the target tissue adjacent to the closed opening. In some examples, the flexible pad portion 202 can have a circular or substantially circular shape. In other examples, the flexible pad portion 202 can have an oval shape, or a rectangular shape. In the expanded state, the surgical pad 200 can be fully unfolded, for example the flexible pad portion 202 assuming the circular, oval or rectangular shape. The flexible pad portion 202 can have a first surface 204 configured to be oriented toward the target tissue and the second surface 206 can be configured to be oriented away from the target tissue. In some examples, the second surface 206 can be in an opposing orientation relative to the first surface 204. For example, while the surgical pad 200 is positioned over the target tissue, the first surface 204 of the flexible pad portion 202 can be oriented toward the target tissue while the second surface 206 can be oriented in an opposite direction away from the target tissue. The first surface 204 can be positioned on and in contact with the closed opening and the target tissue.

A plurality of tethers can be coupled to the flexible pad portion 202. As described herein, in some examples, each of the plurality of tethers can have a distal end coupled to a heart valve leaflet and a proximal portion extending through the opening in the target tissue. Each of the proximal portions of the tethers can be coupled to the flexible pad portion 202. The second surface 206 of the flexible pad portion 202 can have a plurality of designated locations 220 indicated thereon. A designated location 220 can comprise a pattern and/or marker on the second surface 206 which can indicate to a surgeon or operator a location at which a tether or pair of tethers can be threaded through the flexible pad portion 202. The plurality of designated locations 220 can indicate, such as to an operator or surgeon, where the plurality of tethers can be coupled to the flexible pad portion 202. The plurality of designated locations 220 can comprise a variety of types of indicators. For example, in FIG. 2A, the plurality of designated locations 220 is shown as a plurality of rectangular-shaped markings on the second surface 206. It will be understood that markings having other shapes can be used, including a circle, oval or star shape. In some examples, the plurality of designated locations 220 can comprise a different type of indicator, including a texture and/or an opening in the flexible pad portion. FIG. 2A shows that the second surface 206 can have six designated locations 220. In other examples, the second surface 206 can have another number of designated locations 220.

Each of the plurality of tethers can be coupled to a corresponding designated location 220. In some examples, each designated location 220 can be coupled to a corresponding tether. In some examples, the plurality of tethers can comprise a plurality of pairs of tethers such that each pair of tethers can be coupled to a corresponding designated location 220. For example, each pair of tethers can be coupled to a heart valve leaflet at a distal end and comprise a proximal portion extending through the opening in the target tissue. In some examples, the plurality of designated locations 220 can facilitate identification of each of the pairs of tethers. For example, each pair of tethers can be coupled to a corresponding designated location 220 such that each pair of tethers can be readily separated and/or identified from other pairs of tethers. In some examples, each designated location 220 can comprise an indication of which tether(s) or pair(s) of tethers which can be coupled to the designated location 220. For example, a corresponding designated location 220 and a pair of tethers configured to be coupled to the corresponding designated location 220 can be color coordinated to facilitate identification of where the pair of tethers can be coupled to the flexible pad portion 202. The tethers can be coupled and fixedly secured to the flexible pad portion 202 at the respective designated locations 220. For example, the tethers can be threaded from the first surface 204 through the flexible pad portion 202 to the second surface 206, and then fixedly secured to the flexible pad portion 202. In some examples, the tethers can be knotted over and/or at the designated locations 220 to fixedly secure the tethers to the flexible pad portion 202. Other methods of securing the tethers to the flexible pad portion 202 can also be applicable.

The arrangement of the plurality of designated locations 220 can be selected to provide desired distribution of forces across the surgical pad 200. The positions of the designated locations 220 can be selected such that forces exerted by the plurality of tethers coupled to the flexible pad portion 202 can be evenly distributed thereacross. In some examples, the plurality of designated locations 220 can be at positions on the second surface 206 which form a circular or substantially circular pattern. The plurality of designated locations 220 can be evenly distributed on the second surface 206. In some examples, the plurality of designated locations 220 can be around the outer edge portion 210 of the second surface 206. In some examples, the flexible pad portion 202 can have a circular or substantially circular shape, and the plurality of designated locations 220 can be evenly distributed around the outer edge portion 210 of the second surface 206. Each of the plurality of designated locations 220 can be at the same distance from a nearest portion of the outer edge 212 of the flexible pad portion 202. As described herein, each of the plurality of elongate ribs 230 can comprise a first end 232 and a second end 234, where the first end 232 can be positioned over a center portion 208 of the second surface 206, and the second end 234 can be positioned over the outer edge portion 210 of the second surface 206. As shown in FIG. 2A, some of the designated locations 220 can be on the second surface 206 between a second end 234 of an elongate rib 230 and the outer edge 212 of the flexible pad portion 202. In some examples, some of the designated locations 220 can be on the outer edge portion 210 between two immediately neighboring elongate ribs 230. For example, designated locations 220 of the surgical pad 200 can be on the outer edge portion 210 between the second end 234 of each of the elongate ribs 230 and the outer edge 212, and on the outer edge portion 210 between two immediately neighboring elongate ribs 230. In some examples, designated locations can be either on the outer edge portion between the second ends of at least some, including each, of the elongate ribs and the outer edge, or on the outer edge portion between some, including all, of the two immediately neighboring elongate ribs.

Referring again to FIG. 2A, the plurality of elongate ribs 230 can be disposed on the second surface 206 of the flexible pad portion 202 in a predetermined pattern. The plurality of elongate ribs 230 can be configured to provide mechanical reinforcement for the flexible pad portion 202. The plurality of elongate ribs 230 can comprise a rigid and/or semi-rigid material configured to mechanically reinforce the flexible pad portion 202 to counter forces exerted thereupon by the plurality of tethers or pairs of tethers coupled thereto. The plurality of elongate ribs 230 can provide additional mechanical strength for the flexible pad portion 202 to reduce or eliminate undesired deformation of the flexible pad portion 202. For example, flexible pad portion 202 comprising the plurality of elongate ribs 230 coupled thereto can demonstrate no or reduced undesired indentation toward the heart wall tissue due to forces exerted thereupon by the plurality of tethers. Reduced deformation can prevent undesired migration of the surgical pad 200 through the heart wall tissue and/or failure in the surgical pad 200.

A pattern in which the elongate ribs 230 is positioned over the second surface 206 can be selected to facilitate desired mechanical reinforcement of the flexible pad portion 202. In some examples, the pattern can be predetermined to provide desired distribution of forces exerted upon the surgical pad 200. For example, the pattern can be selected to more evenly distribute the forces exerted upon the surgical pad 200 by the plurality of tethers. In some examples, the elongate ribs 230 can be positioned in a radial pattern on the second surface 206. The elongate ribs 230 can each radially extend from the center portion 208 of the second surface 206 to the outer edge portion 210 of the second surface 206, for example arranged in a radially extending pattern. Each of the elongate ribs 230 can comprise a first end 232 positioned over the center portion 208 and a second end 234 positioned over the outer edge portion 210. In some examples, each of the elongate ribs 230 can have a linear or substantially linear shape. For example, each of the elongate ribs 230 can extend linearly from the first end 232 positioned over the center portion 208 to the second end 234 positioned over the outer edge portion 210.

In some examples, the plurality of elongate ribs 230 can be evenly distributed across the second surface 206. For example, the first ends 232 of the plurality of elongate ribs 230 can be coupled to one another at the center portion 208, such as at a center point 214 of the second surface 206, and the second ends 234 of the plurality of elongate ribs 230 can be evenly spaced from one another around the outer edge portion 210 of the second surface 206. Each of the plurality of elongate ribs 230 can be linear or substantially linear such that each of the elongate ribs 230 can be evenly spaced from immediately neighboring ribs along a length of each of the elongate ribs 230. In some examples, coupling the first ends 232 of the plurality of elongate ribs 230 to one another can provide improved mechanical reinforcement of the flexible pad portion 202. As described in further detail herein, in some examples, the first ends 232 of the plurality of elongate ribs 230 may not be coupled to one another.

FIG. 2A shows three elongate ribs 230 over the second surface 206. It will be understood that the surgical pad 200 can include another number of elongate ribs 230. In some examples, the surgical pad 200 can have three, four, six or eight elongate ribs 230.

The plurality of elongate ribs 230 can be made of a variety of biocompatible and/or biodegradable materials. In some examples, the plurality of elongate ribs 230 can comprise a metallic and/or polymeric material. In some examples, the plurality of elongate ribs 230 can comprise a metallic alloy. In some examples, the plurality of elongate ribs 230 may not be biodegradable. In some examples, the plurality of elongate ribs 230 can comprise one or more of a cobalt-chromium alloy, a nickel-titanium alloy (e.g., nitinol), platinum, and tantalum. In some examples, the plurality of elongate ribs 230 can be biodegradable. In some examples, the plurality of elongate ribs 230 can comprise a metallic alloy comprising magnesium, iron and/or zinc. In some examples, the plurality of elongate ribs 230 can comprise polylactic acid, polyanhydrides and/or polyesters. Biodegradable elongate ribs can be configured to provide sufficient mechanical strength for a desired period of time prior to degradation, such as to maintain the structural integrity of the flexible pad portion.

The flexible pad portion 202 can comprise any number of biocompatible materials and/or biodegradable materials. In some examples, the flexible pad portion 202 can comprise a material configured to facilitate tissue integration into the target tissue. In some examples, the flexible pad portion 202 can comprise non-biodegradable material. In some examples, the flexible pad portion 202 can comprise a non-biodegradable tissue, including cross-linked tissue. In some examples, the flexible pad portion 202 can be treated with anti-thrombotic and/or anti-calcification treatments. For example, the flexible pad portion 202 can comprise non-biodegradable material treated with anti-thrombotic and/or anti-calcification treatments. In some examples, the flexible pad portion 202 can comprise bovine tissue, including bovine pericardial tissue. The bovine tissue can be cross-linked bovine tissue. The bovine tissue and/or bovine pericardial tissue can be treated with anti-thrombotic and/or anti-calcification treatments. In some examples, the flexible pad portion 202 can comprise non-degradable polymeric material. In some examples, the flexible pad portion 202 can comprise biodegradable material, such as decellularized tissue. For example, the flexible pad portion 202 can comprise non-crosslinked decellularized biological material that can degrade and promote integration into the target tissue. In some examples, a plurality of biodegradable elongate ribs can be associated with a biodegradable flexible pad portion. In some examples, a plurality of non-degradable elongate ribs can be associated with a non-degradable flexible pad portion.

As described herein, in some examples, the opening in the target tissue can be formed in the heart wall, such as a ventricular portion of the heart wall. In some examples, the surgical pad 200 can be positioned over a pericardial layer of the heart. For example, the surgical pad 200 can be disposed on and in contact with the pericardium. In some examples, the flexible pad portion 202 and/or plurality of elongate ribs 230 can comprise material configured to promote integration with the pericardium. In some examples, the flexible pad portion 202 and/or the plurality of elongate ribs 230 can comprise material configured to biodegrade after deployment to a target position over the pericardium. In some examples, the surgical pad 200 can be configured to be positioned over the epicardium. In some examples, the flexible pad portion 202 and/or plurality of elongate ribs 230 can comprise material configured to promote integration with the epicardium. In some examples, the flexible pad portion 202 and/or plurality of elongate ribs 230 can comprise material configured to biodegrade after deployment to a target position over the epicardium.

FIG. 2B is a cross-sectional view of the surgical pad 200 along the line A-A shown in FIG. 2A. The cross-sectional view shows a cross section of the flexible pad portion 202 and one of the elongate ribs 230. The cross-sectional view is along a lateral axis perpendicular or substantially perpendicular to a longitudinal axis of the elongate rib 230. The elongate rib 230 can have a circular or substantially circular cross section. For example, each of the elongate ribs 230 can have a cylindrical or substantially cylindrical shape. In some examples, the elongate rib 230 can be solid. For example, each of the plurality of elongate ribs 230 can be a solid cylindrical or substantially cylindrical rod.

The plurality of elongate ribs 230 can be coupled to the flexible pad portion 202 in a variety of manners. In some examples, each elongate rib 230 can be glued, and/or fastened to the flexible pad portion 202. FIG. 2C is a cross-sectional view of the surgical pad 200 comprising a fastener 240 to secure the elongate rib 230 to the flexible pad portion 202. In some examples, the fastener 240 can comprise a suture. In some examples, the fastener 240 can be integral with the flexible pad portion 202. The fastener 240 can comprise one or more extensions configured to couple the elongate ribs 230 to the flexible pad portion 202. For example, the fastener 240 can comprise one or more loops integral with the flexible pad portion 202 through which a corresponding portion of the elongate rib 230 can be inserted. The elongate rib 230 can be positioned between the fastener 240 and the second surface 206. It will be understood that the elongate rib 230 can be coupled to the flexible pad portion 202 via one or more than one mechanisms, such as both glued and fastened to the flexible pad portion 202.

In some examples, the surgical pad 200 can assume a lower profile configuration to facilitate transcatheter delivery to the target site. FIG. 2D shows an example of a side view of the surgical pad 200 in a lower profile configuration. For example, the surgical pad 200 can be at least partially folded and assume a reduced profile state for ease of placement within a delivery catheter for transcatheter delivery. The surgical pad 200 can assume an expanded state, such as the state shown in FIG. 2A, after deployment from the delivery catheter at or proximate to the target site. In the expanded state, the surgical pad 200 can be fully unfolded. In the reduced profile state, the surgical pad 200 can comprise one or more folds. For example, the flexible pad portion 202 can comprise one or more folds while the surgical pad 200 is in the reduced profile state. The flexible pad portion 202 can comprise a fold along and/or adjacent to at least one or more of the elongate ribs 230. In the folded state, the first ends 232 of the plurality of elongate ribs 230 can be oriented in a first direction and the second ends 234 of the plurality of elongate ribs 230 can be oriented in a second direction. In some examples, the first ends 232 and the second ends 234 can be in opposing or substantially opposing directions when the surgical pad 200 is in the reduced profile state, including when the surgical pad 200 is positioned within a delivery catheter. In some examples, while positioned within the delivery catheter during delivery, the first ends 232 can be configured to be oriented proximally or substantially proximally and the second ends 234 can be configured to be oriented distally or substantially distally, or vice versa. In the configuration shown in FIG. 2D, the flexible pad portion 202 can be folded such that the second surface 206 and the plurality of elongate ribs 230 is outward facing. The flexible pad portion 202 can be folded such that the center point 214 forms a point. In the configuration shown in FIG. 2D, a third or about a third of the second surface 206 is shown. In some examples, the surgical pad 200 can assume an umbrella configuration in the reduced profile state. It will be understood that the reduced profile state shown in FIG. 2D is for illustrative purposes only and that the surgical pad 200 can be folded in other manners to assume the reduced profile state.

Figures 3, 4, 5:
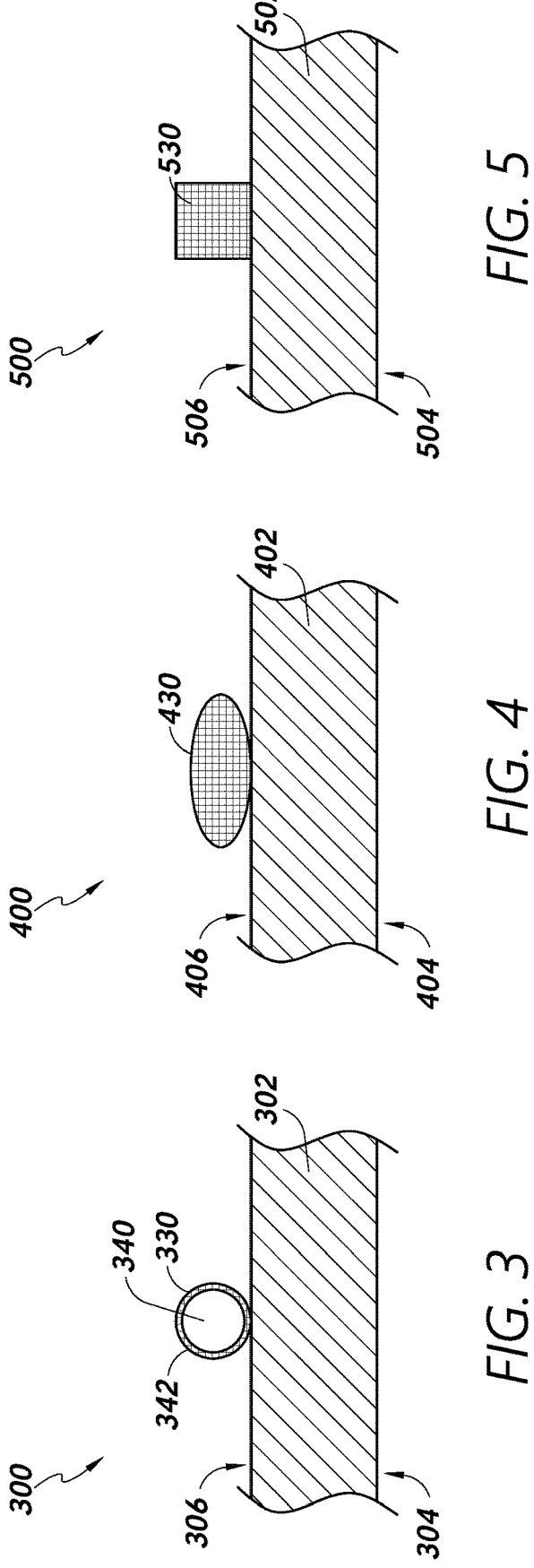
FIG. 3 is a cross-sectional view of an example of a surgical pad which comprises a hollow elongate rib.
FIG. 4 is a cross-sectional view of an example of a surgical pad which comprises an elongate rib having an oval cross-sectional shape.
FIG. 5 is a cross-sectional view of an example of a surgical pad which comprises an elongate rib having a rectangular cross-sectional shape.

FIGS. 3 through 5 show cross-sectional views of examples of surgical pads 300, 400, 500 comprising elongate ribs 330, 430, 530 having different configurations. The cross-sectional views shown in FIGS. 3 through 5 are along a lateral axis perpendicular or substantially perpendicular to a longitudinal axis of the respective elongate ribs 330, 430, 530. Each of the elongate ribs 330, 430, 530 are positioned over respective flexible pad portions 302, 402, 502, where a first surface 304, 404, 504 of each of the flexible pad portions 302, 402, 502 is configured to be oriented toward the target tissue and a second surface 306, 406, 506 is configured to be oriented away from the target tissue. The elongate ribs 330, 430, 530 can be positioned over the respective second surfaces 306, 406, 506. FIG. 3 shows that the elongate rib 330 can be at least partially hollow. In some examples, a hollow or partially hollow elongate rib can provide desired physical strength for mechanical reinforcement of a surgical pad while reducing the weight and/or increasing the flexibility of the elongate rib, for example thereby easing delivery of the surgical pad to the target site.

In some examples, the elongate rib 330 can comprise a lumen 340 extending therethrough. The lumen 340 can extend along an entire length of the elongate rib 330. As described in further detail herein, in some examples, a tether or pair of tethers configured to be coupled to the flexible pad portion 302 can be extended through the lumen 340. In some examples, extending a tether or pair of tethers through a lumen of each of a plurality of elongate ribs positioned over a flexible pad portion can further improve distribution of forces exerted by the tethers across the flexible pad portion.

Referring again to FIG. 3, in the cross-sectional view shown, an outer wall 342 of the elongate rib 330 and the lumen 340 are shown as having a circular or substantially circular shape. An outer wall of an elongate rib and/or a lumen of the elongate rib can have any number of other cross-sectional shapes, such as an oval shape or a rectangular shape. The outer wall and the lumen may or may not have the same cross-sectional shape. The elongate ribs 430, 530 shown in FIGS. 4 and 5 can be solid and have non-circular cross-sectional shapes. For example, the elongate rib 430 can have an oval cross-sectional shape. An elongate rib having an oval cross-sectional shape can provide desired mechanical strength while reducing a height profile of the surgical pad. The elongate rib 530 can have a rectangular cross-sectional shape, including a square cross-sectional shape. In some examples, an elongate rib having a rectangular cross-sectional shape can facilitate coupling of the elongate rib to a flexible pad portion, such as providing increased contact surface area between the elongate rib and the flexible pad portion.

Each of the surgical pads 300, 400, 500 can have one or more other features of the surgical pad 200 described with reference to FIG. 2.

FIGS. 6 through 8 show plan views of various examples of surgical pads 600, 700, 800, each comprising a different number of elongate ribs 630, 730, 830. Each of the surgical pads 600, 700, 800 can have a respective flexible pad portion 602 702, 802. Each of the flexible pad portions 602, 702, 802 can have one or more features of the flexible pad portion 202 described with reference to FIG. 2. For example, the flexible pad portions 602, 702, 802 can have a first surface 604, 704, 804 configured to be oriented toward the target tissue and/or the closed opening in the target tissue, and a second surface 606, 706, 806 configured to be oriented in an opposing direction away from the target tissue and/or opening. The elongate ribs 630, 730, 830 can be in a radial pattern over respective second surfaces 606, 706, 806 of the flexible pad portions 602, 702, 802. The surgical pad 600 of FIG. 6 is shown as having four elongate ribs 630 arranged in a radial pattern on the second surface 606 of the flexible pad portion 602. The surgical pad 700 of FIG. 7 is shown as having six elongate ribs 730 arranged in a radial pattern on the second surface 706 of the flexible pad portion 702, while the surgical pad 800 of FIG. 8 is shown as having eight elongate ribs 830 arranged in a radial pattern on the second surface 806 of the flexible pad portion 802. The plurality of elongate ribs 630, 730, 830 can each comprise a first end 632, 732, 832 and a second end 634, 734, 834. The first ends 632, 732, 832 can be oriented toward and coupled to one another over a center portion 608, 708, 808 of the respective second surfaces 606, 706, 806. The second ends 634, 734, 834 can be positioned around an outer edge portion 610, 710, 810 of the respective second surfaces 606, 706, 806. Each of the elongate ribs 630, 730, 830 can be a cylindrical rod.

The elongate ribs 630, 730, 830 can be evenly distributed across the second surfaces 606, 706, 806. For example, the first ends 632, 732, 832 can meet and be coupled to one another at respective centers 614, 714, 814 of the second surfaces 606, 706, 806, while the second ends 634, 734, 834 can be evenly spaced around the respective outer edge portions 610, 710, 810. In some examples, the elongate ribs 630, 730, 830 can be linear or substantially linear such that the elongate ribs 630, 730, 830 are equally spaced from an immediately neighboring elongate rib along a length of the elongate rib. As described in further detail herein, alternatively, first ends of elongate ribs arranged in a radial pattern may not be coupled to one another.

The surgical pads 600, 700, 800 can each have a plurality of designated locations 620, 720, 820 around respective outer edge portions 610, 710, 810 of the second surfaces 606, 706, 806. The designated locations 620, 720, 820 can be evenly distributed around the outer edge portions 610, 710, 810 and each of the plurality of designated locations 620, 720, 820 can be at the same distance from a nearest portion of the respective outer edge 612, 712, 812. As shown in FIG. 6, the surgical pad 600 can have a designated location 620 on the outer edge portion 610 between each of the second ends 634 of the elongate ribs 630 and the outer edge 612 and a designated location 620 on the outer edge portion 610 between two immediately neighboring elongate ribs 630. For example, the surgical pad 600 can have eight designated locations 620. As shown in FIGS. 7 and 8, the surgical pads 700, 800 can have a designated location 720, 820 on respective outer edge portions 710, 810 between each of the second ends 734, 834 of the elongate ribs 730, 830 and the respective outer edges 712, 812 and no designated locations between two neighboring elongate ribs 730, 830. The surgical pad 700 is shown as having six designated locations 720 while the surgical pad 800 is shown as having eight designated locations 820. It will be understood that the surgical pads 600, 700, 800 can have more or fewer designated locations than as shown. For example, the surgical pad 600 may not have designated locations 620 between neighboring elongate ribs 630. In some examples, the surgical pads 700, 800 of FIGS. 7 and 8 may have designated locations 720, 820 between immediately neighboring elongate ribs 730, 830. In some examples, a designated location may not be present between every second end of an elongate rib and an outer edge. In some examples, a designated location can be between alternating pairs of immediately neighboring elongate ribs.

FIG. 9 is a plan view of an example of a surgical pad 900 comprising three elongate ribs 930 arranged in a radial pattern over a second surface 906 of a flexible pad portion

902, where the three elongate ribs 930 are not coupled to one another. The first ends 932 of each of the elongate ribs 930 are oriented toward one another but not are not coupled to one another. For example, the first ends 932 can be positioned over a center portion 908 of the second surface 906 without being coupled to one another. The second ends 934 can be evenly spaced around the outer edge portion 910. In some examples, having first ends 932 not coupled to one another can facilitate folding of the surgical pad 900, such as to ease delivery of the surgical pad 900 to a target site in a reduced profile state.

The surgical pad 900 can have a designated location 920 on the outer edge portion 910 between each of the second ends 934 of the elongate ribs 930 and the outer edge 912 and a designated location 920 on the outer edge portion 910 between two immediately neighboring elongate ribs 930. For example, the surgical pad 900 can have six designated locations 920.

In some examples, the three elongate ribs 930 can be hollow, for example each comprising a lumen extending therethrough. In some examples, the plurality of tethers configured to be coupled to the surgical pad 900 can be threaded through a lumen of one or more of the elongate ribs 930. For example, a first surface 904 of the flexible pad portion 902 can be oriented toward a target tissue and the second surface 906 can be oriented away from the target tissue, and a tether or pair of tethers extending from the opening can be threaded through from the first surface 904 of the flexible pad portion 902 to the second surface 906. The tether or pair of tethers can then be advanced through a lumen of an elongate rib 930 from the second end 934 to the first end 932 of the elongate rib 930. In some examples, the tether or pair of tethers can be threaded through the flexible pad portion 902 at or proximate to the location where the second end 934 is positioned over the flexible pad portion 902. The tether or pair of tethers can then be extended out from the first end 932 of the elongate rib 930. The tether or pair of tethers can then be fixedly coupled to the surgical pad 900 at or adjacent to the first end 932 of the elongate rib 930. For example, the tether or pair of tethers can be fixedly coupled to the surgical pad 900 over and/or at the center portion 908 of the second surface 906. In some examples, all of the tethers or pairs of tethers coupled to the surgical pad 900 can be knotted together with one another over and/or at the center portion 908 of the second surface 906. In some examples, the plurality of tethers or pairs of tethers can be fixedly secured to a corresponding designated location 920, and are not threaded through lumens of the elongate ribs 930.

In some examples, threading a plurality of tethers through the lumens of the elongate ribs can improve coupling of the tethers to the surgical pad. In some examples, threading the plurality of tethers through the lumen of the elongate ribs can improve distribution of forces exerted upon the surgical pad by the tethers, thereby reducing undesired indentation of the surgical pad.

Figure 10B:
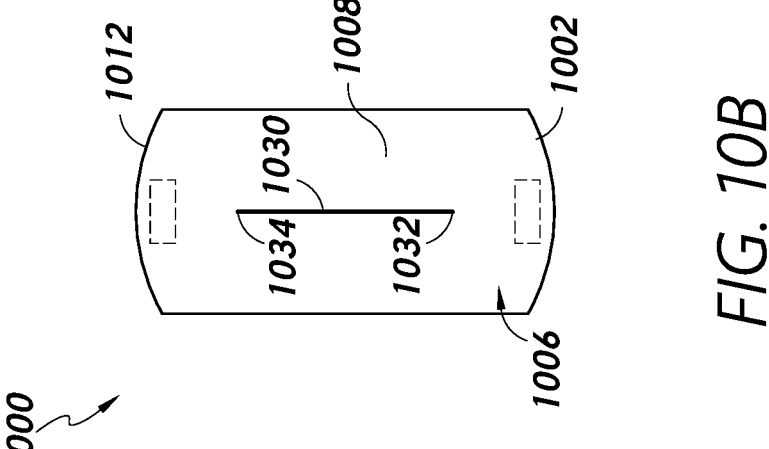
FIG. 10B is a side view of the surgical pad of FIG. 10A in a reduced profile state.
Figure 10A:
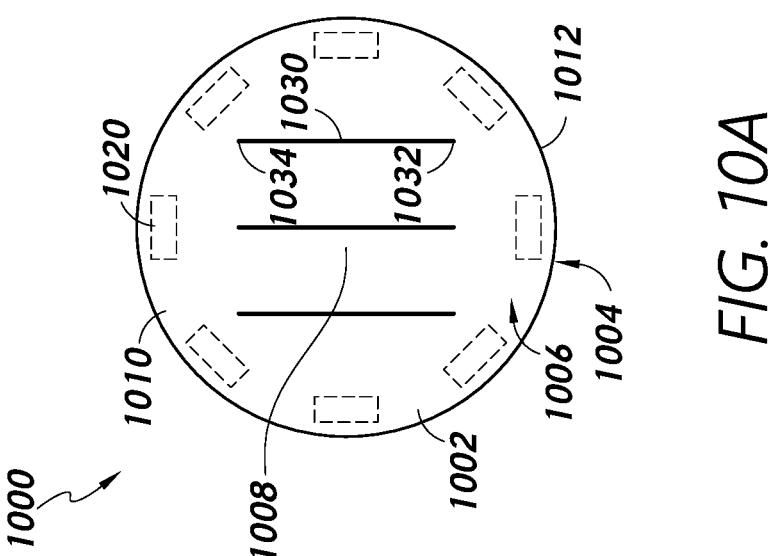
FIG. 10A is a plan view of an example of a surgical pad comprising a plurality of elongate ribs in a parallel pattern over a flexible pad portion.

FIG. 10A is a plan view of an example of a surgical pad 1000 comprising three elongate ribs 1030 which are positioned parallel or substantially parallel to one another over a second surface 1006 of a flexible pad portion 1002. The flexible pad portion 1002 can have a circular or substantially circular shape. The second surface 1006 can be configured to be oriented away from the target tissue. The flexible pad portion 1002 can comprise a first surface 1004 configured to be oriented toward the target tissue. For example, the first surface 1004 and the second surface 1006 can have opposing orientations. In some examples, each of the plurality of elongate ribs 1030 can be evenly distributed across the second surface 1006. Each of the plurality of elongate ribs 1030 can be equidistant or substantially equidistant from immediately neighboring elongate ribs 1030.

The first ends 1032 of each of the elongate ribs 1030 can be oriented in one direction and the second ends 1034 are oriented in a second direction. Each of the elongate ribs 1030 can be linear or substantially linear such that the second ends 1034 are oriented in a second opposing direction relative to that of the first ends 1032. In some examples, one or more of the elongate ribs 1030 can comprise at least a portion positioned over and extending across a center portion 1008 of the second surface 1006. The surgical pad 1000 can comprise an elongate rib 1030 extending over a diameter of the flexible pad portion 1002. In some examples, the plurality of elongate ribs 1030 can be a plurality of solid cylindrical rods.

The flexible pad portion 1002 can have a plurality of designated locations 1020 around an outer edge portion 1010 of the second surface 1006. The plurality of designated locations 1020 can be at the same distance from a nearest portion of the outer edge 1012 of the flexible pad portion 1002. In some examples, the plurality of designated locations 1020 can be evenly distributed around the outer edge portion 1010. FIG. 10A shows eight designated locations 1020. It will be understood that the surgical pad 1000 can have more or fewer designated locations 1020.

FIG. 10B is a side view of the surgical pad 1000 in a reduced profile state. The surgical pad 1000 can comprise one or more folds in the reduced profile state. The surgical pad 1000 can have one or more folds along a direction parallel or substantially parallel to the elongate ribs 1030. In the reduced profile state the surgical pad 1000 can have an elongate configuration. For example, the flexible pad portion 1002 can be folded along a direction parallel or substantially parallel to the elongate ribs 1030 to divide the flexible pad portion 1002 into equally or substantially equally wide portions, including three equally portions. FIG. 10B shows a portion of the second surface 1006 comprising an elongate rib 1030 and two designated locations 1020 at opposing positions. It will be understood that the flexible pad portion 1002 can be folded to divide the surgical pad 1000 into a different number of portions to provide the elongate configuration in the reduced profile state. In some examples, during delivery to a target site, the elongate ribs 1030 can be parallel or substantially parallel to a longitudinal axis of a delivery catheter such that the first ends 1032 can be oriented proximally and the second ends 1034 can be oriented distally, or vice versa.

FIG. 11 is a process flow diagram showing an example of a deployment process 1100 for deploying one or more surgical pads as described herein. The surgical pads can comprise a flexible pad portion comprising a first surface and a second surface, the second surface comprising a plurality of elongate ribs associated therewith. In block 1102, the deployment process 1100 involves providing the flexible pad portion and the plurality of elongate ribs associated with the second surface. The plurality of elongate ribs can be in contact with and coupled to the second surface of the flexible pad portion. The surgical pad can be provided in an expanded state. For example, the flexible pad portion can be fully unfolded in the expanded state. In block 1104, the deployment process 1100 involves positioning the flexible pad portion over an opening in a target tissue to orient the first surface toward the target tissue and the second surface away from the target tissue. The opening can be closed. The flexible pad portion can be positioned on and in contact with the target tissue. In some examples, the flexible pad portion can be positioned over the closed opening and the target tissue. In some examples, positioning the flexible pad portion over the opening in the target tissue can comprise positioning the flexible pad portion over an opening in a heart wall.

A plurality of tethers can be extending through the opening, for example the opening being closed around the tethers. In block 1106, the deployment process 1100 involves threading each of the plurality of tethers extending from the opening in the target tissue through the flexible pad portion at a corresponding designated location of a plurality of designated locations around an outer edge portion of the second surface. In block 1108, the deployment process 1100 involves securing the plurality of tethers to the flexible pad portion.

As described herein, the plurality of tethers can comprise a plurality of pairs of tethers. In some examples, each of the plurality of tethers or plurality of pairs of tethers can be secured to the corresponding designated location. In some examples, securing the plurality of tethers to the flexible pad portion comprises tying a suture knot over the second surface of the flexible pad portion. For example, each of the plurality of tethers or plurality of pairs of tethers can be threaded through the flexible pad portion from the first surface to the second surface at the corresponding designated location. The tethers can then be knotted to secure the tethers to the corresponding designated locations. In some examples, each pair of tethers can be knotted together. As described herein, the opening in the target tissue can be on the ventricular heart wall. The tethers or pairs of tethers can be coupled to a heart valve leaflet such that threading the plurality of tethers through the flexible pad portion can comprise coupling one or more locations on the heart valve leaflet to the flexible pad portion at a corresponding designated location.

In some examples, each of the plurality of elongate ribs can comprise a lumen extending therethrough. The lumen can extend from a first end to a second end of an elongate rib. Deploying the surgical pad can comprise threading the plurality of tethers or plurality of pairs of tethers through the lumens of respective elongate ribs after threading the plurality of tethers or plurality of pairs of tethers through the flexible pad portion from the first surface to the second surface at the corresponding designated locations. For example, the plurality of elongate ribs can be positioned in a radial pattern over the second surface of the flexible pad portion, the first end of each of the plurality of elongate ribs being at a center portion of the second surface and the second end of each of the plurality of elongate ribs being at an outer edge portion of the second surface. Each of the plurality of tethers or plurality of pairs of tethers can be threaded through a lumen of a corresponding elongate rib from the second end to the first end. Each of the plurality of tethers or pairs of tethers can be extended out from the first end. Securing the tethers to the flexible pad portion can comprise, for example, tying a knot over the center portion of the second surface using each of the plurality of tethers or each pair of tethers.

In some examples, deploying the surgical pad can comprise transporting the surgical pad in a reduced profile state to the target tissue using a transcatheter delivery approach. The reduced profile state can comprise a folded surgical pad. The flexible pad portion can comprise one or more folds in the reduced profile state. For example, the flexible pad portion can be folded such that first ends of the plurality of elongate ribs can be oriented in a first direction and second ends of the plurality of elongate ribs can be oriented in a second direction, including a direction opposite that of the first direction. In some examples, the surgical pad can be folded into an umbrella configuration in the reduced profile state. In some examples, the surgical pad can be folded into an elongate configuration in the reduced profile state. The surgical pad can transform from the reduced profile state to the expanded state at or proximate to the target site. The surgical pad can unfold at or proximate to the target site to change to a fully unfolded configuration in the expanded state. For example, the flexible pad portion can fully unfold to assume the expanded state.

As described herein, tensioning of traditional purse-string sutures to close an opening in a target tissue can result in damage to portions of tethers extending through the opening, resulting in abrasive damage to and/or breakage of the tethers. Tensioning of traditional purse-string sutures can cause undesired folding of the tissue proximate and/or adjacent to the opening, which can result in concentrated loading on portions of the tethers proximate to and/or extending through the opening. Tensioning of traditional purse-string sutures can cause movement of the purse-string sutures through the tissue, which may lead to contact between the tethers and the purse-string sutures. Concentrated loading on the tethers and/or contact between the purse-string sutures and the tethers can result in damage and/or breakage of the tethers.

An improved pattern of stitching can reduce or eliminate damage to the tethers. In some examples, the improved pattern of stitching can comprise a plurality of anchors deployed into a target tissue in a pattern to surround an opening in the target tissue. A corresponding anchor cord or pair of anchor cords can comprise a distal portion extending at least partially within the target tissue, a distal end being coupled to a respective anchor, and a proximal portion extending from the target tissue. The proximal portions of the plurality of anchor cords can extend from the target tissue and in a pattern to surround the opening and the anchor cords can be tensioned to close the opening. Described herein are surgical pads which can be used in combination with the plurality of anchor cords to provide desired closing of the openings in target tissues while reducing or eliminating damage to the tethers extending through the openings.

Figures 12A, 12B:
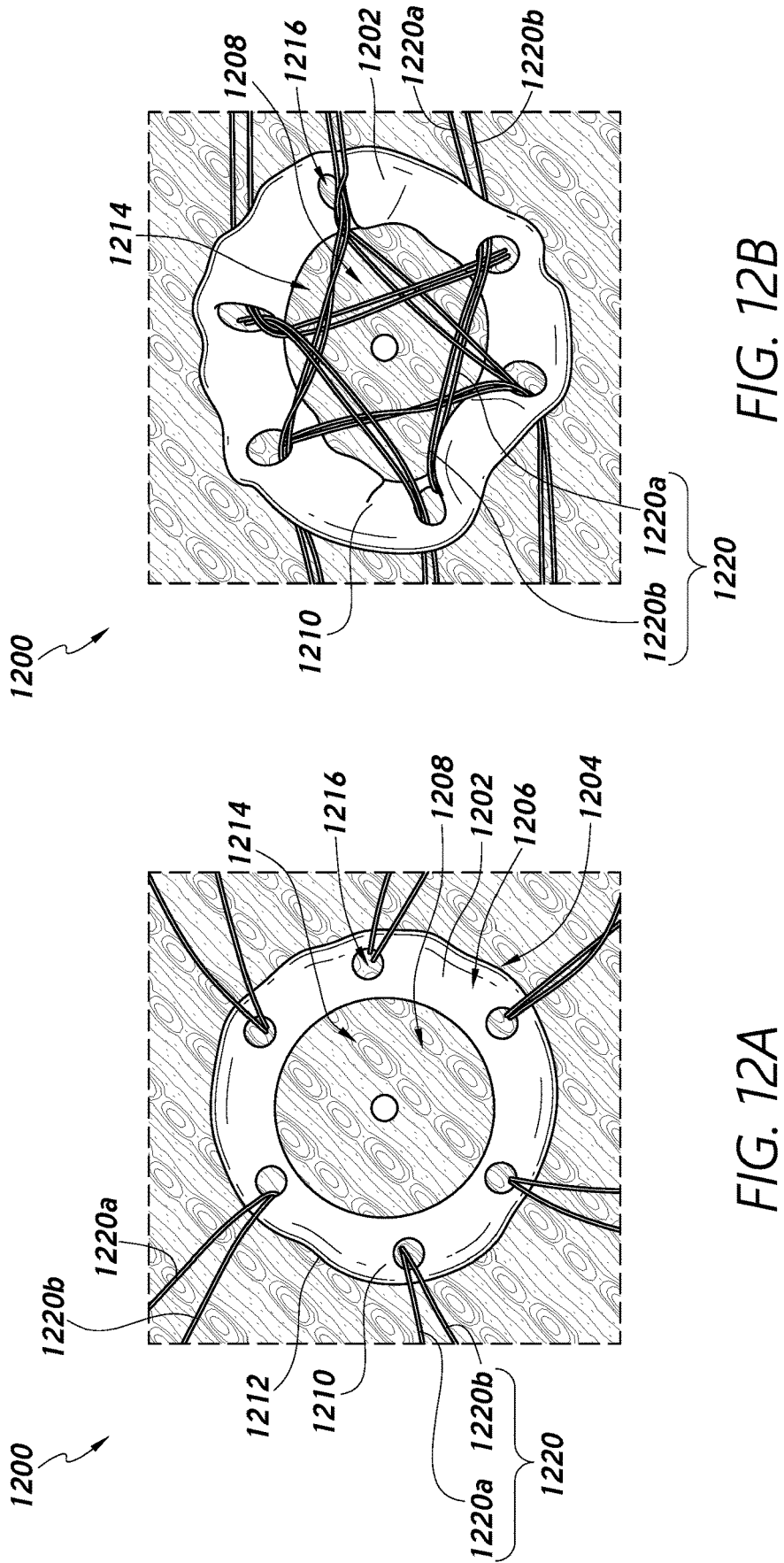
FIG. 12A is a plan view of an example of a suture system comprising a surgical pad and a plurality of anchor cords.
FIGS. 12B and 12C show different arrangements of the anchor cords to facilitate desired tensioning of the anchor cords.

FIGS. 12A through 12D show various views of a suture system 1200 comprising a surgical pad 1202 and a plurality of anchor cords 1220. As described in further detail herein, the plurality of anchor cords 1220 can be coupled to a respective plurality of anchors deployed into the tissue. Referring to FIG. 12A, the surgical pad 1202 can have a central opening 1214 at a center portion 1208 of the surgical pad 1202 and a plurality of edge openings 1216 distributed around an outer edge portion 1210 of the surgical pad 1202. The surgical pad 1202 can be positioned over a target tissue, a first surface 1204 of the surgical pad 1202 being configured to be oriented toward the target tissue and a second surface 1206 of the surgical pad 1202 being configured to be oriented away from the target tissue. While positioned over the target tissue, the central opening 1214 can be configured to be aligned with an opening in the target tissue. In some examples, the opening in the target tissue can be configured to allow extension therethrough of surgical instrumentation. In some examples, the opening can be on a portion of a ventricular heart wall and can be configured to allow extension therethrough of a plurality of tethers coupled to one or more heart valve leaflets.

Use of a surgical pad in combination with a plurality of anchor cords can provide a physical barrier between the target tissue and the plurality of anchor cords. The surgical pad can prevent or reduce abrasion of the target tissue due to the anchor cords. In some examples, having the plurality of anchor cords extending through one surgical pad, rather than a plurality of pads, can provide improved stabilization of the surgical area surrounding the opening in the target tissue, and/or simplify the surgical procedure by using fewer components. The monolithic configuration of the surgical pad can provide added structure to the target tissue adjacent to the opening, adding stability to the area of tissue.

In some examples, the plurality of anchor cords, and/or the anchors coupled thereto, can be pre-threaded through the surgical pad prior to deployment of the anchor cords and/or anchors. In some examples, the monolithic structure of the surgical pad can provide guidance in the deployment of the plurality of anchor cords and anchors. The plurality of anchors can be coupled to respective anchor cords, and the anchor cords can be threaded through respective edge openings prior to deploying the plurality of anchors and anchor cords into the target tissue such that the positions of the edge openings can determine the positions of the anchors and anchor cords. In some examples, the plurality of anchor cords and anchors can be deployed into the target tissue through the respective edge openings of the surgical pad such that the positions of the edge openings can determine the positions of the anchors and anchor cords. For example, the plurality of anchors and anchor cords can be deployed at positions which surround the tissue opening such that tensioning the plurality of anchor cords can provide concentric compressive force upon the target tissue to reduce the size of the opening, including to close the opening. In some examples, the plurality of anchor cords can be deployed through the plurality of edge openings. For example, the surgical pad can be pre-coupled to the anchor cord deployment device, and the surgical pad can be subsequently positioned at a desired location on the target tissue such that each of the plurality of anchor cords can be deployed through a corresponding edge opening and into the target tissue. The surgical pad can be positioned such that the central opening is in alignment with the opening in the target tissue, and then the plurality of anchor cords can be deployed through corresponding edge openings of the surgical pad into the target tissue. In some examples, the plurality of anchor cords and/or anchors can be threaded through the surgical pad after deployment of the anchor cords and/or anchors.

As described in further detail herein, the anchor cords can extend through the target tissue so as to reduce or avoid interaction with any tethers extending through the opening in the target tissue. For example, the anchor cords be deployed around the opening and can extend linearly or substantially linearly through the target tissue such that tensioning the anchor cords to close the opening does not result in undesired tissue loading on the tethers and/or abrasion of the tethers by the anchor cords. Use of the surgical pads can thereby facilitate deployment of a pattern of suturing which can reduce or eliminate damage to the tethers caused by closing of the opening.

The surgical pad can comprise any number of materials. In some examples, the surgical pad can comprise polytetrafluoroethylene (PTFE), including expanded polytetrafluoroethylene (ePTI-E). In some examples, the surgical pad can comprise a pledget. The surgical pad can comprise any number of flexible biocompatible materials. The plurality of anchor cords and/or anchors can comprise any number of biocompatible materials. In some examples, the plurality of anchor cords and/or anchors can comprise ePTFE. In some examples, the plurality of anchor cords and/or anchors can comprise polypropylene. The anchor cords and/or anchors can comprise any number suture materials.

Referring again to FIG. 12A, in some examples, the plurality of edge openings 1216 can be distributed evenly around the outer edge portion 1210. The plurality of edge openings 1216 can be in a circular or substantially circular pattern around the outer edge portion 1210 of the surgical pad 1202. In some examples, the plurality of edge openings 1216 can be in a differently shaped pattern around the outer edge portion 1210. Although FIG. 12A shows six edge openings 1216 distributed around the outer edge portion 1210 of the surgical pad 1202, it will be understood that fewer or more edge openings 1216 can also be applicable. A spacing, pattern and/or number of the plurality of edge openings 1216 can be selected to provide a desired pattern of force and/or magnitude of force exerted by the anchor cords to close the opening in the target tissue.

The central opening 1214 can have any number of shapes. In some examples, the central opening 1214 can have a circular or substantially circular shape. An outer edge 1212 of the surgical pad 1202 can have any number of shapes. In some examples, an outer edge 1212 of the surgical pad 1202 can have a circular or substantially circular shape. In some examples, the surgical pad 1202 can have a circular or substantially circular doughnut shape. In some examples, the outer edge 1212 and/or the central opening 1214 of the surgical pad 1202 can comprise an oval shape and/or a rectangular shape. The surgical pad 1202 can comprise an oval doughnut shape or a rectangular doughnut shape.

As described in further detail herein, the plurality of anchor cords 1220 can comprise a portion configured to be deployed into the target tissue and another portion configured to be extending externally of the target tissue and through the plurality of edge openings 1216. The plurality of anchor cords 1220 can comprise a plurality of pairs of anchor cords 1220a, 1220b, each of the plurality of pairs of anchor cords 1220a, 1220b being coupled a corresponding anchor (not shown) secured to the target tissue. Although FIG. 12 shows six pairs of anchor cords 1220a, 1220b, it will be understood that fewer or more pairs of anchor cords 1220 can also be applicable. Portions of the plurality of anchor cords 1220 extending externally of the target tissue can extend through respective ones of the plurality of edge openings 1216 of the surgical pad 1202. In some examples, a pair of anchor cords 1220a, 1220b can be configured to extend through a corresponding one of the plurality of edge openings 1216, such as shown in FIG. 12A.

Figures 12C, 12D:
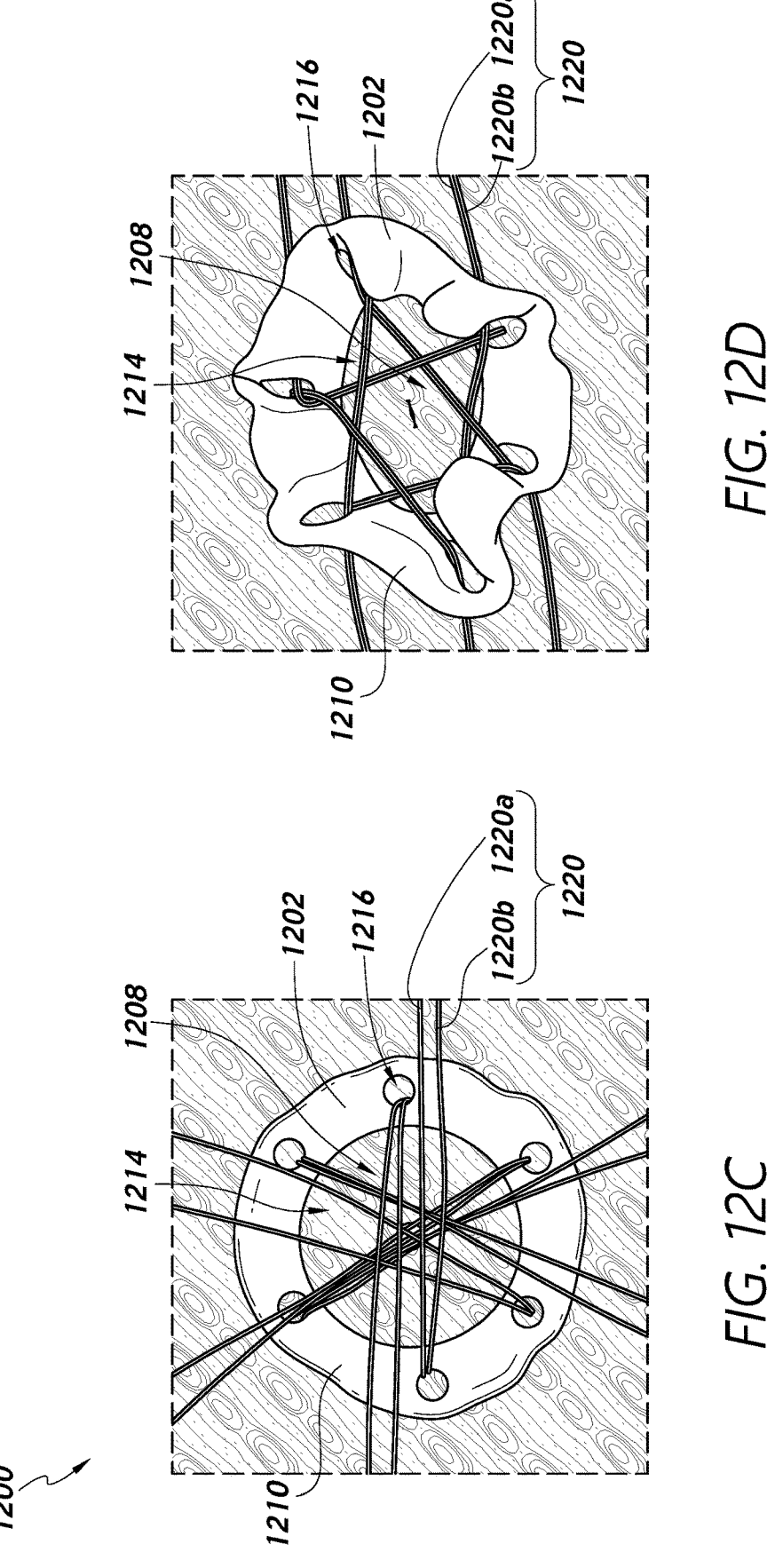
FIG. 12D shows the arrangement of FIG. 12B in a tensioned state.

The plurality of anchor cords 1220 can be tensioned to close the opening in the target tissue. FIGS. 12B and 12C show different arrangements of the anchor cords 1220 to facilitate desired tensioning of the anchor cords 1220. In some examples, the arrangement of the anchor cords 1220 can be selected to provide a desired pattern of force for closing the opening. FIG. 12B shows the plurality of anchor cords 1220 extending from the target tissue and through a first one of the plurality of edge openings 1216, and then threaded through a second of the plurality of edge openings 1216. In some examples, threading the plurality of anchor cords 1220 through a second edge opening 1216 prior to tensioning the plurality of anchor cords 1220 can facilitate improved closing and/or sealing of the opening in the target tissue. In the configuration shown in FIG. 12B, the second edge opening 1216 through which an anchor cord 1220 can be advanced can be selected such that the opening in the target tissue can remain unobstructed. As described herein, a pair of anchor cords 1220a, 1220b can extend from the target tissue and through a corresponding one of the edge openings 1216. In the example shown in FIG. 12B, each pair of anchor cords 1220a, 1220b can extend from the target tissue and through a corresponding one of the edge openings 1216 and threaded through a second one of the edge openings 1216. The second one of the edge openings 1216 is a second neighboring edge opening 1216, such that the opening in the target tissue can remain unobstructed. The routing of the pairs of anchor cords 1220a, 1220b can be selected such that an opening remains over the center portion 1208 of the surgical pad 1202 in alignment with both the central opening 1214 of the surgical pad 1202 and the opening in the target tissue to facilitate insertion and/or removal of surgical instrumentation through the opening in the target tissue. A pair of anchor cords 1220a, 1220b can be advanced from the first surface 1204 of the surgical pad 1202 and through an edge opening 1216 to the second surface 1206 and then threaded from the second surface 1206 through a second edge opening 1216 and to the first surface 1204.

FIG. 12C shows another example of arranging the anchor cords 1220. In the arrangement shown in FIG. 12C, the plurality of anchor cords 1220 can be folded over across the surgical pad 1202. For example, each pair of anchor cords 1220a, 1220b can be advanced from the first surface 1204 of the surgical pad 1202 and through an edge opening 1216 to the second surface 1206 and then folded over the second surface 1206 and positioned over another portion of the surgical pad 1202. In some examples, the other portion of the surgical pad 1202 can be at a location on the surgical pad 1202 opposite that of the first edge opening 1216. In this arrangement, the anchor cords 1220 can extend across the center portion 1208 of the surgical pad 1202, including over the opening in the target tissue in alignment with the central opening 1214. Although FIG. 12C shows the plurality of anchor cords 1220 traversing over the opening in the target tissue, any tethers extending through the opening in the target tissue can or substantially can be undamaged due to any interaction with the plurality of anchor cords 1220 as the anchor cords 1220 can be flexible cords.

In some examples, the plurality of anchor cords 1220 can be tensioned after being placed in the arrangements shown in FIGS. 12B and 12C. For example, the plurality of anchor cords 1220 can be divided into groups, such as two groups, and tensioned to close the opening in the target tissue. FIG. 12D shows the suture system 1200 having the arrangement shown in FIG. 12B where the plurality of anchor cords 1220 are tensioned. The plurality of anchor cords 1220 can be divided into two groups, one to each of two opposing sides of the surgical pad 1202 and tensioned to close the opening in the target tissue. It will be understood that the plurality of anchor cords 1220 can arranged differently prior to being tensioned.

Figure 13:
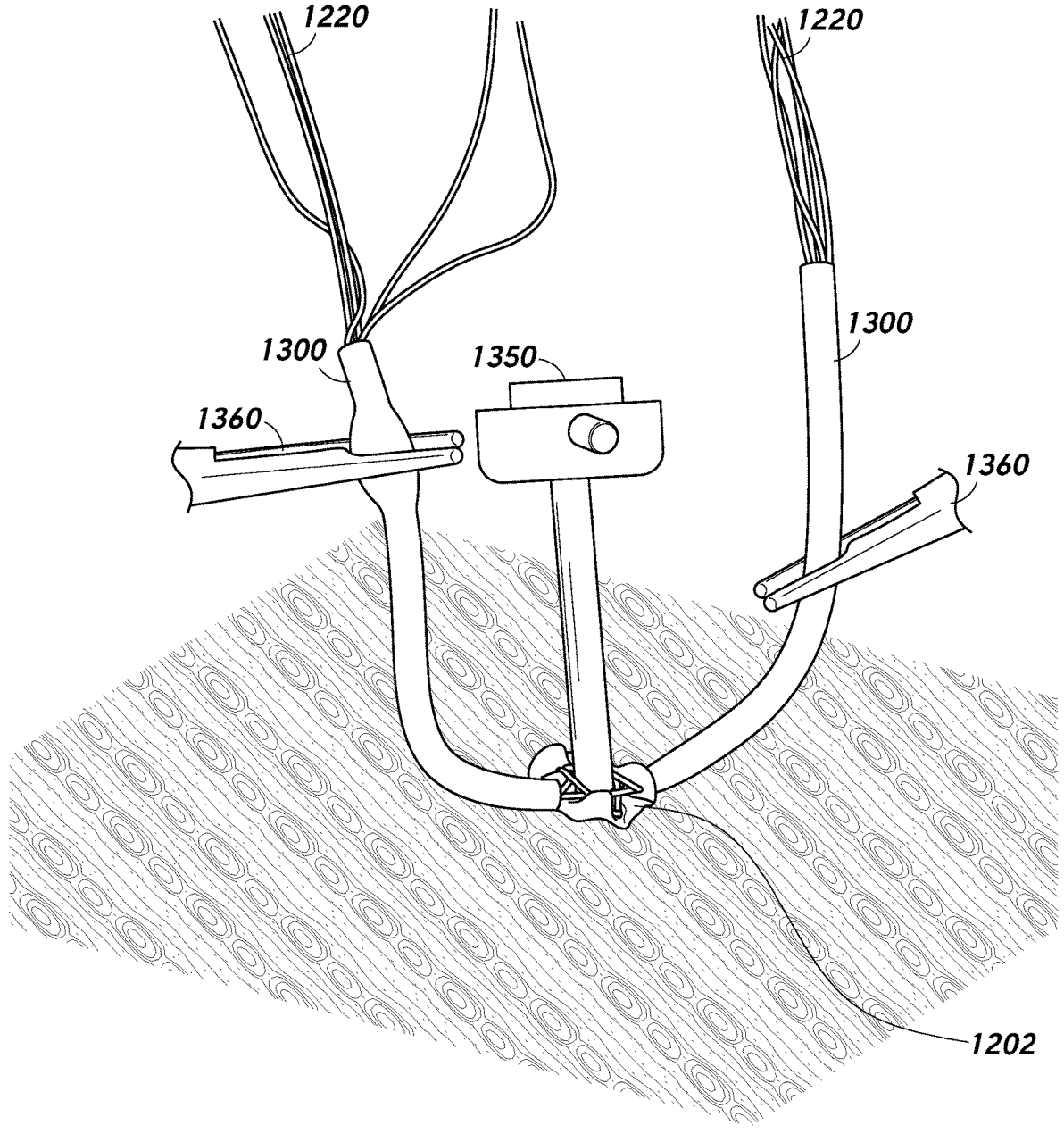
FIG. 13 shows an example of the suture system described with reference to FIG. 12 where the plurality of anchor cords is in a tensioned state.
Figure 14:
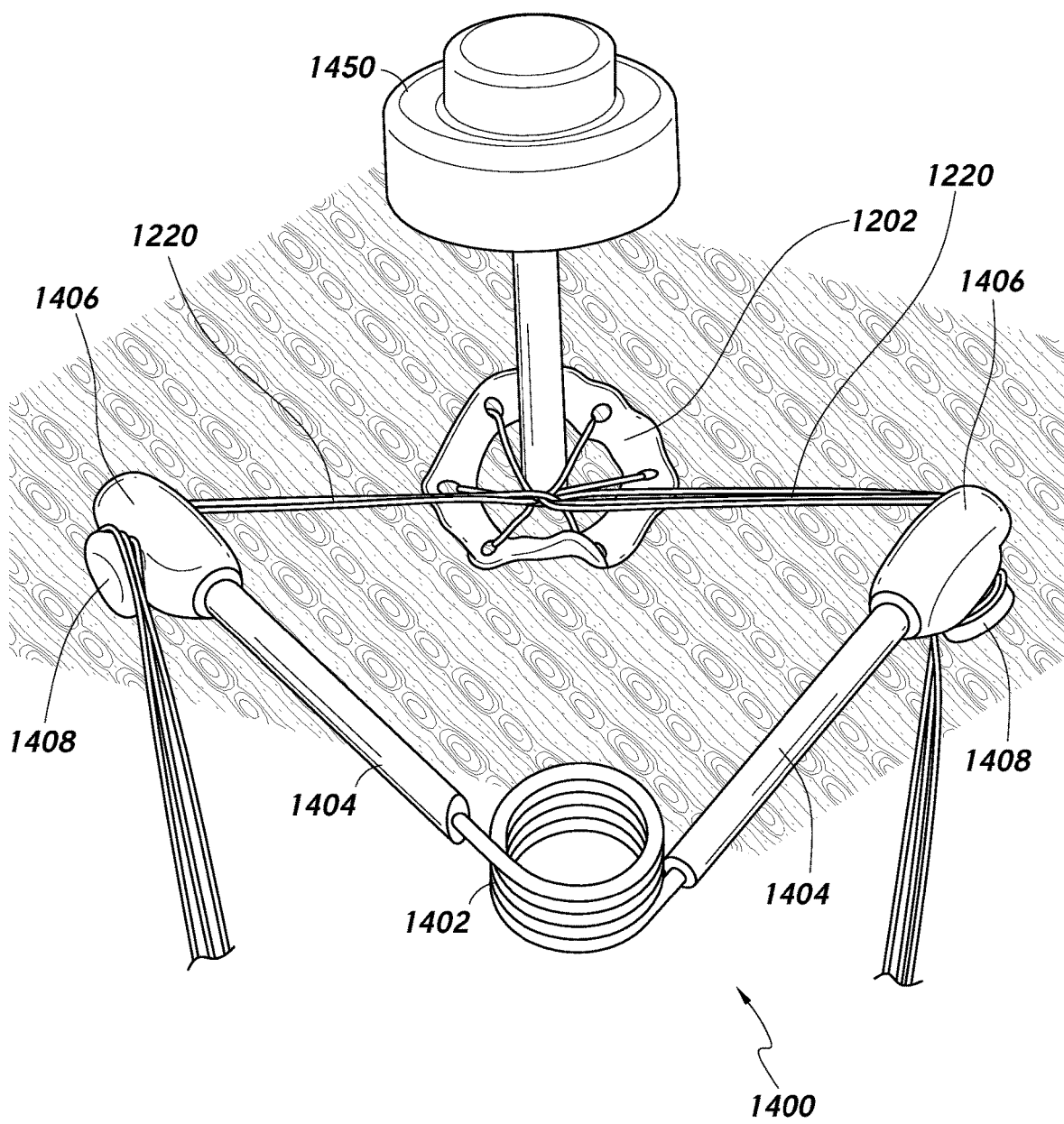
FIG. 14 shows another example of the suture system described with reference to FIG. 12 where the plurality of anchor cords is in a tensioned state.

FIGS. 13 and 14 show examples of the suture system 1200 described with reference to FIG. 12 where the plurality of anchor cords 1220 are in a tensioned state. Referring to FIG. 13, a surgical instrumentation 1350, such as an introducer, is shown inserted within the opening in the target tissue and the size of the opening is reduced such that the opening is closed around the surgical instrumentation 1350, such as to maintain hemostasis at the opening. The anchor cords 1220 extending through the surgical pad 1202 have been tensioned to close the opening around the surgical instrumentation 1350. In some examples, the anchor cords 1220 can have the arrangement shown in FIG. 12B or 12C. The anchor cords 1220 can then be divided into two groups.

Each of the two groups can be inserted through a respective elongate tube 1300, such as a tourniquet. The elongate tube 1300 can facilitate grouping and fixating the positions of the anchor cords 1220 to maintain the tension of the anchor cords 1220. The position of the anchor cords 1220 can be fixed relative to the corresponding elongate tube 1300 so as to maintain a desired tension in the anchor cords 1220 to hold the opening closed around the surgical instrumentation. As shown in FIG. 13, a respective clamp 1360 can be used to pinch each of the elongate tubes 1300 against the anchor cords 1220 extending therethrough to fix the positions of the anchor cords 1220 relative to the corresponding elongate tubes 1300 to thereby maintain the desired tension in the anchor cords 1220.

Referring to FIG. 14, a surgical instrumentation 1450, such as an introducer, is shown as being inserted within the opening in the target tissue. The size of the opening is reduced such that the opening is closed around the surgical instrumentation 1450 to maintain hemostasis. The anchor cords 1220 of the suture system 1200 can be tensioned to close the opening around the surgical instrumentation 1450. In the arrangement shown in FIG. 14, the plurality of anchor cords 1220 have been extended to the center portion 1208 of the surgical pad 1202 and wound around one another over the center portion 1208. The plurality of anchor cords 1220 can be tied together over the center portion 1208. The tensioned anchor cords 1220 can be maintained in the tensioned state using a spring-loaded device. For example, FIG. 14 shows a spring-loaded tensioner 1400 comprising a spring 1402 and two arms 1404 extending from the spring 1402. The two arms 1404 can form an angle that is less than about 180°. The distal portions 1406 of the arms can comprise an anchor cord engagement feature 1408 configured to receive at least a portion of one or more anchor cords 1220. In some examples, the anchor cord engagement feature 1408 can comprise a knob around which one or more anchor cords 1220 can be wound so as to maintain a desired tension of the anchor cords 1220. In FIG. 14, the plurality of anchor cords 1220 can be divided into two groups, a first group having a portion fixedly coupled to the anchor cord engagement feature 1408 of one arm 1404 and a second group having a portion fixedly coupled to the anchor cord engagement feature 1408 of the other arm 1404. For example, the first group and second group of anchor cords 1220 can comprise respective portions wound around a knob on the distal portion 1406 of each arm 1404 so as to maintain the desired tension of the anchor cords 1220.

The configurations shown in FIGS. 13 and 14 are for illustrative purposes only. A temporary tension in the anchor cords 1220 to close the opening in the target tissue around surgical instrumentation extending therethrough, such as to maintain hemostasis, can be maintained in a number of other manners.

As described herein, after deployment of the medical device and/or therapy is complete, surgical instrumentation inserted within the opening in the target tissue can be withdrawn and the anchor cords 1220 can be further tensioned to further reduce the size of the opening so as to close the opening. Positions of the plurality of anchor cords 1220 can be fixed relative to the target tissue to close the opening. In some examples, the anchor cords 1220 can be knotted so as to maintain the tension in the anchor cords 1220 to close off the opening. Any number of techniques can be used to fixate the position of the anchor cords 1220 to maintain the tension (e.g., locking knots and/or SUTRAFIX® clip applier, Edwards Lifesciences Corp., Irvine, CA).

Figures 15A, 15B:
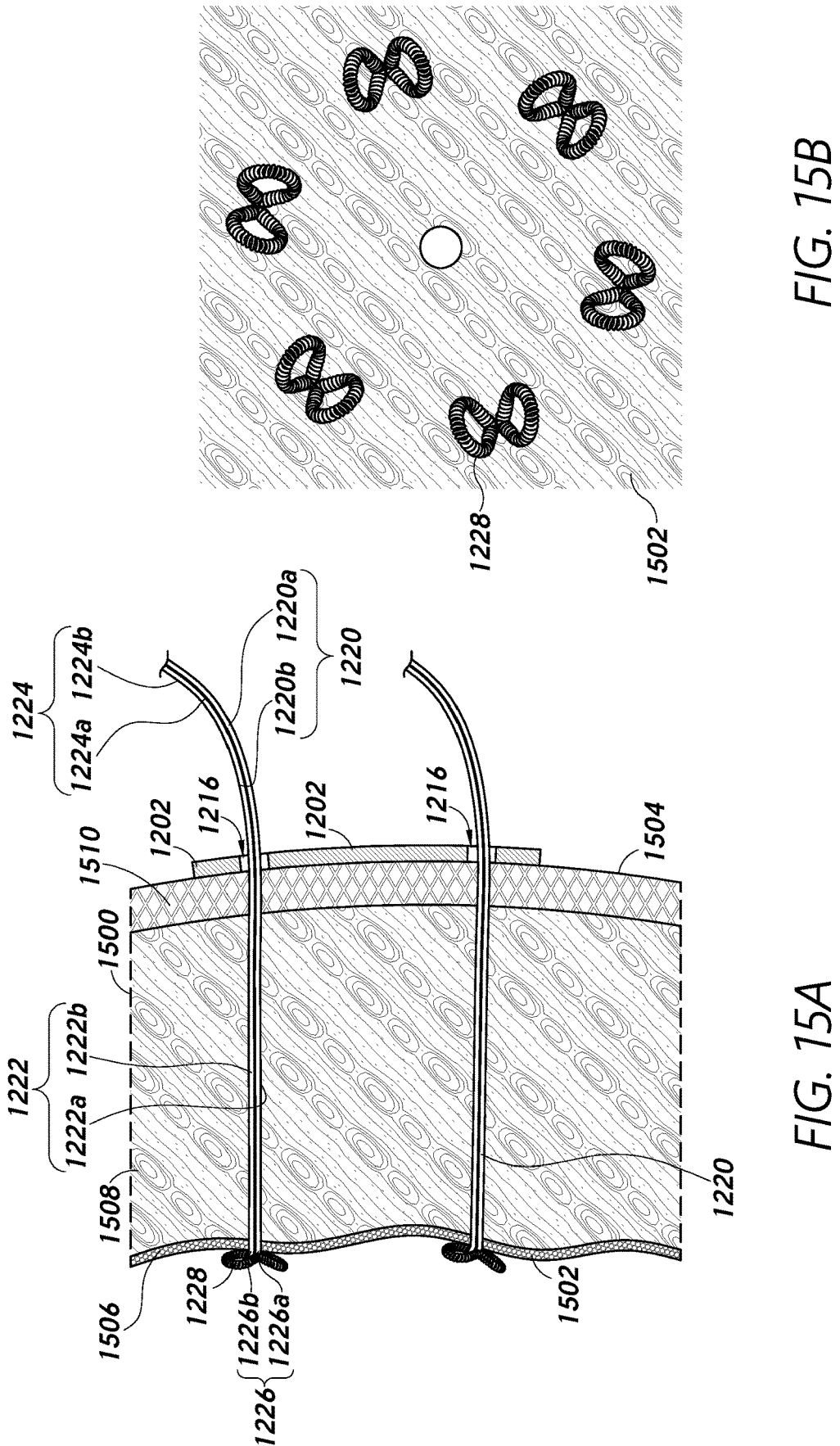
FIG. 15A is a cross-sectional view of the suture system described with reference to FIG. 12 comprising the plurality of anchor cords deployed into the target tissue.
FIG. 15B is a plan view of a plurality of anchors positioned on a first surface of the target tissue.
Figure 15C:
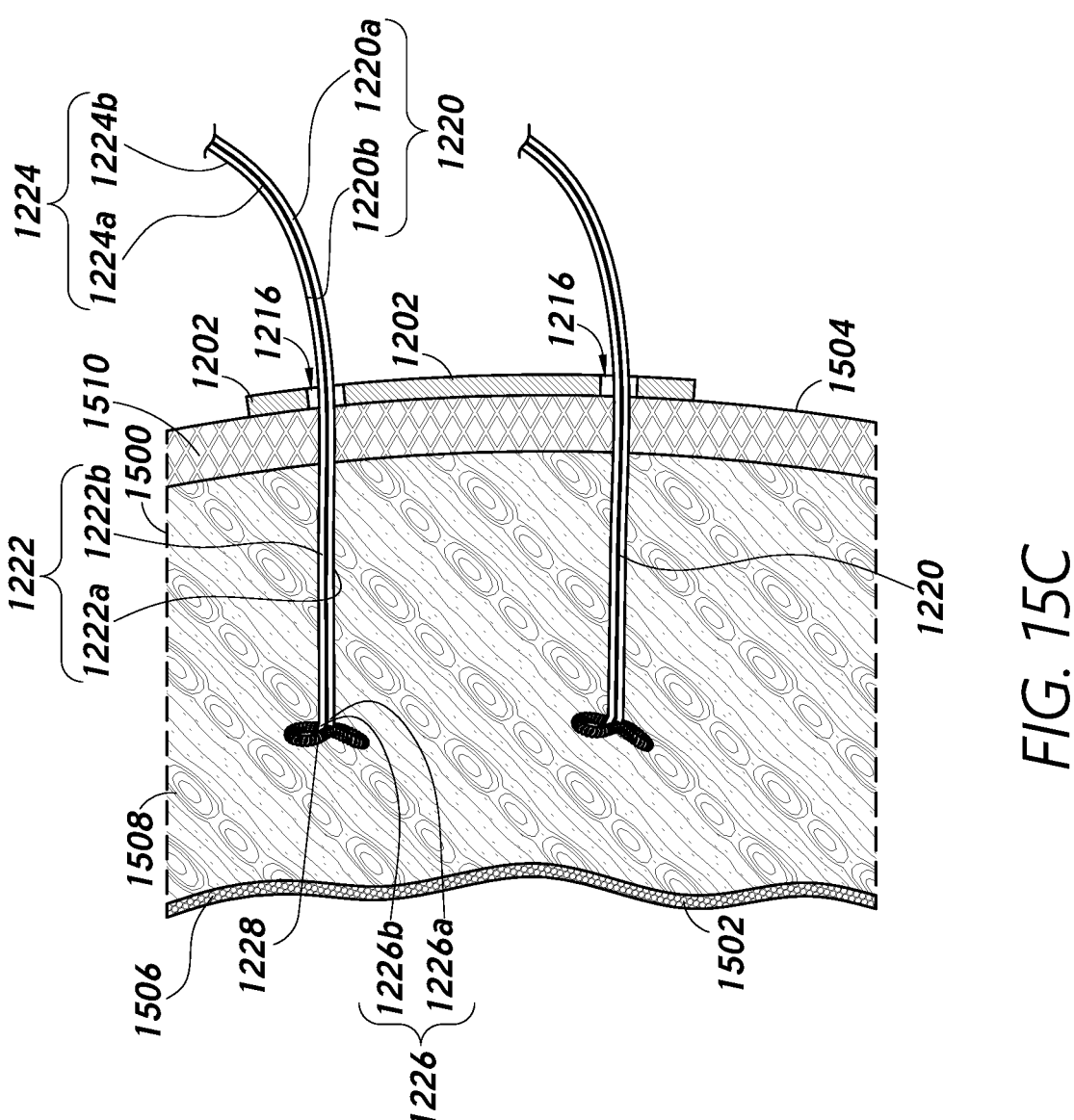
FIG. 15C is a cross-sectional view of the plurality of anchor cords deployed only partially through the thickness of the target tissue.

FIGS. 15A through 15C show examples of the suture system 1200 described with reference to FIG. 12 deployed into the target tissue. FIGS. 15A and 15B show an example of the suture system 1200 described with reference to FIG. 12 comprising the plurality of anchor cords 1220 deployed through an entire thickness of the target tissue 1500. FIG. 15C shows an example of the plurality of anchor cords 1220 deployed only partially through the thickness of the target tissue 1500.

FIG. 15A is a cross-sectional view of two of the plurality of anchor cords 1220 deployed into the target tissue 1500. Each of the plurality of anchor cords 1220 can have a distal portion 1222 deployed into the target tissue 1500. A distal end 1226 of each of the anchor cords 1220 can be coupled to a respective anchor 1228. In some examples, a distal end 1226 of an anchor cord 1220 can be coupled to a suture knot. In some examples, a suture knot can be formed using a portion of an anchor cord 1220. For example, the suture knot can be integral with the anchor cord 1220. In some examples, suture knots and anchor cords can provide desired anchoring while reducing undesired interaction with the adjacent tissue. For example, the suture knots and plurality of anchor cords 1220 can be comprise desired pliability and/or deformability, while providing a reduced profile within the target tissue, thereby reducing undesired irritation of the target tissue. However, it will be understood that the anchor 1228 is not limited to suture knots and can be any number of types of anchors, including rigid or semi-rigid anchors.

The plurality of anchors 1228 can be deployed to the same or substantially the same depth within the target tissue. The uniformity in depth of the anchors 1228 can provide improved security in the closing of the opening in the target tissue, preventing undesired migration of anchors through the target tissue, thereby reducing or eliminating tissue damage and/or device failure.

The anchors 1228 are shown in FIG. 15A as being positioned over a first surface 1502 of the target tissue. The anchor cords 1220 are shown as extending through an entire thickness of the target tissue. For example, the distal portions 1222 of the anchor cords 1220 are shown as being embedded within the target tissue, for example extending through an entire thickness of the target tissue 1500, with the distal ends 1226 coupled to the anchors 1228 positioned over the first surface 1502 of the target tissue 1500. Proximal portions 1224 of the anchor cords 1220 can extend from a second surface 1504 of the target tissue 1500. The proximal portions 1224 can extend through corresponding edge openings 1216 in the surgical pad 1202.

As described herein, the plurality of anchor cords 1220 can comprise a plurality of pairs of anchor cords 1220a, 1220b. For example, a pair of anchor cords 1220a, 1220b can be coupled to a corresponding anchor 1228, distal portions 1222a, 1222b of each pair of anchor cords 1220a, 1220b can be within the target tissue 1500 and proximal portions 1224a, 1224b of each anchor of the pair of anchor cords 1220a, 1220b can extend from the second surface 1504 of the target tissue 1500. Distal ends 1226a, 1226b of each anchor of the pair of anchor cords 1220a, 1220b can be coupled to an anchor 1228. Proximal portions 1224a, 1224b of each anchor cord of the pairs of anchor cords 1220a, 1220b can extend through a corresponding edge opening 1216 of the surgical pad 1202. Although FIG. 15A shows a pair of anchor cords 1220a, 1220b extending from each anchor 1228, as described herein, each anchor 1228 can be coupled to one anchor cord 1220.

FIG. 15B is a view of the plurality of anchors 1228 on the first surface 1502 of the target tissue 1500 and shows six anchors 1228 around an opening in the target tissue 1500. The plurality of anchors 1228 can be positioned over and in contact with the first surface 1502 of the target tissue 1500. In some examples, the anchors 1228 can be evenly distributed around the opening. In some examples, the anchors 1228 can be in a circular or substantially circular pattern around the opening. The anchor cords 1220 can extend linearly or substantially linearly through the target tissue 1500 such that proximal portions 1224 of the anchor cords 1220 extend from corresponding positions on the second surface 1504 of the target tissue 1500. For example, the proximal portions 1224 can extend from the second surface 1504 at positions which form a circular or substantially circular shape surrounding the opening in the target tissue. In some examples, the positions of the anchor cords 1220 form a shape other than a circle in the target tissue 1500, including an oval, a pentagon, a hexagon or a rectangle. In some examples, the distal portions 1222 of the anchor cords 1220 within the target tissue 1500 does not interfere with the paths of any tethers extending through the opening of the target tissue, reducing or eliminating any damage to the tethers caused by the closing of the opening. For example, having the distal portions 1222 extending linearly or substantially linearly into the target tissue can reduce or prevent paths of the tethers crossing with those of the anchor cords 1220.

FIG. 15C shows the suture system 1200 described with reference to FIG. 12 where the plurality of anchor cords 1220 are deployed to extend partially into the target tissue 1500. For example, the anchors 1228 can be embedded within the target tissue 1500. The anchor cords 1220 may not extend through an entire thickness of the target tissue 1500 but may extend only partially through the target tissue 1500 such that the anchors 1228 are at a position within the target tissue 1500.

In some examples, the plurality of anchor cords 1220 can comprise a plurality of pairs of anchor cords 1220a, 1220b such that distal portions 1222a, 1222b of each pair of anchor cords 1220a, 1220b can extend through a partial thickness of the target tissue 1500. For example, distal ends 1226a, 1226b of a pair of anchor cords 1220a, 1220b can be coupled to a corresponding anchor 1228 positioned within the target tissue 1500. Proximal portions 1224a, 1224b of each of the pairs of anchor cords 1220a, 1220b can extend from the second surface 1504 of the target tissue 1500 and through a corresponding edge opening 1216 of the surgical pad 1202.

In some examples, the target tissue 1500 can be heart wall tissue. In some examples, the target tissue 1500 can be ventricular heart wall tissue. The opening can be formed in an apex region of the heart, such as in the apex region of the heart on the left ventricular heart wall. In some examples, the target tissue 1500 can comprise layers of the heart wall, such as the endothelium layer 1506, myocardium layer 1508 and epicardium layer 1510 of the heart wall. For example, the distal portions 1222a, 1222b of the pairs of anchor cords 1220a, 1220b can extend through the entirety of each of the endothelium layer 1506, myocardium layer 1508 and epicardium layer 1510. The view shown in FIG. 15B can be a portion of a ventricle facing surface of the endothelium layer 1506. For example, the distal ends 1226a, 1226b of the pairs of anchor cords 1220a, 1220b can be proximate or adjacent to the ventricle facing surface of the endothelium layer 1506 and the anchors 1228 can be positioned over the ventricle facing surface of the endothelium layer 1506. The anchors 1228, such as suture knots, can be positioned over and in contact with the ventricle facing surface of the endothelium layer 1506. In some examples, such as that shown in FIG. 15C, the pairs of anchor cords 1220a, 1220b can extend only partially through a layer of the heart wall. For example, the distal portions 1222a, 1222b of the pairs of anchor cords 1220a, 1220b may extend through the epicardium layer 1510 but only partially through the myocardium layer 1508. The anchors 1228 can be positioned within the myocardium layer 1508.

The proximal portions 1224a, 1224b can extend from the epicardium layer 1510, such as a surface of the epicardium layer 1510 oriented away from the myocardium layer 1508. The proximal portions 1224a, 1224b can extend externally of the heart ventricle. In some examples, the target tissue can comprise the pericardium. For example, the distal portions 1222a, 1222b can extend through the each of an endothelium layer, myocardium layer, epicardium layer and pericardium. The proximal portions 1224a, 1224b can extend from a surface of the pericardium oriented away from the epicardium layer.

Figure 16:
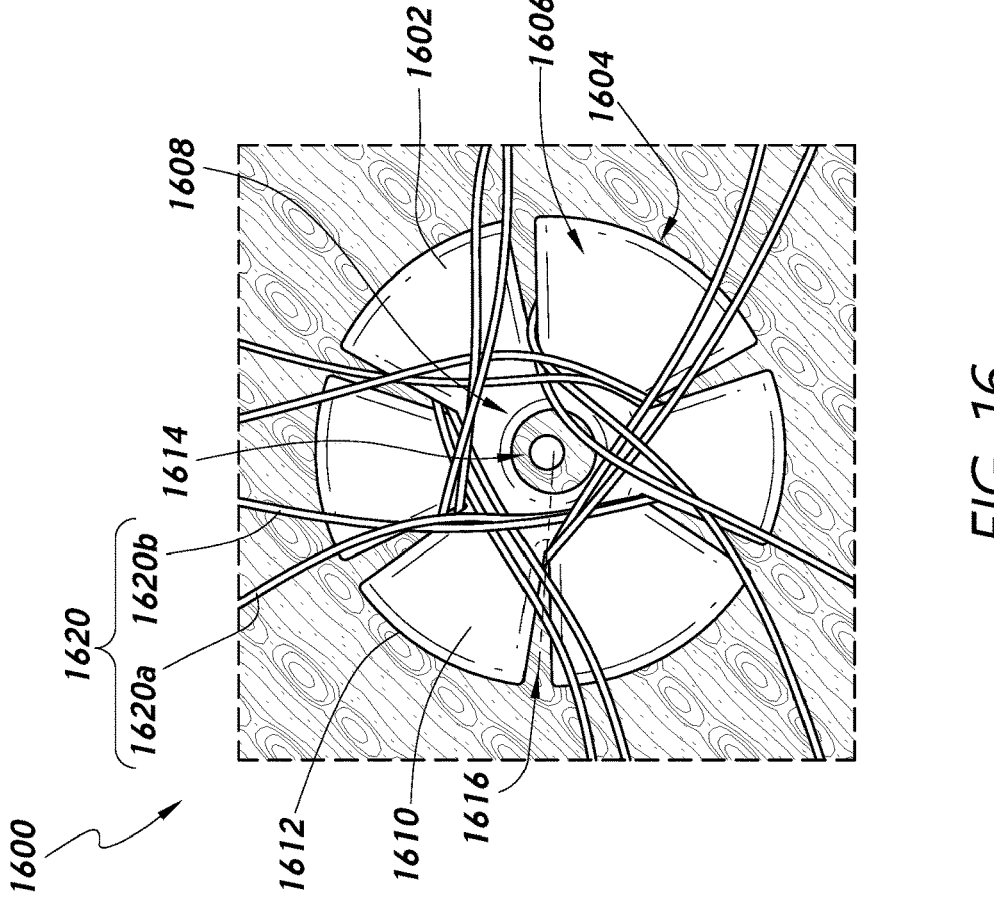
FIG. 16 is a plan view of an example of a suture system comprising a surgical pad which has a central opening and a plurality of edge openings that open to the outer edge of the surgical pad, and a plurality of anchor cords.

FIG. 16 shows a suture system 1600 comprising a surgical pad 1602 which has a central opening 1614 at a center portion 1608 and a plurality of edge openings 1616 distributed around an outer edge portion 1610 of the surgical pad 1602, where the plurality of edge openings 1616 open to the outer edge 1612 of the surgical pad 1602. In some examples, the plurality of edge openings 1616 can comprise a plurality of slits which open to the outer edge 1612 of the surgical pad 1602. For example, the plurality of edge openings 1616 can comprise a plurality of radially extending slits on the outer edge portion 1610, where the slits open to the outer edge 1612 of the surgical pad 1602.

The suture system 1600 can have one or more other features of the suture system 1200 described with reference to FIG. 12. A first surface 1604 of the surgical pad 1602 can be configured to be oriented toward the target tissue and a second surface 1606 can be configured to be oriented away from the target tissue. In some examples, the outer edge 1612 of the surgical pad 1602 and the central opening 1614 can each have a circular or substantially circular shape. For example, the surgical pad 1602 can have a circular or substantially circular doughnut shape. The plurality of edge openings 1616 can be evenly distributed around the outer edge portion 1610. FIG. 16 shows that the suture system 1600 can include six edge openings 1616 evenly distributed around the outer edge portion 1610 of the surgical pad 1602. It will be understood that more or fewer edge openings 1616 can also be applicable. The suture system 1600 can comprise a plurality of anchor cords 1620, or pairs of anchor cords 1620a, 1620b, configured to be positioned through corresponding edge openings 1616. FIG. 16 shows the plurality of anchor cords 1620 arranged over the surgical pad 1602 to provide an opening in the anchor cords 1620 over the center portion 1608 of the surgical pad 1602. The opening in the anchor cords 1620 can be in alignment with the central opening 1614 of the surgical pad 1600 and the opening in the target tissue.

In some examples, a pad comprising a plurality of openings which opens to an outer edge of the pad can facilitate positioning of the pad over a target tissue subsequent to deployment of the anchor cords into the target tissue. For example, the plurality of anchor cords can be threaded through the openings after the anchor cords are deployed into the tissue, facilitating adjustment of the position of the surgical pad.

Figure 17:
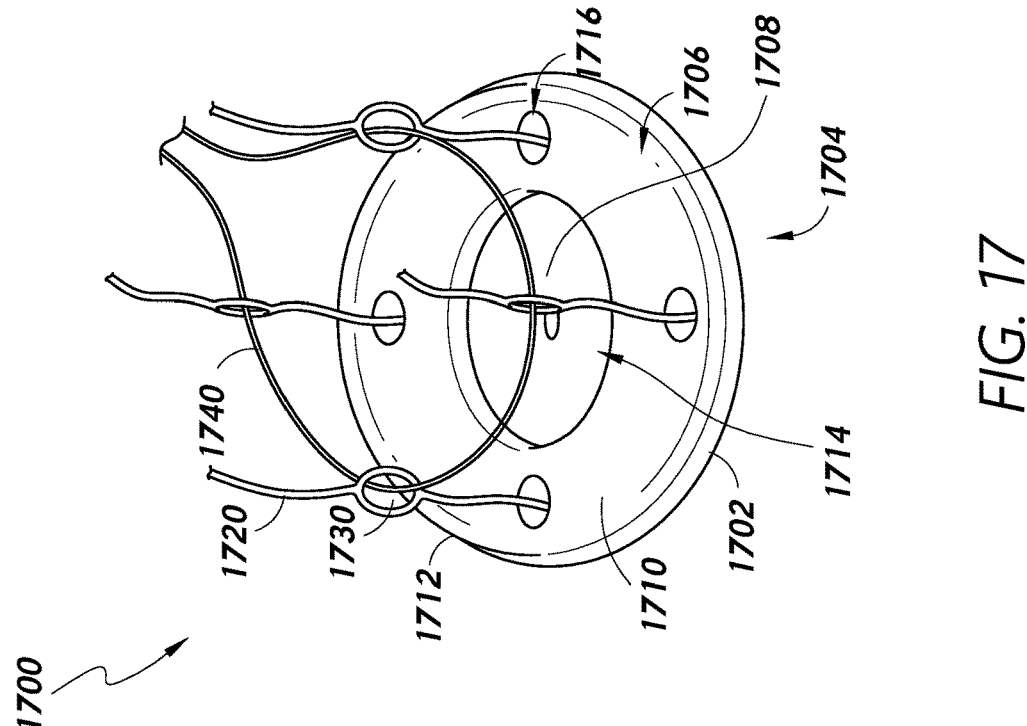
FIG. 17 is a perspective view of an example of a suture system comprising a surgical pad which has a central opening and a plurality of edge openings, a plurality of anchor cords each comprising an eyelet, and a secondary cord configured to be threaded through the eyelets.

FIG. 17 shows a suture system 1700 comprising a surgical pad 1702 which has a central opening 1714 at a center portion 1708 and a plurality of edge openings 1716 around an outer edge portion 1710 of the surgical pad 1702, and a plurality of anchor cords 1720 extending through a corresponding edge opening 1716. Each of the plurality of anchor cords 1720 can have an eyelet 1730 on the portion extending externally of the target tissue. Each of the eyelets 1730 can be configured to be positioned over a respective edge opening 1716. The suture system 1700 can have a secondary cord 1740 configured to be threaded through each of the eyelets 1730. The secondary cord 1740 can be tensioned, in addition to tensioning of the plurality of anchor cords 1720, to facilitate improved closing of the opening in the target tissue. The secondary cord 1740 can comprise a variety of materials, including any number of biocompatible materials. The secondary cord 1740 can be a suture. In some examples, the secondary cord 1740 can comprise any number of flexible suture materials. In some examples, the secondary cord 1740 can comprise an ePTFE suture. In some examples, the secondary cord 1740 can comprise a polypropylene suture. The secondary cord 1740 can be configured to form a secondary purse-string suture. For example, tensioning the secondary cord 1740 can form the secondary purse-string suture.

FIG. 17 shows that the surgical pad 1702 comprises four edge openings 1716 and four anchor cords 1720, each anchor cord 1720 being configured to be positioned through a corresponding edge opening 1716. In some examples, the suture system 1700 can comprise a plurality of pairs of anchor cords. For example, a pair of anchor cords can extend through an edge opening 1716. It will be understood that more or fewer edge openings 1716 can also be applicable.

The suture system 1700 can have one or more other features of the suture system 1200 described with reference to FIG. 12. A first surface 1704 of the surgical pad 1702 can be configured to be oriented toward the target tissue and a second surface 1706 can be configured to be oriented away from the target tissue. The surgical pad 1702 can be positioned over the target tissue such that the central opening 1714 is in alignment with the opening in the target tissue. In some examples, the outer edge 1712 of the surgical pad 1702 and the central opening 1714 can each have a circular or substantially circular shape. For example, the surgical pad 1702 can have a circular or substantially circular doughnut shape. The edge openings 1716 can be evenly distributed around the outer edge portion 1710 of the surgical pad 1702. Each of the plurality of cords 1720 can comprise a portion configured to be deployed into the target tissue and another portion configured to extend externally of the target tissue and through a corresponding edge opening 1716. Although FIG. 17 shows one anchor cord 1720 extending through each edge opening 1716, it will be understood that a pair of anchor cords can extend through each edge opening 1716.

FIG. 18 is a process flow diagram of an example of a deployment process 1800 for deploying a suture system as described herein. In some examples, the suture system can include a surgical pad comprising a central opening in a center portion of the surgical pad and a plurality of edge openings around an outer edge portion of the pad. The suture system can include a plurality of anchor cords, each of the plurality of anchor cords comprising a portion configured to be extended through a corresponding one of the plurality of edge openings.

In block 1802, the process 1800 involves providing the surgical pad comprising the central opening in the center portion of the pad and the plurality of edge openings around the outer edge portion of the pad. In block 1804, the process 1800 involves positioning the surgical pad over a target tissue, the central opening in alignment with an opening in the target tissue. The surgical pad can comprise a first surface being configured to be oriented toward the target tissue and a second surface being configured to be oriented away from the target tissue. For example, the first surface can be positioned on and in contact with the target tissue while the second surface can be oriented in an opposing direction relative to the first surface. The central opening of the pad can be aligned with the opening in the target tissue such that surgical instrumentation can be positioned within the opening in the target tissue without obstruction from the surgical pad.

In block 1806, the process 1800 involves providing the plurality of anchor cords, each of the plurality of anchor cords comprising a portion extending through a corresponding edge opening and another portion embedded within the target tissue. In some examples, each of the plurality of anchor cords can be extended through the corresponding edge opening prior to positioning the pad over the target tissue. In some examples, the plurality of anchor cords can be extended through the corresponding edge opening after positioning the pad over the target tissue. As described herein, each of the plurality of edge openings can open to an outer edge of the pad. For example, each of the plurality of edge openings can comprise a slit. In some examples, the plurality of anchor cords can be extended through corresponding slits after positioning the pad over the target tissue.

In block 1808, the process 1800 involves tensioning the plurality of anchor cords extending through the plurality of edge openings to reduce a size of the opening. The plurality of anchor cords can be tensioned to close the opening around surgical instrumentation extending through the opening and/or to seal the opening subsequent to completion of a surgical procedure.

In some examples, the plurality of anchor cords can be threaded through a second edge opening prior to tensioning the plurality of anchor cords. For example, the plurality of anchor cords can be threaded through a second edge opening to facilitate desired closure of the opening in the target tissue, such as by facilitating a desired pattern of tensioning force exerted upon the opening. In some examples, the plurality of anchor cords can be threaded to a second edge opening on an opposing outer edge portion of the surgical pad. In some examples, the plurality of anchor cords can be threaded to a second edge opening so as to provide an opening in the routing of the plurality of anchor cords which aligns with the opening in the target tissue and the central opening of the surgical pad.

In some examples, each of the plurality of anchor cords can comprise an eyelet. The eyelets can be at a position on the anchor cords so as to be positioned over the surgical pad, such as over an edge opening of the surgical pad. The suture system can comprise a secondary cord. The secondary cord can be threaded through the plurality of eyelets. The secondary cord can be tensioned to reduce the size of the opening. The secondary cord can provide additional strength in closing the opening.

As described herein, the plurality of anchor cords can comprise a plurality of pairs of anchor cords. For example, the suture system can comprise a plurality of pairs of anchor cords, each anchor of the pair of the anchor cords comprising a first portion configured to be embedded within the target tissue and a second portion extending externally of the target tissue and through a corresponding one of the plurality of edge openings of the surgical pad.

Titration of tension in one or more surgical cords as described herein may be desired after the surgical cords have already been secured to a surgical pad. Adjustment in the tension of the surgical cords, such as a tether, may be desired to provide desired heart valve leaflet coaptation, including titrating after additional tethers have been deployed to the heart valve and/or secured to the surgical pad. Tension in one or more anchor cords can be adjusted after the anchor cords have already been secured to a surgical pad to provide desired closure of an opening in a target tissue. Undoing and/or redoing the coupling mechanism used to secure the surgical cords to the surgical pads may be difficult without to achieve, and/or lead to damage in the surgical cords and/or target tissue.

Described herein are systems, devices and methods relating to a spacer which can be used in combination with a surgical pad, including one or more surgical pads as described herein, to facilitate adjustment in the tension of one or more surgical cords already secured to a surgical pad. A surgical pad can comprise a pair of tethers or a pair of anchor cords secured thereto. Respective portions of the pair of tethers or pair of anchor cords can be secured together to one another over a surface of the surgical pad oriented away from the target tissue. One or more spacers can be placed between the surgical pad and the target tissue to facilitate adjustment in tension of the surgical cords and/or between the surgical pad and respective portions of the surgical cords positioned over the second surface of the surgical pad. The spacer can provide a separation between the surgical pad and the target tissue or between the surgical pad and respective portions of the surgical cords. The separation can provide additional tension to the surgical cords, thereby facilitating adjustment in the tension of the surgical cords without needing to redo the coupling of the surgical cords to the surgical pad. In some examples, increased tension in the surgical cords can facilitate improved heart valve leaflet coaptation. For example, increased tension of one or more tethers coupled to a heart valve leaflet can improve coaptation of the heart valve leaflets. In some examples, the additional separation between the surgical pad and the target tissue or between the surgical pad and respective portions of the surgical cords can reduce a length of the tethers extending within a heart chamber, thereby providing improved coaptation of the heart valve leaflets. In some examples, increasing tension in the surgical cords can facilitate improved closure of an opening in a target tissue as described herein. For example, increased tension in one or more anchor cords can facilitate pulling the anchor cords tighter to provide a desired closure of the opening.

In some examples, after the spacer is at its desired position, the spacer can be secured to the target tissue and/or the surgical pad. Any number of means for securing the spacer to the target tissue and/or surgical pad can be applicable, including for example sutures, glue, and/or staples. As described herein, in some examples, the target tissue can comprise the epicardium. In some examples, the target tissue can comprise the pericardium. For example, the spacer can be sutured, glued and/or stapled to epicardium and/or pericardium tissue. The spacer can comprise a number of different materials. In some examples, the spacer can comprise any number of resilient, flexible, deformable, compressible and/or biocompatible materials, including material used in cardiovascular surgery. The spacer can provide desired tensile and/or retention strength. In some examples, the spacer can comprise one or more of bovine pericardium, polytetrafluoroethylene (PTFE, e.g., TEFLON® PTFE, Dupont), polyurethane, and polyester. In some examples, the spacer can comprise a foam and/or felt material.

Figures 19A, 19B, 19C:
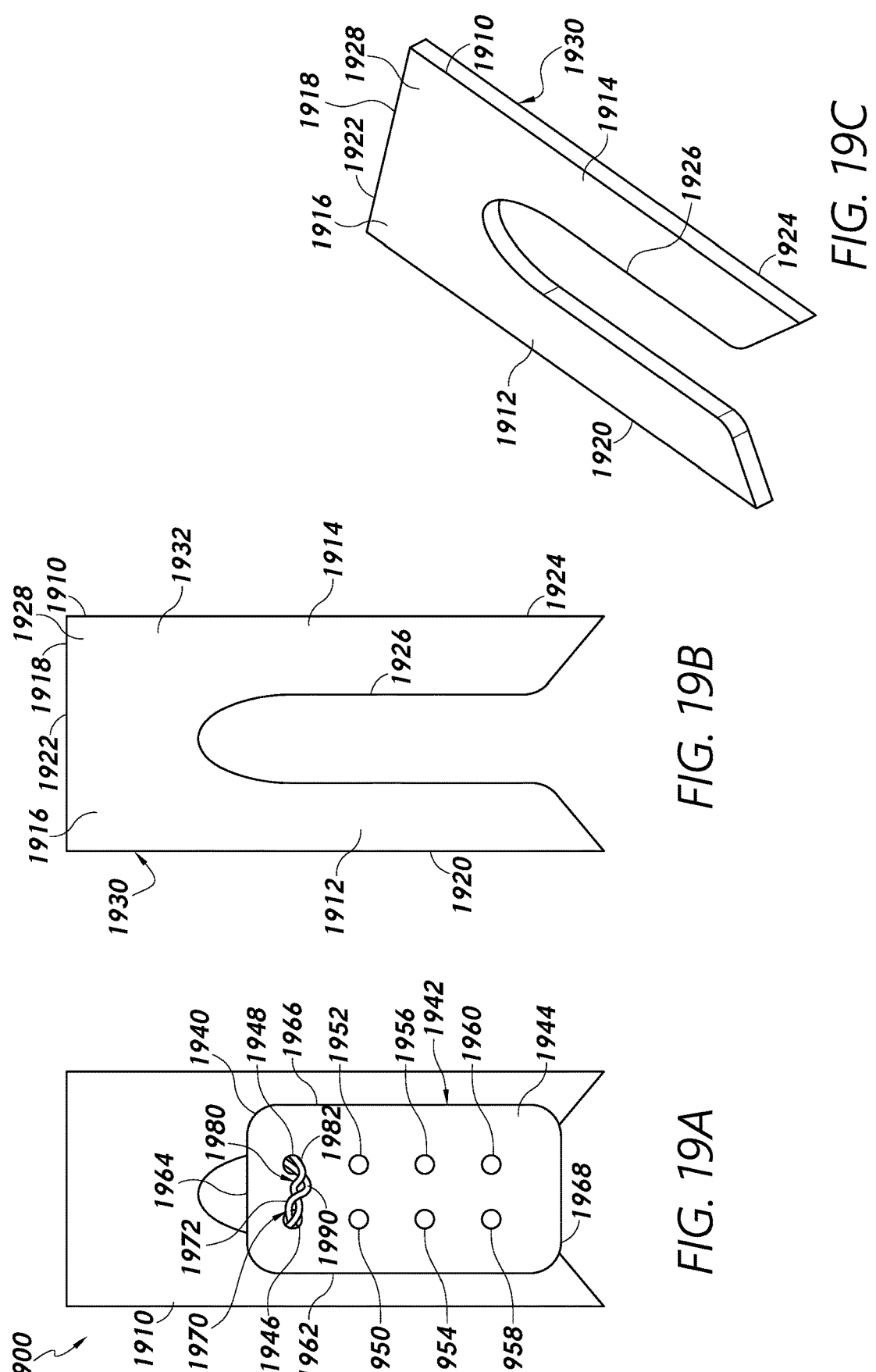
FIGS. 19A and 19B are top-down plan views of an example of a suture system and a spacer of the suture system, respectively.
FIG. 19C is a perspective view of the spacer of FIGS. 19A and 19B.

FIGS. 19A, 19B and 19C show an example of a suture system 1900 comprising a spacer 1910, a surgical pad 1940, and a first surgical cord 1970 and a second surgical cord 1980. FIG. 19A is a top-down plan view of the suture system 1900. FIG. 19B is a top-down plan view of the spacer 1910 and FIG. 19C is a perspective view of the spacer 1910. The surgical pad 1940 can be positioned over a target tissue and the spacer 1910 can be inserted between the target tissue and the surgical pad 1940. The first surgical cord 1970 and the second surgical cord 1980 can be secured to one another over the surgical pad 1940, such as over a surface of the surgical pad 1940 oriented away from the spacer 1910 and target tissue. Each of the surgical cords 1970, 1980 can be a tether as described herein. For example, each of the surgical cords 1970, 1980 can comprise a first portion extending within a heart ventricle and coupled to a heart valve leaflet, and a second portion extending externally of the heart wall through an opening in the heart wall.

Referring to FIG. 19A, the surgical pad 1940 can have a first surface 1942, such as a bottom surface, and a second surface 1944, such as a top surface. The first and second surfaces 1942, 1944 can have opposing orientations. While the surgical pad 1940 is positioned over a target tissue, the first surface 1942 can be configured to be oriented toward the target tissue and the second surface 1944 can be configured to be oriented away from the target tissue. The surgical pad 1940 can have a rectangular or substantially rectangular shape. For example, the surgical pad 1940 can comprise a first edge portion 1962, a second edge portion 1964, a third edge portion 1966 and a fourth edge portion 1968. The first edge portion 1962 and the third edge portion 1966 can be the longer edges and can be parallel or substantially parallel to one another. The second edge portion 1964 and fourth edge portion 1968 can be the two shorter edges and can be parallel or substantially parallel to one another. The second and fourth edge portions 1964, 1968 can be perpendicular or substantially perpendicular to, and extend between, the longer opposing edges 1962, 1966.

The surgical pad 1940 can have a plurality of openings, for example, eight openings 1946, 1948, 1950, 1952, 1954, 1956, 1958, 1960, each of the eight openings extending therethrough at a respective location. The first opening 1946 and the second opening 1948 can be a first pair of openings. The third opening 1950 and the fourth opening 1952 can be a second pair of openings. The fifth opening 1954 and the sixth opening 1956 can be a third pair of openings, and the seventh opening 1958 and the eight opening 1960 can be a fourth pair of openings. The first opening 1946 and the second opening 1948 can be at a respective first and second location which are laterally spaced from one another along a first lateral dimension. The third opening 1950 and the fourth opening 1952 can be a respective third and fourth location which are laterally spaced from one another along a second lateral dimension. The fifth opening 1954 and the sixth opening 1956 can be at respective fifth and sixth locations which are laterally spaced from one another along a third lateral dimension. The seventh opening 1958 and the eight opening 1960 can be at respective seventh and eighth locations which are laterally spaced from one another along a fourth lateral dimension. The four pairs of openings can be distributed along a length of the surgical pad 1940. In some examples, the first, second, third and fourth lateral dimensions are parallel to one another. In some examples, the first, second, third and fourth lateral dimensions can be evenly spaced from one another. In some examples, respective openings of each pair of openings can aligned. For example, the first, third, fifth and seventh openings can be aligned with one another along a first longitudinal dimension perpendicular to the first, second, third and fourth lateral dimensions. The second, fourth, sixth and eighth openings can be aligned with one another along a second longitudinal dimension parallel with the first longitudinal dimension and perpendicular to the first, second, third and fourth lateral dimensions. The first and second longitudinal dimensions can be parallel or substantially parallel to the longer opposing edges 1962, 1966. A surgical pad can comprise more or fewer pairs of openings.

The first surgical cord 1970 and the second surgical cord 1980 can comprise respective portions 1972, 1982 configured to be positioned over the surgical pad 1940. The respective portions 1972, 1982 can be used to secure the first surgical cord 1970 and the second surgical cord 1980 to one another over the surgical pad 1940. In some examples, the first surgical cord 1970 and the second surgical cord 1980 can form a pair of surgical cords such that the respective portions 1972, 1982 can be intertwined together to form a knot 1990 over the surgical pad 1940. For example, the first surgical cord 1970 and the second surgical cord 1980 can extend from within the target tissue. The first and second surgical cords 1970, 1980 can be threaded through the surgical pad 1940 from the first surface 1942 through a first opening 1946 and a second opening 1948, respectively, to the second surface 1944 of the surgical pad 1940, such that the respective portions 1972, 1982 of the first surgical cord 1970 and 1980 can be positioned over the second surface 1944 of the surgical pad 1940.

In some examples, additional surgical cords can be coupled to the surgical pad 1940. Each of the plurality of openings 1946, 1948, 1950, 1952, 1954, 1956, 1958, 1960 can allow extension therethrough of a corresponding surgical cord. In some examples, three additional pairs of surgical cords can be coupled to the surgical pad 1940, such as a surgical cord for each of the remaining openings to provide three pairs of surgical cords. A corresponding pair of surgical cords can be threaded through each of the remaining pairs of openings, and the surgical cords of each pair can be secured to one another to form a respective knot over the surgical pad 1940. For example, the first and second openings 1946, 1948, the third and fourth openings 1950, 1952, the fifth and sixth openings 1954, 1956, and the seventh and eighth openings 1958, 1960 can allow extension therethrough of a first, second, third and fourth pair of surgical cords, respectively. Each pair of surgical cords can be secured to one another, such as to form a respective knot, over the second surface 1944 of the surgical pad 1940, such that four knots can be formed over the surgical pad 1940.

Securing the first surgical cord 1970 and the second surgical cord 1980 to the surgical pad 1940 can facilitate desired tensioning of the surgical cords 1970, 1980. In some examples, adjustment in the tension of the surgical cords 1970, 1980 may be desired after the surgical cords 1970, 1980 have already been secured to the surgical pad 1940. Re-securing the surgical cords 1970, 1980 to the surgical pad 1940 to adjust tension exerted on the surgical cords 1970, 1980 may be difficult. For example, untying and retying the knot 1990 may be infeasible. In some examples, the spacer 1910 can be positioned between the surgical pad 1940 and the target tissue to provide an additional separation between the surgical pad 1940 and the target tissue. Providing the added separation between the surgical pad 1940 and the target tissue can facilitate adjustment in the tension of the surgical cords 1970, 1980, such as to provide added tension to the first surgical cord 1970 and the second surgical cord 1980. The spacer 1910 can be configured to provide a desired separation between the surgical pad 1940 and the target tissue so as to provide the desired additional tension to the surgical cords 1970, 1980. Inserting the spacer 1910 between the surgical pad 1940 and the target tissue can position the surgical pad 1940 further away from the target tissue, positioning the knot 1990 further away from the target tissue, and thereby adding to the tension exerted upon the surgical cords 1970, 1980.

As shown in FIG. 19A, the spacer 1910 can comprise a respective protrusion, such as elongate portions, configured to be positioned below portions of the surgical pad 1940 on each of two opposing sides of each of the pairs of openings. For example, the spacer 1910 can comprise two protrusions which have the same or a similar orientation, and which extend from a perpendicular or substantially perpendicular portion 1928, where the two protrusions can be positioned to each of two opposing sides of the pairs of openings on the surgical pad 1940. In some examples, the two protrusions can comprise an orientation parallel or substantially parallel to the first and second longitudinal dimensions.

The spacer 1910 can be positioned between the surgical pad 1940 and target tissue such that a first surface 1930 of the spacer 1910 is oriented toward the target tissue and a second surface 1932, such as a second opposing surface, of the spacer 1910 is oriented toward the surgical pad 1940. For example, the first surface 1930 of the spacer 1910 can be positioned over the target tissue, such as adjacent to and in contact with the target tissue. The second surface 1932 of the spacer 1910 can be adjacent to and in contact with the first surface 1942 of the surgical pad 1940.

Referring to FIG. 19B, the spacer 1910 can comprise a first elongate portion 1912 and a second elongate portion 1914 and an intermediate portion 1916 extending between the same end portion of each of the first and second elongate portions 1912, 1914. In some examples, the spacer 1910 can comprise a U-shape. For example, an outer edge 1918 of the spacer 1910 can comprise a first edge portion 1920, a second edge portion 1922 and a third edge portion 1924, which form three sides of a rectangular or substantially rectangular shape. The spacer 1910 can have a fourth edge portion 1926 comprising an indentation, for example comprising a U-shaped indentation, configured to be positioned below a portion of the surgical pad 1940 partially surrounding the pairs of openings. The space provided by the indentation can allow extension of the surgical cords between the target tissue and the surgical pad 1940. For example, the first and third edge portions 1920, 1924 can have opposing orientations and can define the outer edges of the elongate portions 1912, 1914. The second edge portion 1922 can extend between a respective end of the first and third edge portions 1920, 1924, and define an outer edge of the intermediate portion 1916. The fourth edge portion 1926 can extend between respective ends of the first and third edge portions 1920, 1926 and define the indentation configured to be positioned so as to partially surround the pairs of openings in the surgical pad 1940.

As shown in FIG. 19A, the first elongate portion 1912 can be configured to be positioned below a portion of the surgical pad 1940 to a first side of the pairs of openings. The second elongate portion 1914 can be configured to be positioned to a second side of the pairs of openings, the second side being oriented away from the first side. For example, the first and second sides can have opposing orientations. The first elongate portion 1912 and the second elongate portion 1914 can have an orientation parallel or substantially parallel to the first and second longitudinal dimensions. The U-shaped space formed by the indentation on the fourth edge portion 1926 can be positioned below and in alignment with the pairs of openings such that any surgical cords can extend between the target tissue and the surgical pad 1940. For example, the surgical pad 1940 can be positioned over an opening formed in the target tissue, including a closed and/or sealed opening. One or more pairs of surgical cords (e.g., tethers) can extend from the opening and be secured to the surgical pad 1940. The surgical pad 1940 and the spacer 1910 can be positioned such that the U-shaped space formed by the indentation on the fourth edge portion 1926 are in alignment with the opening to allow extension of the surgical cords between the opening and corresponding openings on the surgical pad 1940.

In some examples, the spacer 1910 can be positioned such that its first edge portion 1920 can have the same or similar orientation as the first edge portion 1962 of the surgical pad 1940. The second edge portion 1922 of the spacer 1910 can have the same or similar orientation as the second edge portion 1964 of the surgical pad 1940, and the third edge portion 1924 of the spacer 1910 can have the same or similar orientation as the third edge portion 1966 of the surgical pad 1940. In some examples, the first edge portion 1920 can be aligned with the first edge portion 1962, the second edge portion 1922 can be aligned with the second edge portion 1964 and the third edge portion 1924 can be aligned with the third edge portion 1966.

Referring to FIG. 19C, the spacer 1910 can have a uniform or substantially uniform thickness. Inserting a spacer having a uniform or substantially uniform thickness between the surgical pad 1940 and the target tissue can provide uniform spacing between the surgical pad 1940 and the target tissue, thereby facilitating uniform adjustment in the tension of any surgical cords secured to the surgical pad 1940. The thickness can be a dimension extending between opposing portions of the first surface 1942 and the second surface 1944, such as a dimension perpendicular or substantially perpendicular to the first surface 1942 and/or the second surface 1944. The thickness can be selected based on a desired separation between the target tissue and the surgical pad 1940, such as to provide a desired adjustment in the tension of the first and second surgical cords 1970, 1980. In some examples, the spacer 1910 can comprise a non-uniform thickness.

Figures 20A, 20B, 20C:
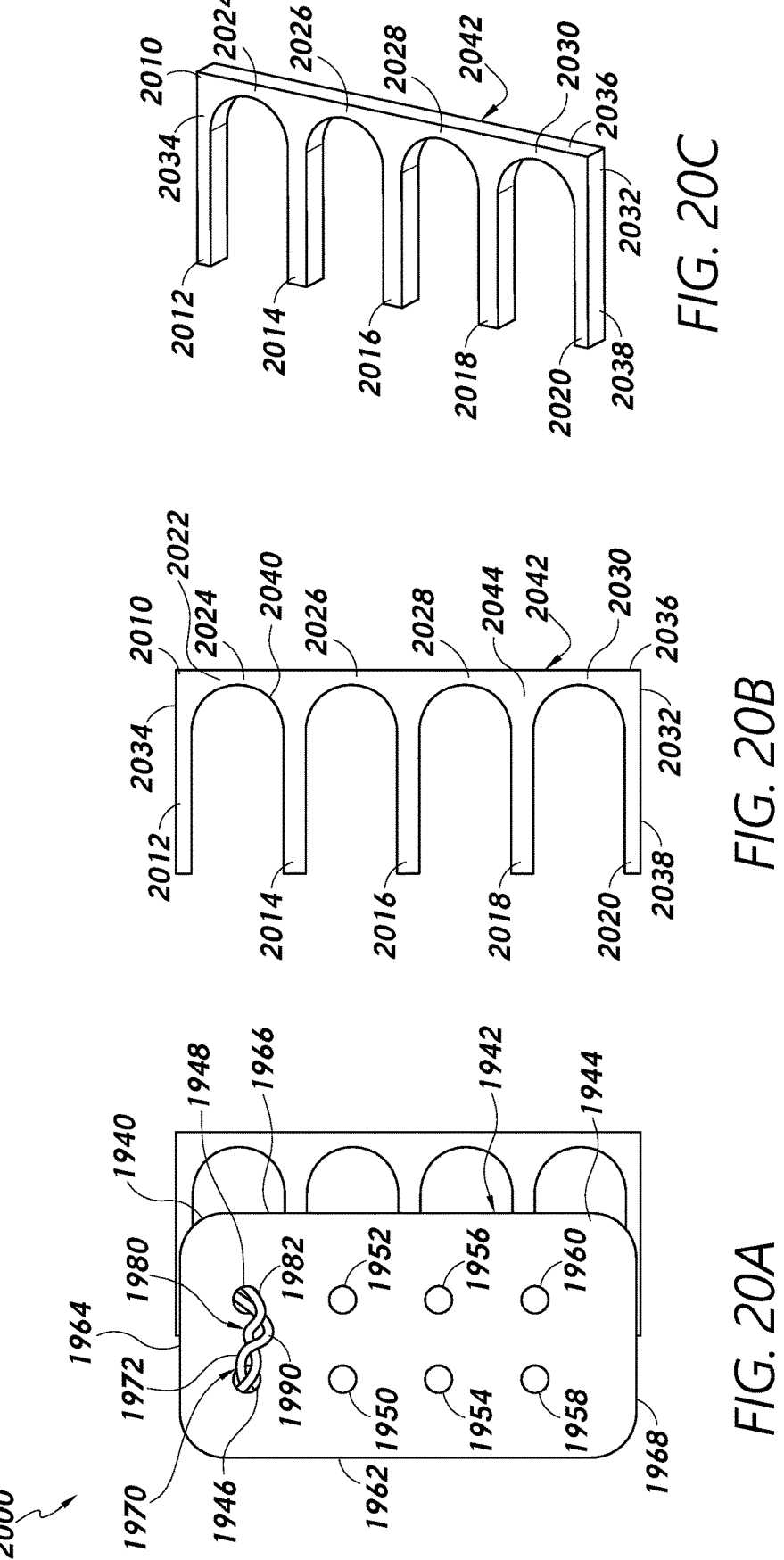
FIGS. 20A and 20B are top-down plan views of an example of a suture system and a spacer of the suture system, respectively.
FIG. 20C is a perspective view of the spacer of FIGS. 20A and 20B.

FIGS. 20A, 20B and 20C show an example a suture system 2000 comprising the surgical pad 1940 and the first and second surgical cords 1970, 1980, as described with reference to FIG. 19, and another example of a spacer 2010. A top-down plan view of the spacer 2010 is shown in FIG. 20B, and a perspective view of the spacer 2010 is shown in FIG. 20C. Positioning of the surgical pad 1940 and/or the surgical cords 1970, 1980, such as relative to the target tissue, can be as described with reference to FIG. 19. The spacer 2010 can comprise a plurality of protrusions having the same or a similar orientation. The plurality of protrusions can be at regular intervals and be evenly spaced from one another. A respective protrusion can be configured to be positioned between adjacent pairs of openings of the surgical pad 1940. FIG. 20A shows a top-down plan view of the surgical pad 1940 positioned over the spacer 2010, and the respective portions 1972, 1982 of the first surgical cord 1970 and second surgical cord 1980 secured to one another, such as in a knot 1990, over the surgical pad 1940.

The spacer 2010 can be configured to be positioned between the surgical pad 1940 and a target tissue to facilitate desired tension in the first and second surgical cords 1970, 1980. The spacer 2010 can have a first surface 2042, such as a bottom surface, configured to be oriented toward the target tissue, and away from the surgical pad 1940. For example, the first surface 2042 can be configured to be positioned adjacent to and in contact with the target tissue. The spacer 2010 can have a second surface 2042, such as a top surface, configured to be oriented toward the surgical pad 1940. The second surface 2044 can have an opposing orientation relative to the first surface 2042. For example, the second surface 2044 can be configured to be positioned adjacent to and in contact with the first surface 1942 of the surgical pad 1940.

The spacer 2010 can comprise a plurality of spaced apart protrusions, such as elongate portions, which extend from a perpendicular portion, the plurality of protrusions having the same or a similar orientation. The plurality of protrusions can be perpendicular or substantially perpendicular to the perpendicular portion. Referring to FIG. 20B, the spacer 2010 can comprise a plurality of elongate portions 2012, 2014, 2016, 2018, 2020 having the same or similar orientation and extending from a perpendicular portion 2022. In some examples, the plurality of elongate portions 2012, 2014, 2016, 2018, 2020 can extend from the perpendicular portion 2022 at regular intervals. For example, the spacer 2010 can comprise a first elongate portion 2012, a second elongate portion 2014, a third elongate portion 2016, a fourth elongate portion 2018, and a fifth elongate portion 2020 extending from the perpendicular portion 2022. The perpendicular portion 2022 can comprise a plurality of intermediate portions 2024, 2026, 2028, 2030, an intermediate portion extending between adjacent elongate portions. For example, a first intermediate portion 2024 can extend between the first elongate portion 2012 and the second elongate portion 2014, a second intermediate portion 2026 can extend between the second elongate portion 2014 and the third elongate portion 2016, a third intermediate portion 2028 can extend between the third elongate portion 2016 and the fourth elongate portion 2018, and a fourth intermediate portion 2030 can extend between the fourth elongate portion 2018 and the fifth elongate portion 2020. In some examples, the spacer 2010 can comprise a plurality of U-shaped portions.

Adjacent elongate portions can be configured to partially surround each pair of openings in the surgical pad 1940. A corresponding elongate portion of the spacer 2010 can be positioned between adjacent pairs of openings of the surgical pad 1940. For example, the second elongate portion 2014 can be positioned between the first pair of openings (1946, 1948) and the second pair of openings (1950, 1952). The third elongate portion 2016 can be positioned between the second pair of openings (1950, 1952) and the third pair of openings (1954, 1956). The fourth elongate portion 2018 can be positioned between the third pair of openings (1954, 1956) and the fourth pair of openings (1958, 1960). In some examples, the first elongate portion 2012 can be positioned to a first side, and the second elongate portion 2014 can be positioned to a second side, of the first pair of openings (1946, 1948). The second side of the first pair of openings (1946, 1948) can be oriented away from the first side, for example having an opposing orientation. In some examples, the fourth elongate portion 2018 can be positioned to a first side, and the fifth elongate portion 2020 can be positioned to a second side, of the fourth pair of openings (1958, 1960). The second side of the fourth pair of openings (1958, 1960) can be oriented away from the first side, for example having an opposing orientation. In some examples, the first elongate portion 2012, second elongate portion 2014, third elongate portion 2016, fourth elongate portion 2018 and fifth elongate portion 2020 can be positioned so as to comprise an orientation parallel or substantially parallel to the lateral dimensions as described with reference to FIG. 19.

In some examples, adjacent elongate portions can be evenly spaced apart. For example, a distance between the first and second elongate portions 2012, 2014 can be the same or similar to a distance between the second and third elongate portions 2014, 2016, between the third and fourth elongate portions 2016, 2018, and between the fourth and fifth elongate portions 2018, 2020. In some examples, the distance between adjacent elongate portions can depend at least in part on the spacing between adjacent pairs of openings of the surgical pad 1940. In some examples, the distance can be irregular.

The spacer 2010 can have an outer edge 2032 comprising three edge portions 2034, 2036, 2038 which can form three sides of a rectangular or substantially rectangular shape. The first edge portion 2034 can be parallel or substantially parallel to the third edge portion 2038. The second edge portion 2036 can extend between a respective end of the first and third edge portions 2034, 2038, and can be perpendicular or substantially perpendicular to the first and third edge portions 2034, 2038. The outer edge 2032 can comprise a fourth edge portion 2040 extending between a respective second end of the first and third edge portions 2034, 2038. The fourth edge portion 2040 can comprise a plurality of indentations spaced therealong. In some examples, an indentation can comprise a U-shape. For example, each of the indentations can comprise a U-shape.

The spacer 2010 can be configured to be positioned between the surgical pad 1940 and the target tissue, such that the first and third edge portions 2034, 2038 of the spacer 2010 can have the same or similar orientation as the second and fourth edge portions 1964, 1968 of the surgical pad 1940. For example, the first and third edge portions 2034, 2038 of the spacer 2010 can be aligned with the second and fourth edge portions 1964, 1968 of the surgical pad 1940. The second edge portion 2036 of the spacer 2010 can have the same or similar orientation as the third edge portion 1966 of the surgical pad 1940. For example, the second edge portion 2036 of the spacer 2010 can align with the third edge portion 1966 of the surgical pad 1940. Alternatively, the second edge portion 2036 of the spacer 2010 can have the same or similar orientation as, such as being aligned with, the first edge portion 1962 of the surgical pad 1940. A respective one of the plurality of indentations on the fourth edge portion 2040 can be aligned with a pair of the plurality of pairs of openings. The U-shaped recess formed by each of the indentation can be configured to be below a pair of the openings.

Referring to FIG. 20C, the spacer 2010 can have a uniform or substantially uniform thickness. Inserting a spacer having a uniform or substantially uniform thickness between the surgical pad 1940 and the target tissue can provide uniform spacing between the surgical pad 1940 and the target tissue, thereby facilitating uniform adjustment in the tension of any surgical cords secured to the surgical pad 1940. In some examples, the monolithic configuration of the spacer 2010 can facilitate adjustment of tension in all of the pairs of surgical cords secured to the surgical pad 1940. Adjustment in tension of all of the pairs can be achieved by inserting one spacer 2010, rather than a plurality of spacers, simplifying the process. The thickness can be a dimension extending between opposing portions of the first surface 2042 and the second surface 2044, such as a dimension perpendicular or substantially perpendicular to the first surface 2042 and/or the second surface 2044. The thickness can be selected based on a desired separation between the target tissue and the surgical pad 1940, such as to provide a desired adjustment in the tension of the first and second surgical cords 1970, 1980. In some examples, the spacer 2010 may not comprise a uniform thickness, for example comprising an elongate portion having a thickness different from one or more other of the elongate portions.

Figure 21C:
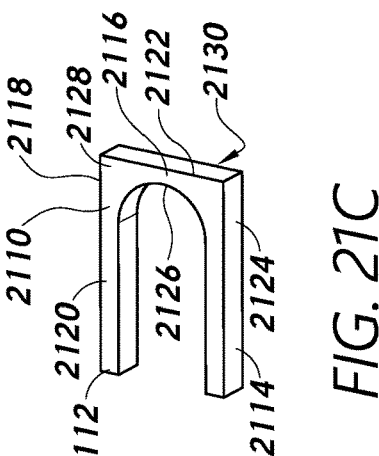
FIG. 21C is a perspective view of the spacer of FIGS. 21A and 21B.
Figure 21B:
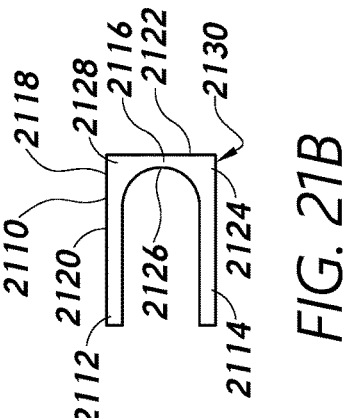
FIGS. 21A and 21B are top-down plan views of an example of a suture system and a spacer of the suture system, respectively.
Figure 21A:
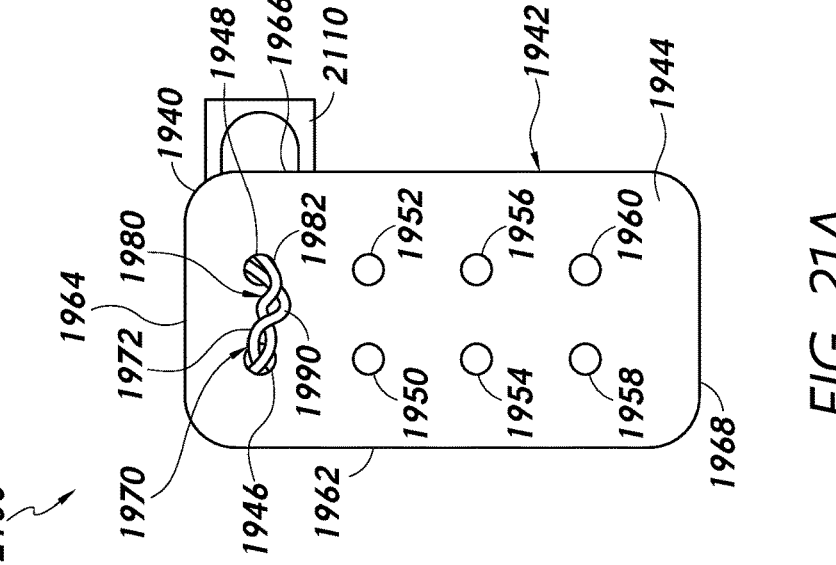

FIGS. 21A, 21B and 21C show an example a suture system 2100 comprising another example of a spacer 2110. The suture system 2100 can comprise the surgical pad 1940 and the first and second surgical cords 1970, 1980, as described with reference to FIG. 19. The spacer 2110 can comprise a respective portion configured to be positioned below opposing sides of two locations to which a pair of surgical cords are secured to the surgical pad 1940. For example, the spacer 2110 can comprise two spaced apart protrusions extending from a perpendicular portion, the protrusions having the same or similar orientation. The two protrusions can be perpendicular or substantially perpendicular to the perpendicular portion. The spacer 2110 can comprise a respective protrusion, such as an elongate portion, configured to be positioned below each of two opposing sides of one pair of openings in the surgical pad 1940. In some examples, the spacer 2110 can comprise a U-shape. The protrusions can be positioned so as to be parallel or substantially parallel to a lateral dimension as described with reference to FIG. 19. FIG. 21A shows a top-down plan view of the surgical pad 1940 positioned over the spacer 2110, and the respective portions 1972, 1982 of the first surgical cord 1970 and second surgical cord 1980 secured to one another, such as in a knot 1990, over the surgical pad 1940. A top-down plan view of the spacer 2110 is shown in FIG. 21B, and a perspective view of the spacer 2110 is shown in FIG. 21C. Positioning of the surgical pad 1940 and/or the surgical cords 1970, 1980, such as relative to the target tissue, can be as described with reference to FIG. 19.

The spacer 2110 can be configured to be positioned between the surgical pad 1940 and a target tissue such that a first surface 2130, such as a bottom surface, configured to be oriented toward the target tissue, and a second surface 2128, such as a top surface, configured to be oriented toward the surgical pad 1940. The second surface 2128 can have an opposing orientation relative to the first surface 2130. The first surface 2130 can be configured to be positioned adjacent to and in contact with the target tissue and the second surface 2128 can be configured to be positioned adjacent to and in contact with the surgical pad 1940.

As shown in FIG. 21A, the spacer 2110 can be configured to be positioned to partially surround one pair of openings in the surgical pad 1940. For example, the spacer 2110 can be configured to be positioned below a portion of the surgical pad 1940 which partially surrounds a pair of the openings. The spacer 2110 can comprise two elongate portions which have the same or a similar orientation, and which extend from a perpendicular or substantially perpendicular portion, where the two elongate portions can be positioned to each of two opposing sides of a pair of openings.

As described herein, the spacer 2110 can comprise two spaced apart protrusions extending from a perpendicular portion, the protrusions having the same or a similar orientation. Referring to FIG. 21B, for example, the spacer 2110 can comprise a first elongate portion 2112 and a second elongate portion 2114. An intermediate portion 2116 can extend between the same end portion of each of the first and second elongate portions 2112, 2114. The intermediate portion 2116 can be the perpendicular or substantially perpendicular to the intermediate portion 2116. The first elongate portion 2112 and second elongate portion 2114 can extend from the same side of the intermediate portion 2116. While the spacer 2110 is at its desired position, the first elongate portion 2112 and the second elongate portion 2114 can be parallel or substantially parallel to the lateral dimensions described with reference to FIG. 19.

The spacer 2110 can comprise an outer edge 2118 a first edge portion 2120, a second edge portion 2122 and a third edge portion 2124, which form three sides of a rectangular or substantially rectangular shape. The spacer 2110 can have a fourth edge portion 2126 comprising an indentation, for example comprising a U-shaped indentation, configured to be positioned below a portion of the surgical pad 1940 partially surrounding a pair of openings. The fourth edge portion 2126 can extend between respective ends of the first and third edge portions 2120, 2124 and define the indentation configured to be positioned so as to partially surround the pair of openings in the surgical pad 1940.

The first elongate portion 2112 can be configured to be positioned below a portion of the surgical pad 1940 to a first side of a pair of openings. The second elongate portion 2114 can be configured to be positioned to a second side of the pair of openings, the second side being oriented away from the first side. For example, the first and second sides can have opposing orientations. The U-shaped space formed by the indentation on the fourth edge portion 2126 can be positioned below the pair of openings. The space between the first and second elongate portions 2112, 2114 can be aligned with the pair of openings in the surgical pad 1940 to allow extension of the surgical cords 1970, 1980 between the target tissue and the surgical pad 1940. The spacer 2110 can be positioned such that its second edge portion 2122 can have the same or similar orientation as the third edge portion 1966 of the surgical pad 1940, including being aligned with the third edge portion 1966 of the surgical pad 1940. Alternatively, second edge portion 2122 can have the same or similar orientation as the first edge portion 1962 of the surgical pad 1940, including being aligned with the first edge portion 1962. At least a portion of the first and second elongate portions 2112, 2114 can be configured to be positioned below the surgical pad 1940. In some examples, the first and second elongate portions 2112, 2114 can be configured to be positioned entirely below the surgical pad 1940.

FIG. 21A shows the spacer 2110 positioned below the surgical pad 1940 to partially surround the first pair of openings (1946, 1948). In some examples, the spacer 2110 can be configured to be positioned below the surgical pad 1940 to partially surround another pair of openings, such as the second pair of openings (1950, 1952), third pair of openings (1954, 1956) or fourth pair of openings (1958, 1960).

The suture system 2100 can comprise a plurality of the spacers 2110. A plurality of the spacers 2110 can be positioned between the surgical pad 1940 and the target tissue. For example, one spacer 2110 can be positioned to partially surround around one pair of openings each of the pairs of openings such that four spacers 2110 are positioned side by side between the surgical pad 1940 and the target tissue. The plurality of spacers 2110 can share a horizontal plane.

FIG. 21C shows a perspective view of the spacer 2110. The spacer 2110 can have a uniform or substantially uniform thickness. The thickness can be a dimension extending between opposing portions of the first surface 2130 and the second surface 2128, such as a dimension perpendicular or substantially perpendicular to the first surface 2130 and/or second surface 2128. The thickness can be selected based on a desired separation between the target tissue and the surgical pad 1940, such as to provide a desired adjustment in the tension of the first and second surgical cords 1970, 1980. As described herein, a respective spacer 2110 can be positioned to partially surround a pair of the plurality of pairs of openings in the surgical pad 1940, facilitating providing a different separation between the target tissue and each of the pairs of openings to provide a different tension adjustment for each pair of surgical cords secured to the surgical pad 1940.

In some examples, a suture system can comprise a plurality of the one or more of the spacers 1910, 2010, 2110 described with reference to FIGS. 19 through 21. A plurality of spacers can be positioned one over the other. The plurality of spacers can share a vertical plane, such as a plane perpendicular or substantially perpendicular to a surface of the target tissue over which the spacers are positioned. A plurality of spacers can be stacked between a surgical pad and the target tissue to provide a desired separation between the surgical pad and the target tissue so as to facilitate desired adjustment in the tension of respective surgical cords.

It will be understood that a spacer can comprise other configurations. For example, at least a portion of an outer edge of the spacer can depend at least in part on a shape of a surgical pad under which the spacer is positioned. In some examples, at least a portion of the outer edge of the spacer can be the same as or similar to that of the surgical pad, such as so as to facilitate alignment of edges of the spacer and the surgical pad. In some examples, the one or more indentations of the spacer can comprise a shape other than a U-shape. The shape of an indentation can be predetermined to facilitate extension of surgical cords between the target tissue and the surgical pad.

Figure 22B:
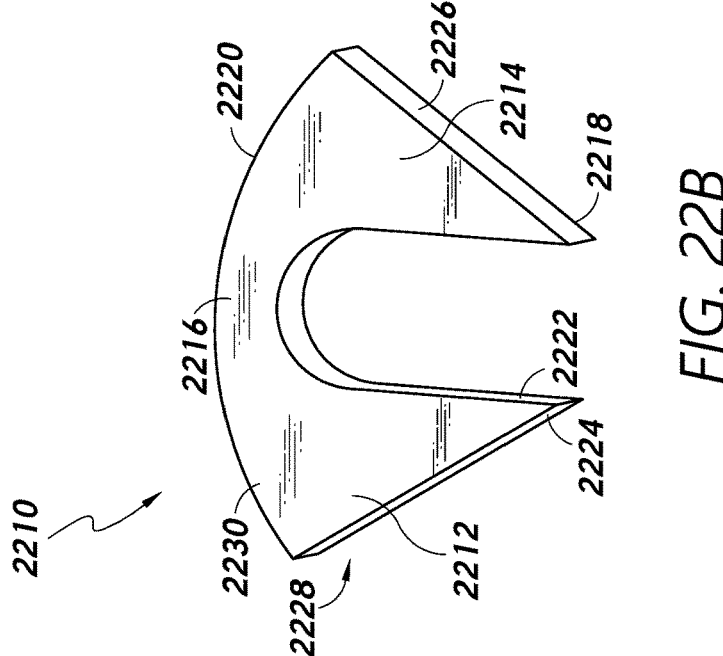
FIG. 22B is a perspective view of the spacer of FIG. 22A.
Figure 22A:
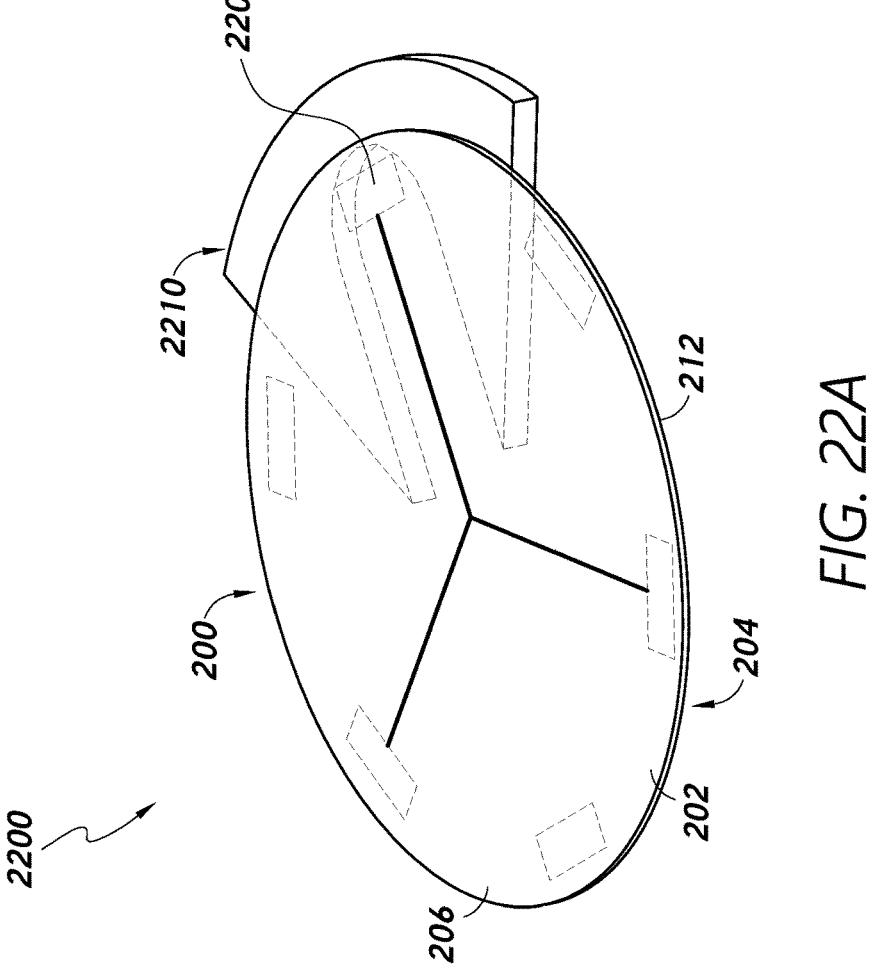
FIG. 22A is a perspective view of an example of a suture system comprising a spacer.

One or more other surgical pads described herein can be used together with a spacer. FIGS. 22 through 27 show examples of spacers which can be used in combination with one or more other surgical pads as described within. Referring to FIG. 22A, an example of a suture system 2200 comprising the surgical pad 200 as described herein, and a spacer 2210 which can be used in combination with the surgical pad 200 is shown. FIG. 22B shows the spacer 2210 in further detail. The spacer 2210 can be configured to be positioned between a target tissue and the surgical pad 200. Referring to FIG. 22A, the spacer 2210 can be positioned below, including below and in contact with, a portion of the surgical pad 200 that at least partially surrounds a designated location 220 on the surgical pad 200. The spacer 2210 can comprise two spaced apart protrusions, such as wedge-shaped protrusions, extending in a same or similar orientation and an intermediate portion extending between the two protrusions. Each of the two protrusions can be configured to be positioned on each of two different sides of the designated location 220, such as two sides having opposing orientations.

Referring to FIG. 22B, the spacer 2210 can have a first surface 2228 and a second surface 2230, such as a second surface having an opposing orientation. The first surface 2228 can be a bottom surface configured to be oriented toward the target tissue, and the second surface 2230 can be a top surface configured to be oriented toward the surgical pad 200. For example, the first surface 2228 can be configured to be positioned adjacent to and in contact with the target tissue and the second surface 2230 can be configured to be positioned adjacent to and in contact with the surgical pad 200, such as a first surface 204 of the flexible pad portion 202 of the surgical pad 200. The second surface 206 of the flexible pad portion 202 can be oriented away from the spacer 2210 and the target tissue.

The spacer 2210 can comprise a first wedge portion 2212 and a second wedge portion 2214 spaced from one another, and an intermediate portion 2216 coupling the first wedge portion 2212 and the second wedge portion 2214. In some examples, the first wedge portion 2212 and the second wedge portion 2214 can be oriented toward one another and extend from the same side of the intermediate portion 2216. In some examples, the intermediate portion 2216 can comprise a curved configuration. The intermediate portion 2216 can extend between a same end portion of the first and second wedge portions 2212, 2214 such that the separation between the first and second wedge portions 2212, 2214 can form a U-shape. For example, the first wedge portion 2212 and the second wedge portion 2214 can have a same or similar orientation such that a separation between the first wedge portion 2212 and the second wedge portion 2214 can form a U-shape. In some examples, the shape of the wedge portions 2212, 2214 and/or the curvature of the intermediate portion 2116 can facilitate placement of the spacer 2210 under the surgical pad 200. For example, a curvature of the intermediate portion 2116 and/or the size and/or shape of the wedge portions 2212, 2214 can be predetermined to facilitate positioning of the spacer 2210 between the surgical pad 200 and the target tissue, while avoiding or reducing interference with any surgical cords extending between the target tissue and the surgical pad 200.

The spacer 2210 can have an outer edge 2218 comprising a curved edge portion 2220 defining the bases of the first and second wedge portions 2212, 2214 and a portion of the intermediate portion 2216 configured to be oriented away from the designated location 220. The outer edge 2218 can have a U-shaped edge portion 2222 defining the separation between the first wedge portion 2212 and the second wedge portion 2214. A first linear or substantially linear portion 2224 and a second linear or substantially linear portion 2226 can extend between respective ends of the curved edge portion 2220 and the U-shaped edge portion 2222 such that the linear or substantially linear portions and the U-shaped edge portion 2222 meet at respective apexes of the first and second wedge portions 2212, 2214.

The spacer 2210 can be positioned relative to the surgical pad 200 such that a portion of the spacer 2210 is positioned to each of two sides of a designated location 220, such as two opposing sides. For example, the first wedge portion 2212 can be positioned to a first side of a designated location 220 and the second wedge portion 2214 can be positioned to a second side of the designated location 220 opposite that of the first side. The first and second wedge portions 2212, 2214 can be positioned below portions of the surgical pad 200 between adjacent designated locations 220. In some examples, the spacer 2210 can be positioned between the surgical pad 200 and the target tissue such that the curved edge portion 2220 has the same or similar orientation as the outer edge 212 of the surgical pad 200. In some examples, the curved edge portion 2220 can be configured to be aligned with the outer edge 212 of the surgical pad 200. The designated location 220 can be positioned within the space defined by the U-shaped edge portion 2222 such that the spacer 2210 can partially surround the designated location 220.

A surgical cord extending from within the target tissue can be coupled to the designated location 220. In some examples, a pair of surgical cords can extend from within the target tissue and be coupled to a designated location 220. In some examples, the surgical cord can comprise a tether as described herein. For example, a pair of tethers extending through an opening in the target can be coupled to the designated location 220, as described herein. While the spacer 2210 is in its desired position, the space between the first and second wedge portions 2112, 2114, such as the U-shaped space, can be aligned with the designated location 220 such that pair of tethers can extend between the target tissue and the surgical pad 200. Note that the tethers are not shown in FIG. 22A for simplicity.

In some examples, one or more protrusions of the spacer 2210 can comprise a shape other than a wedge portion. The one or more protrusions can comprise any number of shapes configured to provide desired separation between the surgical pad 200 and the target tissue, including a rounded shape and/or a polygonal shape.

In some examples, the spacer 2210 can have a uniform or substantially uniform thickness. The thickness can be a dimension extending between opposing portions of the first surface 2228 and the second surface 2230, such as a dimension perpendicular or substantially perpendicular to the first surface 2228 and/or the second surface 2230. In some examples, the spacer 2210 can comprise a non-uniform thickness.

Figures 23A, 23B:
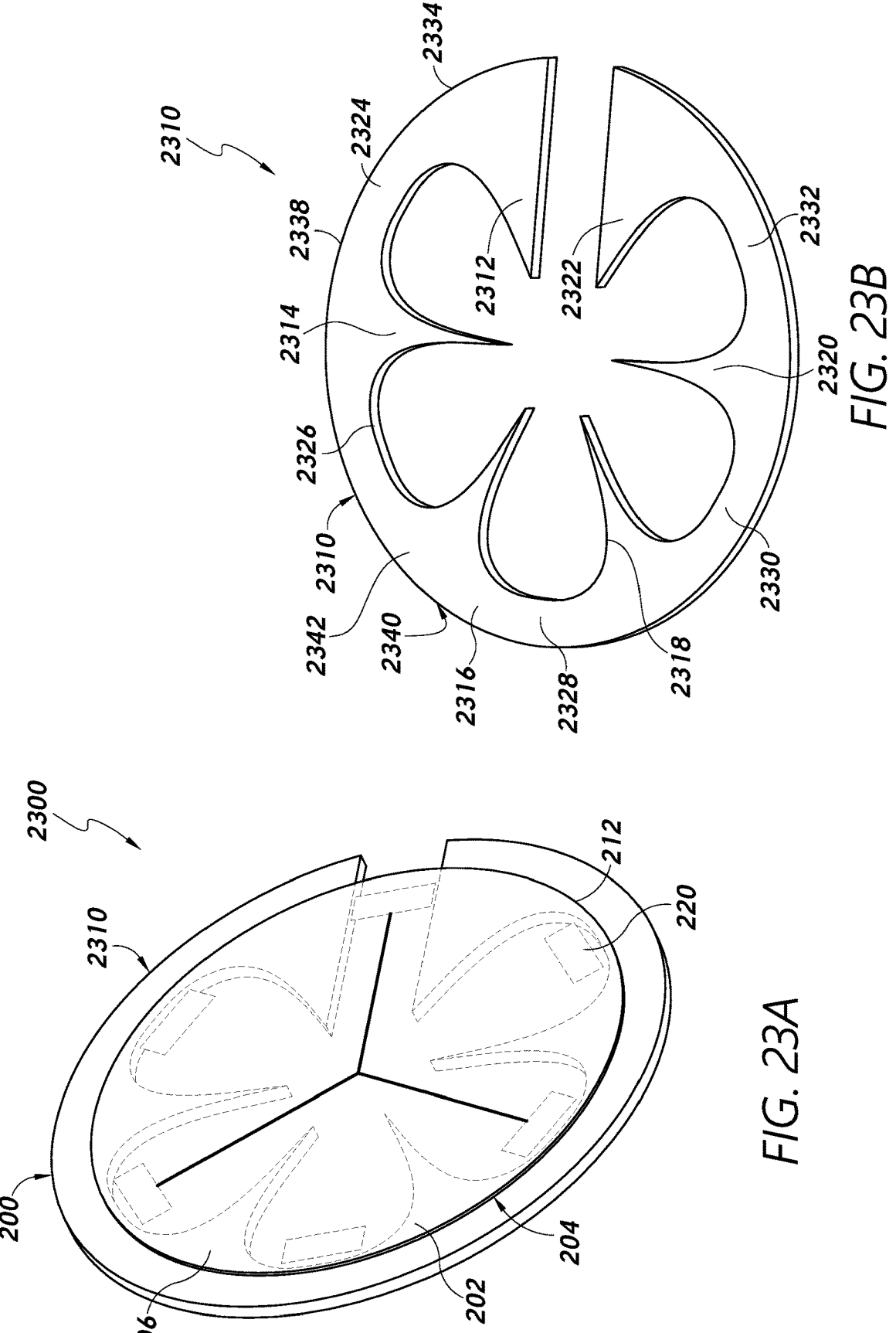
FIG. 23A is a perspective view of an example of a suture system comprising a spacer.
FIG. 23B is a perspective view of the spacer of FIG. 23A.

FIGS. 23A and 23B show an example of a suture system 2300 comprising the surgical pad 200 and a spacer 2310 comprising a plurality of spaced-apart protrusions, each protrusion being configured to be positioned below a corresponding portion of the surgical pad 200 between two adjacent designated locations 220. In some examples, a protrusion can comprise a wedge shape. The spacer 2310 can comprise a partial ring shape that includes a plurality of wedge-shaped protrusions extending from around an inner edge of the partial ring. FIG. 23A shows the spacer 2310 positioned below the surgical pad 200. For example, the surgical pad 200 can be positioned over the target tissue and the spacer 2310 can be positioned below the surgical pad 200 such that it is between the surgical pad 200 and the target tissue. Each spacing between a pair of adjacent protrusions can be aligned with a respective designated locations 220 on the surgical pad 200.

Referring to FIG. 23B, the spacer 2310 can have a first surface 2340 and a second surface 2342, such as a second opposingly oriented surface. The first surface 2340 can be a bottom surface configured to be oriented toward, including being adjacent to and in contact with, the target tissue, and the second surface 2342 can be a top surface configured to be oriented toward, including being adjacent to and in contact with, the surgical pad 200. For example, the second surface 2342 of the spacer 2310 can be configured to be adjacent to and in contact with the first surface 204 of the flexible pad portion 202 of the surgical pad 200. The second surface 206 of the flexible pad portion 202 can be oriented away from the spacer 2310 and the target tissue.

As described herein, the spacer 2310 can comprise a partial ring shape which includes a plurality of spaced apart protrusions each comprising a wedge shape and extending from around an inner edge of the partial ring. In some examples, the spacer 2310 can comprise a plurality of wedge portions 2312, 2314, 2316, 2318, 2320, 2322 coupled to one another in a circular or substantially circular configuration, where a respective apex of each of the wedge portions 2312, 2314, 2316, 2318, 2320, 2322 can be oriented toward one another. For example, the apexes can be oriented toward a center portion of the circle. The spacer 2310 can comprise a plurality of intermediate portions 2324, 2326, 2328, 2330, 2332 coupling the wedge portions 2312, 2314, 2316, 2318, 2320, 2322 to one another. For example, a first intermediate portion 2324 can extend between the first wedge portion 2312 and the second wedge portion 2314, a second intermediate portion 2326 can extend between the second wedge portion 2314 and the third wedge portion 2316, a third intermediate portion 2328 can extend between the third wedge portion 2316 and the fourth wedge portion 2318, a fourth intermediate portion 2330 can extend between the fourth wedge portion 2318 and the fifth wedge portion 2320, and a fifth intermediate portion 2332 can extend between the fifth wedge portion 2320 and the sixth wedge portion 2322. In some examples, the wedge portions 2312, 2314, 2316, 2318, 2320, 2322 can be oriented toward one another and extend from the same side of the intermediate portions 2324, 2326, 2328, 2330, 2332. In some examples, the intermediate portion 2324, 2326, 2328, 2330, 2332 can each comprise a curved configuration.

The spacer 2310 can have an outer edge 2334 comprising a curved edge portion 2338 configured to be oriented similarly or the same as the outer edge 212 of the flexible pad portion 202 of the surgical pad 200. In some examples, the curved edge portion 2336 can be configured to align with the outer edge 212. For example, the surgical pad 200 can comprise a circular or substantially circular shape and the curved edge portion 2338 can comprise a segment of a circular or substantially circular shape.

The outer edge 2334 can comprise a second edge portion, such as an inner edge portion 2336, comprising a plurality of indentations. For example, the inner edge portion 2336 can comprise recesses defined at least in part by adjacent wedge portions. Each of the indentations along the inner edge portion 2336 can be positioned below the surgical pad 200 so as to be below a portion of the surgical pad 200 which partially surrounds a corresponding designated location 220 of the surgical pad 200. As described herein, one or more surgical cords, such as a pair of surgical cords (e.g., a pair of tethers) can extend from within the target tissue and be coupled to a designated location 220. For example, a pair of tethers extending through an opening in the target tissue can be coupled to the designated location 220. While the spacer 2310 is in its desired position, each of the plurality of indentations, such as U-shaped indentations, along the inner edge portion 2336 can be aligned with and partially surround a corresponding designated location 220 and be configured to allow extension of surgical cords between the target tissue and the designated location 220. A corresponding indentation along the inner edge portion 2336 can be positioned to partially surround a designated location 220 such that a respective wedge portion is positioned between immediately neighboring designated locations 220. Note that the tethers are not shown in FIG. 23A for simplicity.

In some examples, one or more protrusions of the spacer 2310 can comprise a shape other than a wedge shape. The one or more protrusions can comprise any number of shapes configured to provide desired separation between the surgical pad 200 and the target tissue, including a rounded shape and/or a polygonal shape.

The spacer 2310 can have a uniform or substantially uniform thickness. The thickness can be a dimension extending between opposing portions of the first surface 2340 and the second surface 2342, such as a dimension perpendicular or substantially perpendicular to the first surface 2340 and/or the second surface 2342. In some examples, the spacer 2310 may not comprise a uniform thickness, for example comprising a wedge portion having a thickness different from one or more other of the wedge portions.

Figure 24B:
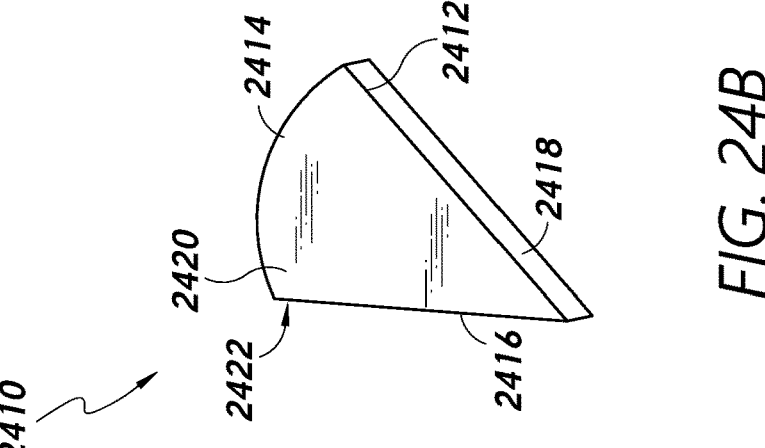
FIG. 24B is a perspective view of the spacer of FIG. 24A.
Figure 24A:
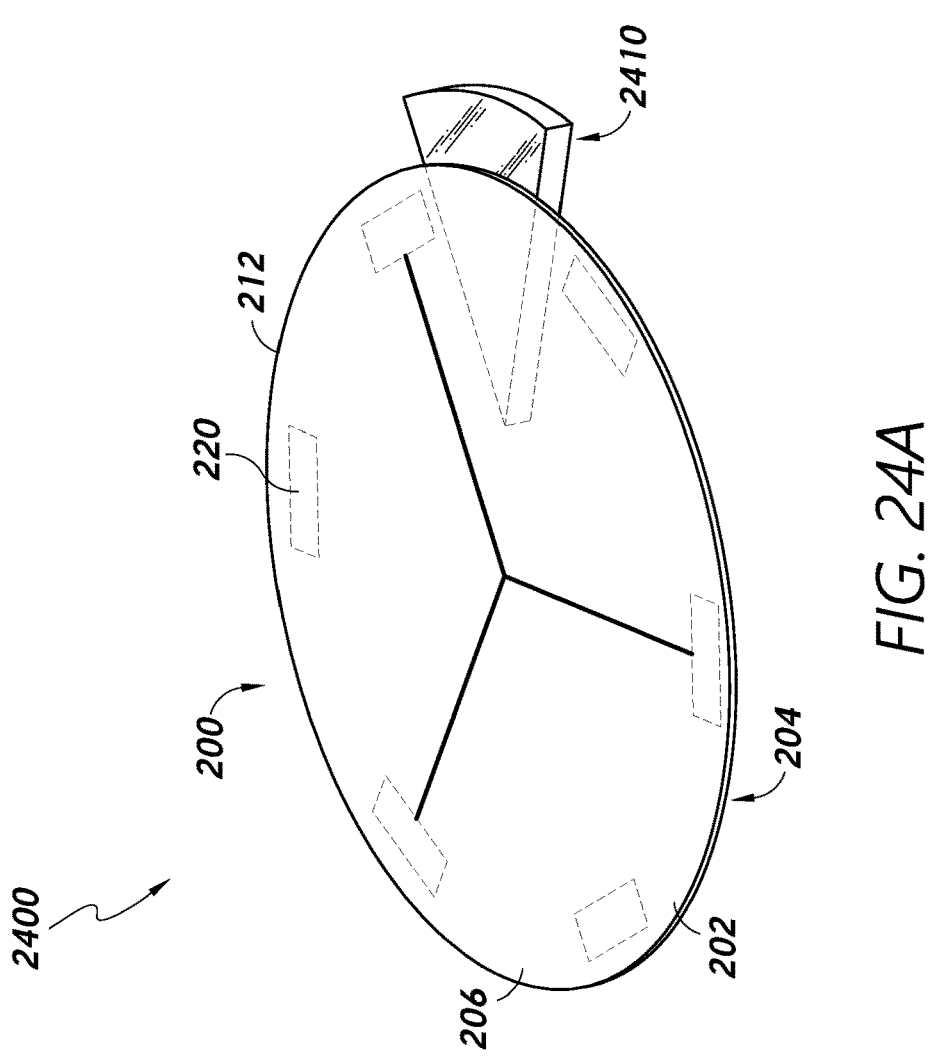
FIG. 24A is a perspective view of an example of a suture system comprising a spacer.

FIGS. 24A and 24B show an example of a suture system 2400 comprising the surgical pad 200 and a spacer 2410 configured to be positioned below a portion of the surgical pad 200 between two adjacent designated locations 220. FIG. 24A shows that the spacer 2410 below the surgical pad 200 between two adjacent designated locations 220. FIG. 24B shows the spacer 2410 in further detail.

The surgical pad 200 can be positioned over a target tissue and the spacer 2410 can be positioned between the surgical pad 200 and the target tissue. The spacer 2410 can have a first surface 2422, such as a bottom surface, configured to be oriented toward the target tissue, such as being adjacent to and in contact with the target tissue. The spacer 2410 can have a second surface 2420, such as a top surface, configured to be oriented away from the target tissue, such as being adjacent to and in contact with the spacer 2410, such as a first surface 204 of the flexible pad portion 202 of the surgical pad 200. The second surface 2422 can have an opposing orientation relative to the first surface 2420.

Referring to FIG. 24B, in some examples, the spacer 2410 can comprise a wedge shape. For example, the spacer 2410 can be a wedge-shaped spacer. The spacer 2410 can comprise an outer edge 2412 comprising a curved edge portion 2414 defining the base of the spacer 2410. The outer edge 2412 can have a first linear or substantially linear portion 2416 and a second linear or substantially linear portion 2418 extending from respective ends of the curved edge portion 2414 and meeting at the apex of the spacer 2410.

In some examples, the spacer 2410 can be positioned between the surgical pad 200 and the target tissue such that the curved edge portion 2414 has the same or similar orientation as the outer edge 212 of the flexible pad portion 202 of the surgical pad 200. In some examples, the curved edge portion 2414 can be configured to be aligned with the outer edge 212. The curvature of the curved edge portion 2414 can be selected based on the curvature of outer edge 212 of the flexible pad portion 202 of the surgical pad 200. For example, the flexible pad portion 202 can comprise a circular or substantially circular shape and the curved edge portion 2414 can comprise a segment of a circular or substantially circular shape. In some examples, the apex of the wedge shape can be oriented toward and/or positioned below a center portion 208 of the flexible pad portion 202.

The spacer 2410 can be positioned between two immediately neighboring designated locations 220, such that the first and second linear or substantially linear edge portions 2416, 2418 can be oriented toward a respective one of the immediately neighboring designated locations 220. As described herein, one or more surgical cords, such as a pair of surgical cords, extending from within the target tissue can be coupled to a designated location 220. In some examples, a pair of tethers can extend from within the target tissue and be coupled to a designated location 220. While the spacer 2410 is in its desired position, the first and second linear or substantially linear edge portions 2416, 2418 can be positioned between adjacent designated locations 220 such that the pair of surgical cords can extend between the target tissue and the surgical pad 200. A corresponding pair of surgical cords can be coupled to each of the immediately neighboring designated locations 220. The spacer 2410 can be positioned between the designated locations 220 such that the two pairs of surgical cords can extend between the target tissue and the surgical pad 200.

In some examples, the spacer 2410 can comprise a shape other than a wedge shape, including a rounded shape and/or a polygonal shape. In some examples, a plurality of the spacers 2410 can be used in combination with the surgical pad 200. For example, a plurality of spacers 2410 can be positioned between the surgical pad 200 and the target tissue, each of the spacers 2410 being positioned between a corresponding pair of adjacent designated locations 220. In some examples, a spacer 2410 can be positioned between each pair of adjacent designated locations 220. Referring to FIG. 24A, the surgical pad 200 can comprise six designated locations 220. The suture system 2400 can comprise six spacers 2410, each spacer 2410 positioned between a corresponding pair of immediately neighboring designated locations 220. For example, the plurality of spacers 2410 can be laterally spaced from one another.

In some examples, the spacer 2410 can have a uniform or substantially uniform thickness. The thickness can be a dimension extending between opposing portions of the first surface 2420 and the second surface 2422, such as a dimension perpendicular or substantially perpendicular to the first surface 2420 and/or the second surface 2422. In some examples, the spacer 2410 can comprise a non-uniform thickness.

Figure 25B:
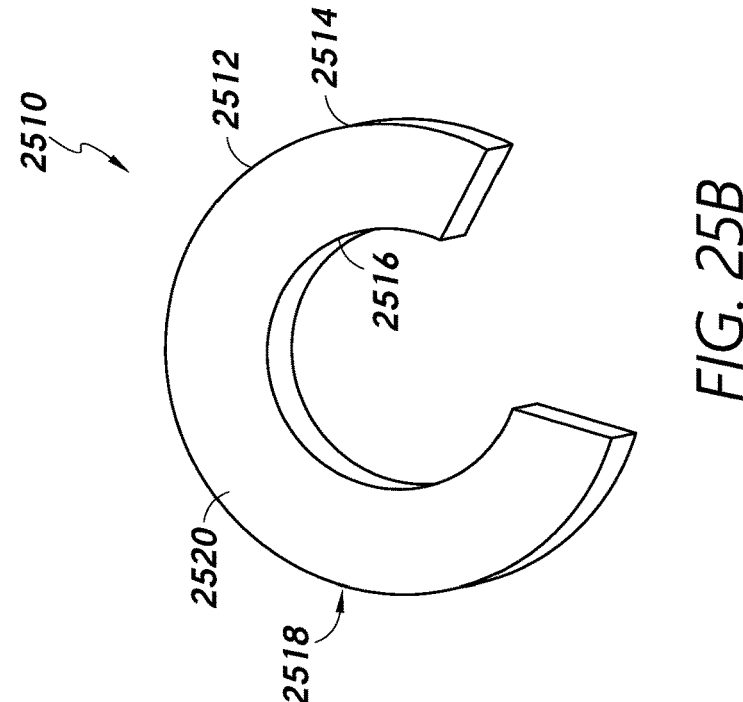
FIG. 25B is a perspective view of the spacer of FIG. 25A.
Figure 25A:
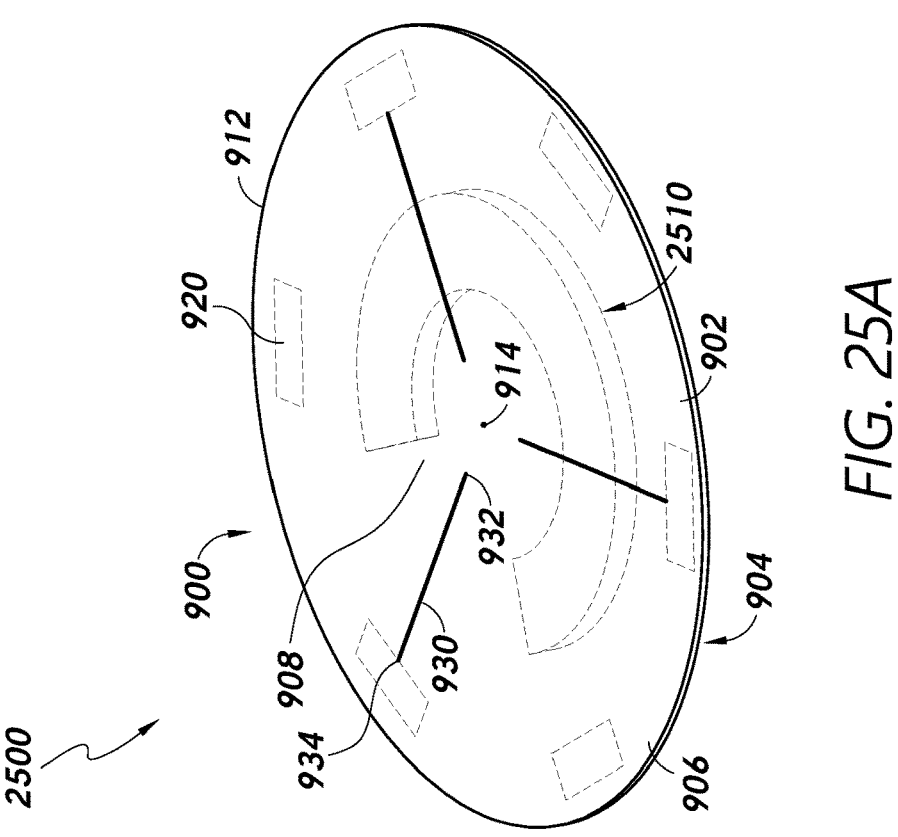
FIG. 25A is a perspective view of an example of a suture system comprising a spacer.

FIGS. 25A and 25B show an example of a suture system 2500 comprising the surgical pad 900 described with reference to FIG. 9, and a spacer 2510 configured to be used in combination with the surgical pad 900. FIG. 25A shows the spacer 2510 positioned below the surgical pad 900. FIG. 25B shows the spacer 2510 in more detail.

As described herein, the surgical pad 900 can comprise a plurality of elongate ribs 930 that are hollow. One or more surgical cords, such as tethers as described herein, configured to be coupled to the surgical pad 900 can be threaded through a respective lumen of one or more of the elongate ribs 930 from a second end 934 to a first end 932. For example, a surgical cord or pair of surgical cords, such as a tether or pair of tethers, can be threaded through a lumen of an elongate rib 930. The tether or pair of tethers can then be fixedly coupled to the surgical pad 900 at or adjacent to the first end 932 of the elongate rib 930. In some examples, the tether or pair of tethers can be fixedly coupled to the surgical pad 900 over and/or at the center portion 908 of the second surface 906. The lumen of each elongate rib 930 can comprise extending therethrough a corresponding tether or pair of tethers. Tethers or pairs of tethers from all of the elongate ribs 930 can be secured over and/or at the center portion 908 of the second surface 906. In some examples, all of the tethers or pairs of tethers coupled to the surgical pad 900 can be knotted together with one another over and/or at the center portion 908 of the second surface 906. For example, the tethers can be secured to a center location 914 of the surgical pad 900. Note that the tethers are not shown in FIG. 25A for simplicity.

The spacer 2510 can be configured to provide a desired separation between the surgical pad 900 and the target tissue. In some examples, the spacer 2510 can be configured to be positioned below the location on the surgical pad 900 at or proximate to which the surgical cords are secured to the surgical pad 900. For example, the spacer 2510 can be at a position between the target tissue and the center portion 908 of the second surface 906.

Referring to FIG. 25B, the spacer 2510 can have a first surface 2518 and a second surface 2520, such as a second opposingly oriented surface. The first surface 2518 can be a bottom surface configured to be oriented toward, including adjacent to and in contact with, the target tissue, and the second surface 2520 can be a top surface configured to be oriented toward, including adjacent to and in contact with, the surgical pad 900. As shown in FIG. 25B, the spacer 2510 can comprise a partial ring shape. The spacer 2510 can comprise an outer edge 2512 comprising a first curved edge portion 2514 and a second curved edge portion 2516. The first curved edge portion 2514 can be oriented toward the outer edge 912 of the surgical pad. The second curved edge portion 2516 can partially surround the portion of the surgical pad 900 to which the surgical cords are secured.

The spacer 2510 can comprise any number of shapes. In some examples, the spacer 2510 can comprise a circular shape. In some examples, the spacer 2510 can comprise a polygonal shape. In some examples, the spacer 2510 can have a uniform or substantially uniform thickness. The thickness can be a dimension extending between opposing portions of the first surface 2518 and the second surface 2520, such as a dimension perpendicular or substantially perpendicular to the first surface 2518 and/or the second surface 2520. In some examples, the spacer 2510 can comprise a non-uniform thickness.

Figure 26B:
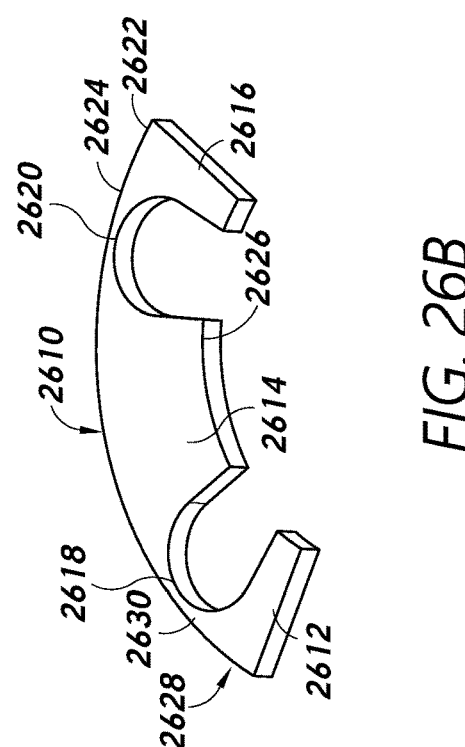
FIG. 26B is a perspective view of the spacer of FIG. 26A.
Figure 26A:
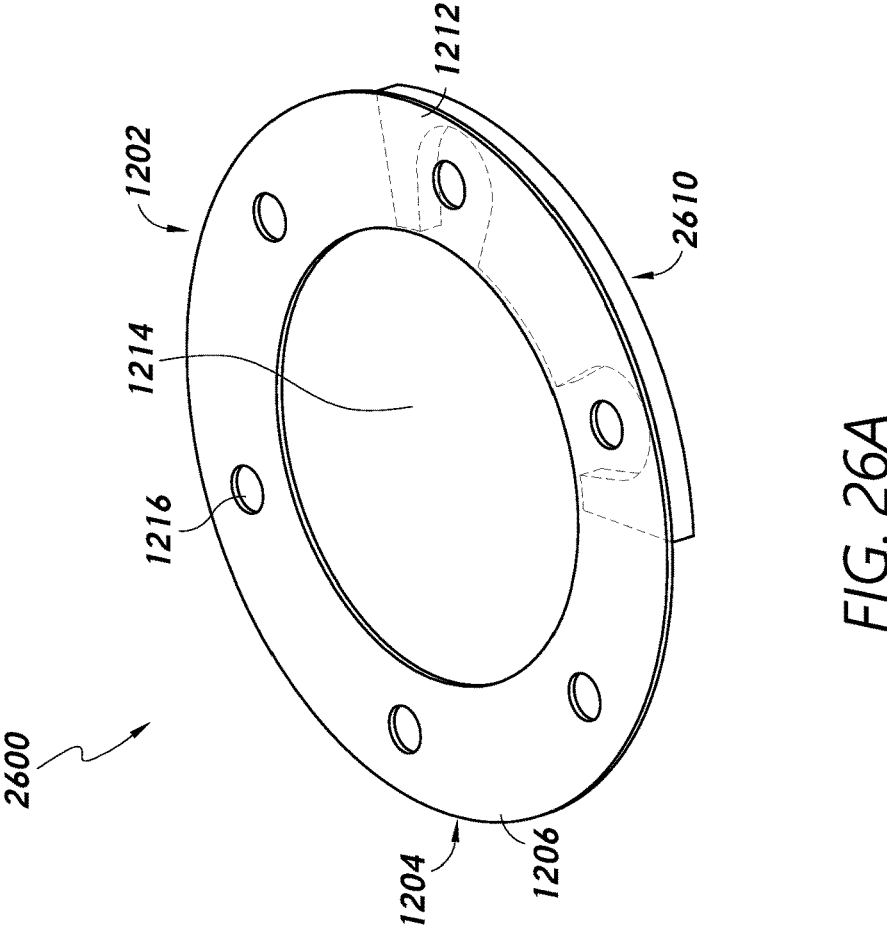
FIG. 26A is a perspective view of an example of a suture system comprising a spacer.

FIGS. 26A and 26B show an example of a suture system 2600 comprising the surgical pad 1202 described with reference to FIGS. 12 through 15, and a spacer 2610 configured to be positioned between the surgical pad 1202 and a target tissue. The spacer 2610 can comprise a partial ring shape having a plurality of spaced-apart portions, each of which being configured to be positioned under a portion of the surgical pad 1202 between adjacent edge openings 1216. As described herein, the surgical pad 1202 can comprise a central opening 1214 and a plurality of edge openings 1216. A plurality of surgical cords can extend through the plurality of edge openings 1216. In some examples, the surgical cords can comprise the anchor cords as described herein. For example, a corresponding anchor cord or pair of anchor cords can extend through each of the plurality of edge openings 1216. The plurality of anchor cords can each comprise a portion configured to be deployed into the target tissue and another portion configured to be extending externally of the target tissue and through the plurality of edge openings 1216. A portion of a respective anchor cord or pair of anchor cords can comprise a portion extending externally of the target tissue and configured to extend through an edge opening 1216. The plurality of anchor cords can be tensioned and secured to reduce the size of the opening and/or seal the opening in the target tissue. Note that the anchor cords are not shown in FIG. 26A for simplicity.

Referring to FIG. 26B, the spacer 2610 can have a first surface 2628 and a second surface 2630, such as a second opposingly oriented surface. The first surface 2628 can be a bottom surface configured to be oriented toward, including adjacent to and in contact with, the target tissue, and the second surface 2630 can be a top surface configured to be oriented toward, including adjacent to and in contact with, the surgical pad 1202. The spacer 2610 can comprise a plurality of spaced-apart portions coupled to one another and arranged in a partial-ring configuration, a respective one of the plurality of spaced-apart portions being configured to be positioned below a portion of the surgical pad 1202 between adjacent edge openings 1216.

The spacer 2610 can comprise a first portion 2612, a second portion 2614, and a third portion 2616 coupled to one another in an arcuate configuration, such as a partial ring configuration. The spacer 2610 can comprise a plurality of intermediate portions 2618, 2620 coupling the portions 2612, 2614, 2616 to one another. For example, a first intermediate portion 2618 can extend between the first portion 2612 and the second portion 2614 and a second intermediate portion 2620 can extend between the second portion 2614 and the third portion 2616. Space between adjacent portions can be configured to allow extension of the surgical cords between the target tissue and the surgical pad 1202. In some examples, the first portion 2612, second portion 2614, and third portion 2616 can be oriented toward one another and extend from the same side of the intermediate portions 2618, 2620. In some examples, the intermediate portion 2618, 2620 can each comprise a curved configuration. In some examples, the shape of the first, second and third portions 2612, 2614, 2616 and/or the curvature of the intermediate portions 2618, 2620 can facilitate placement of the spacer 2610 under the surgical pad 1202. For example, a curvature of the intermediate portions 2618, 2620 and/or the size and/or shape of the first, second and third portions 2612, 2614, 2616 can be predetermined to facilitate positioning of the spacer 2610 between the surgical pad 1202 and the target tissue, while avoiding or reducing interference with any surgical cords extending between the target tissue and the surgical pad 1202.

The spacer 2610 can comprise an outer edge 2622 which includes a first edge portion 2624 comprising a curved edge portion. The spacer 2610 can comprise a partial ring shape and the first edge portion 2624 can comprise an outer curvature of the partial ring shape. For example, the spacer 2610 can be configured to be positioned between the target tissue and surgical pad 1202 such that the curved edge portion of the first edge portion 2624 can be oriented similarly or the same as the outer edge 1212 of the surgical pad 1202 while the spacer 2610 is in the desired position. In some examples, the curved edge portion can comprise a curvature the same as or similar to that of the curvature of the outer edge 1212. In some examples, the curved edge portion can comprise a segment of a circle.

The outer edge 2622 can comprise a second edge portion 2626. In some examples, the second edge portion 2626 can comprise an opposing orientation relative to that of the first edge portion 2624. The second edge portion 2626 can comprise a plurality of indentations, such as U-shaped indentations. The plurality of indentations can comprise another shape. In some examples, an indentation can comprise a segment of a circle, oval and/or polygon. Each indentation can be positioned to be adjacent to a portion of the surgical pad 1202 which partially surrounds a respective edge opening 1216 in the surgical pad 1202 such that the portions 2612, 2614, 2616 of the spacer 2610 are positioned below portions of the surgical pad 1202 between immediately neighboring edge openings 1216 of the surgical pad 1202. The indentations can be configured to allow extension of surgical cords between the target tissue and the surgical pad 1202. For example, the indentations along the second edge portion 2626 can be configured to be positioned relative to the surgical pad 1202 such that the spacer 2610 partially surrounds any anchor cords extending between the target tissue and the surgical pad 1202. FIG. 26B shows two indentations along the second edge portion 2626. The two indentations can be configured to be oriented such that the spacer 2610 can partially surround two immediately neighboring edge openings 1216 of the surgical pad 1202. In some examples, the spacer 2610 can be configured to facilitate adjustment of tension in any surgical cords extending through the two edge openings 1216.

In some examples, a suture system can comprise a plurality of spacers 2610. For example, each of a plurality of spacers 2610 can be positioned below different portions of the surgical pad 1202 to partially surround different edge openings 1216 so as to facilitate adjustment in the tensioning of anchor cords extending through the different edge openings 1216. In some examples, the plurality of spacers 2610 can be stacked under the same portion of the surgical pad 1202, for example sharing at least one vertical plane.

In some examples, a spacer configured to be used in combination with the surgical pad 1202 can comprise more or fewer indentations. In some examples, the spacer can be configured to partially surround each edge opening 1216 of the surgical pad 1202. For example, the spacer can comprise, along a second edge portion, an indentation configured to be positioned relative to the surgical pad 1202 so as to partially surround each edge opening 1216. The spacer can comprise a corresponding portion configured to be positioned below a portion of the surgical pad 1202 between each pair of adjacent edge openings 1216. In some examples, the spacer can be configured to be positioned relative to the surgical pad 1202 so as to partially surround one edge opening 1216. For example, the spacer can comprise, along a second edge portion, an indentation configured to be positioned relative to the surgical pad 1202 so as to partially surround one edge opening 1216, and a corresponding portion configured to be positioned below portions of the surgical pad 1202 between the edge opening 1216 and an adjacent edge opening 1216 on each of two sides of the opening 1216.

In some examples, the spacer 2610 can have a uniform or substantially uniform thickness. The thickness can be a dimension extending between opposing portions of the first surface 2628 and the second surface 2630, such as a dimension perpendicular or substantially perpendicular to the first surface 2628 and/or the second surface 2630. In some examples, the spacer 2610 can comprise a non-uniform thickness.

In some examples, the spacer 2610 can be used in combination with the surgical pad 1602 described with reference to FIG. 16. In some examples, the spacer 2610 can be used in combination with the surgical pad 1702 described with reference to FIG. 17.

FIGS. 27A and 27B show an example of a suture system 2700 comprising the surgical pad 1602 described with reference to FIG. 16, and a spacer 2710 configured to be positioned between the surgical pad 1602 and a target tissue. FIG. 27A shows that the spacer 2710 can comprise a respective protrusion configured to be positioned on each of two opposing sides of an edge opening 1616. As described herein, the surgical pad 1602 can comprise a central opening 1614 at a center portion 1608 and a plurality of edge openings 1616 distributed around an outer edge portion 1610 of the surgical pad 1602. The plurality of edge openings 1616 can open to the outer edge 1612 of the surgical pad 1602. A plurality of surgical cords can extend through the plurality of edge openings 1616. In some examples, the surgical cords can comprise the anchor cords as described herein. A corresponding anchor cord or pair of anchor cords can extend through each of the plurality of edge openings 1616. A portion of a respective anchor cord or pair of anchor cords can comprise a portion extending externally of the target tissue and extending through an edge opening 1616. The plurality of anchor cords can be tensioned and secured to reduce the size of the opening and/or seal the opening in the target tissue. Note that the anchor cords are not shown in FIG. 27A for simplicity.

FIG. 27B shows the spacer 2710 in further detail. Referring to FIG. 27B, the spacer 2710 can have a first surface 2724 and a second surface 2726. The first surface 2724 can be a bottom surface configured to be oriented toward, including adjacent to and in contact with, the target tissue. The second surface 2726 can comprise an opposing orientation relative to the first surface 2724. For example, the second surface 2726 can be a top surface configured to be oriented toward, including adjacent to and in contact with, the surgical pad 1602.

The spacer 2710 can comprise a first protrusion 2712 and a second protrusion 2714 spaced apart from the first protrusion 2714. An intermediate portion 2716 can extend between the first protrusion 2712 and the second protrusion 2714. Space between the first and second protrusion 2712, 2714 can be configured to allow extension of the surgical cords between the target tissue and the surgical pad 1602. In some examples, the first protrusion 2712 and the second protrusion 2714 can be oriented toward one another and extend from the same side of the intermediate portion 2716. In some examples, the intermediate portion 2716 can comprise a curved configuration. The shape of the first and second protrusions 2712, 2714 and/or the curvature of the intermediate portion 2716 can facilitate placement of the spacer 2710 under the surgical pad 1602. For example, a curvature of the intermediate portion 2716 and/or the size and/or shape of the first and second protrusions 2712, 2714 can be predetermined to facilitate positioning of the spacer 2710 between the surgical pad 1602 and the target tissue, while avoiding or reducing interference with any surgical cords extending between the target tissue and the surgical pad 1602.

The spacer 2710 can comprise an outer edge 2718 including a first edge portion 2720 comprising a curvature. In some examples, the curved edge portion can comprise a curvature the same as or similar to that of the curvature of the outer edge 1612. The curvature of the curved edge portion can depend on a curvature of the outer edge 1612 of the surgical pad 1602. For example, the outer edge 1612 can comprise a circular or substantially circular shape and the curvature of the curved edge portion can comprise a segment of a circular or substantially circular shape. The curved edge portion of the first edge portion 2720 can be configured to be oriented the same as or similar to the outer edge 1612 of the surgical pad 1602, such as while the spacer 2710 is in the desired position between the target tissue and surgical pad 1602. In some examples, the curved portion of the first edge portion 2720 can be configured to be aligned with the outer edge 1612 of the surgical pad 1602 while the spacer 2710 is in the desired position.

The outer edge 2718 can comprise a second edge portion 2722 which includes an indentation, such as a U-shaped indentation. The indentation can comprise another shape. In some examples, an indentation can comprise a segment of a circle, oval and/or polygon. In some examples, the second edge portion 2722 can comprise a curved edge portion. The second curved edge portion can have the same or similar orientation as the first curved edge portion. The indentation can be configured to allow extension of one or more surgical cords between the target tissue and the surgical pad 1602. The indentation along the second edge portion 2722 can be positioned to partially surround the one or more surgical cords such that portions of the spacer 2710 are positioned between immediately neighboring edge openings 1616 of the surgical pad 1602. The indentation can be positioned to be adjacent to a portion of the surgical pad 1602 to partially surround a respective edge opening 1616. The intermediate portion 2716 can be positioned to be below a portion of an edge opening 1616, overlapping with only a portion of the edge opening 1616 such that the one or more surgical cords can extend between the target tissue and the surgical pad 1602.

In some examples, a suture system can comprise a plurality of the spacers 2710. For example, each of a plurality of spacers 2710 can be positioned below different portions of the surgical pad 1202 to partially surround a respective edge opening 1216 so as to facilitate adjustment in the tensioning of anchor cords extending through the different edge openings 1216. For example, the plurality of spacer 2710 can be laterally spaced from one another. In some examples, a spacer 2710 can be placed below a portion of each edge opening 1616.

In some examples, the spacer 2710 can have a uniform or substantially uniform thickness. The thickness can be a dimension extending between opposing portions of the first surface 2724 and the second surface 2726, such as a dimension perpendicular or substantially perpendicular to the first surface 2724 and/or the second surface 2726. In some examples, the spacer 2710 can comprise a non-uniform thickness.

In some examples, the spacer 2710 can be used in combination with the surgical pad 1202 described with reference to FIGS. 12-15. In some examples, the spacer 2710 can be used in combination with the surgical pad 1702 described with reference to FIG. 17.

As described herein, in some examples, a spacer can be configured to be positioned between a surface of a surgical pad oriented away from a target issue and a portion of one or more surgical cords positioned over the surface of the surgical pad oriented away from the target tissue. FIG. 28 shows an example of a suture system 2800 comprising a surgical pad 2840, a first surgical cord 2870 and a second surgical cord 2880, and a spacer 2810. The first and second surgical cords 2870, 2880 can comprise respective portions 2872, 2882 configured to be positioned over a surface of the surgical pad 2840 oriented away from the target tissue. The spacer 2810 can be configured to be positioned between the respective surgical cord portions 2872, 2882 and the surface of the surgical pad 2840 oriented away from the target tissue. In some examples, the surgical cords 2870, 2880 can comprise anchor cords as described herein. In some examples, the surgical cords 2870, 2880 can comprise tethers as described herein.

Referring to FIG. 28, the surgical pad 2840 can be configured to be positioned over the target tissue such that a first surface 2842, for example, a bottom surface, is oriented toward the target tissue and a second surface 2844, for example a top surface, can be oriented away from the target tissue. The spacer 2810 can be configured to be positioned over the second surface 2844, such as adjacent to and in contact with the second surface 2844. The spacer 2810 can be between the second surface 2844, including adjacent to and in contact with the second surface 2844, and the respective portions 2872, 2882 of the surgical cords 2870, 2880 positioned over the second surface 2844.

The spacer 2810 can comprise a first surface 2816, such as a bottom surface, and a second surface 2818, such as a top surface. The first surface 2816 can be configured to be oriented toward the surgical pad 2840, such as adjacent to and in contact with the second surface 2844 of the surgical pad 2840. The second surface 2818 can be configured to be oriented away from the surgical pad 2840. The second surface 2818 can be positioned to be adjacent to and in contact with the respective portions 2872, 2882 of the surgical cords 2870, 2880.

The surgical pad 2840 can have a plurality of openings, for example, a first opening 2846 and a second opening 2848 extending therethrough from the first surface 2842 to the second surface 2844. The first surgical cord 2870 and the second surgical cord 2880 can extend from within the target tissue, and through the first opening 2846 and second opening 2848, respectively, from the first surface 2842 to the second surface 2844 of the surgical pad 2840. The first surgical cord 2870 and the second surgical cord 2880 can form a pair of surgical cords. The respective portions 2872, 2882 of the first surgical cord 2870 and 2880 can be positioned over the surgical pad 2840 and coupled to one another over the second surface 2844. In some examples, the respective portions 2872, 2882 can be intertwined together to form a knot 2890 over the second surface 2844 of the surgical pad 2840.

The spacer 2810 can be configured to be positioned between the second surface 2844 of the surgical pad 2840 and the respective portions 2872, 2882 of the surgical cords 2870, 2880. For example, the spacer 2810 can be positioned at least partially between portions of the surgical cords 2870, 2880 intertwined together, such as the knot 2890, and the second surface 2844 of the surgical pad 2840. The spacer 2810 can provide a separation between the surgical pad 2840 and the respective portions 2872, 2882 of the surgical cords 2870, 2880, including the knot 2890. Providing the added separation between the surgical pad 2840 and the respective portions 2872, 2882 can provide added tension to the first surgical cord 2870 and the second surgical cord 2880. Inserting the spacer 2810 between the surgical pad 2840 and the respective portions 2872, 2882 can position the respective portions 2872, 2882, including the knot 2890 further away from the surgical pad 2840, and thereby adding to the tension exerted upon the surgical cords 2870, 2880.

In some examples, the spacer 2810 can comprise an elongate configuration. In some examples, the spacer 2810 can comprise a thickness which varies along a longitudinal axis. For example, the spacer 2810 can comprise a first end 2812 and a second end 2814. A thickness of the spacer 2810 can increase from the first end 2812 to the second end 2814. The thickness can be a dimension extending between opposing portions of the first and second surfaces 2816, 2818 of the spacer 2810, such as being perpendicular or substantially perpendicular to the first surface 2816 and/or the second surface 2818. The thickness can comprise a dimension perpendicular or substantially perpendicular to the longitudinal axis. In some examples, the spacer 2810 can have a uniform or substantially uniform width. The spacer 2810 can comprise a first and a second lateral surface 2820, 2822. The width can be a dimension extending between opposing portions of the lateral surfaces 2820, 2822. In some examples, the first and second lateral surfaces 2820, 2822 can be parallel or substantially parallel to one another. The width can be a dimension perpendicular or substantially perpendicular to the longitudinal axis and the thickness of the spacer 2810. In some examples, the spacer 2810 can comprise a wedge configuration.

In some examples, the first end 2812 of the spacer 2810 can be inserted first between the respective portions 2882, 2872 of the first and second surgical cords 2870, 2880. The spacer 2810 can be advanced relative to the respective portions 2872, 2882 until a desired tension for the surgical cords 2870, 2880 is achieved. For example, a portion of the spacer 2810 having a thickness configured to provide the desired tension for the surgical cords 2870, 2880 can be positioned between the portions 2882, 2872 of the first and second surgical cords 2870, 2880.

It will be understood that a spacer configured to be positioned between the surgical pad and respective portions of the surgical cords can have a variety of configurations. In some examples, the spacer can have a uniform thickness. In some examples, more than one spacer can be positioned between the surgical pad and respective portions of the surgical cords positioned over the surgical pad. In some examples, the plurality of spacers can be stacked, for example sharing at least one vertical plane.

FIG. 29 shows a process flow diagram for an example of a procedure 2900 for adjusting tension in surgical cords secured to a surgical pad. In block 2902, the procedure 2900 can comprise positioning the surgical pad over a target tissue. A first surface of the surgical pad can be configured to be oriented toward the target tissue and a second surface of the surgical pad can be configured to be oriented away from the target tissue. In block 2904, the procedure 2900 can comprise providing a first surgical cord and a second surgical cord, each of the first and second surgical cords comprising a first portion extending externally of the target tissue and a second portion embedded within the target tissue. As described herein, in some examples, the first surgical cord and second surgical cord can comprise a first and second tether. In some examples, the first surgical cord and second surgical cord can comprise a first and second anchor cord.

In block 2906, the procedure 2900 can comprise extending the first portion of the first surgical cord through the surgical pad from the first surface to the second surface and extending the first portion of the second surgical cord through the surgical pad from the first surface to the second surface. In block 2908, the procedure 2900 can comprise securing the first surgical cord and the second surgical cord to the surgical pad. In block 2910, the procedure 2900 can comprise positioning a spacer between the target tissue and the surgical pad. The spacer can provide a corresponding separation between the target tissue and the surgical pad and tension to the first and second surgical cords secured to the surgical pad.

In some examples, the surgical pad can be the surgical pad 200 described with reference to FIG. 2. For example, the surgical pad can be positioned over an opening in the target tissue. The first surgical cord and the second surgical cord can comprise a first tether and a second tether, respectively, as described herein. In some examples, a third tether and a fourth tether, and a fifth tether and a sixth tether can be provided. Each of the third and fourth tethers, and the fifth and sixth tethers can comprise a respective first portion configured to extend from the opening and a second portion configured to be embedded within the target tissue. The third tether and the fourth tether can be extended through the surgical pad from the first surface to the second surface at a respective third location and fourth location on the surgical pad. The fifth tether and the sixth tether can be extended through the surgical pad from the first surface to the second surface at a respective fifth and sixth location on the surgical pad. The third and fourth tethers can be secured to the surgical pad. The fifth and sixth tethers can be secured to the surgical pad.

In some examples, the first and second locations can be laterally spaced from one another along a first lateral dimension and form a first pair of locations. The third and fourth locations can be laterally spaced from one another along a second lateral dimension and form a second pair of locations. The fifth and sixth locations can be laterally spaced from one another along a third lateral dimension and form a third pair of locations. The first, second and third lateral dimensions can be parallel or substantially parallel to one another. In some examples, the first, third and fifth locations can be aligned with one another along a first longitudinal dimension perpendicular or substantially perpendicular to the first, second and third lateral dimensions. In some examples, the second, fourth and sixth locations are aligned with one another along a second longitudinal dimension parallel or substantially parallel with the first longitudinal dimension and perpendicular or substantially perpendicular to the first, second and third lateral dimensions.

As described herein, the spacer can comprise a first protrusion laterally spaced from a second protrusion, an intermediate portion extending perpendicularly or substantially perpendicularly between the first and second protrusions, and the first and second protrusions extending from a same side of the intermediate portion. Positioning the spacer between the target tissue and the surgical pad can comprise positioning the first protrusion adjacent to and in contact with a first portion of the first surface of the surgical pad on a first side of the first location. The second protrusion can be positioned adjacent to and in contact with a second portion of the first surface of the surgical pad to a second side of the second location oriented away from the first side. The first protrusion and second protrusion can comprise an orientation parallel or substantially parallel to the first, second and third longitudinal dimensions. In some examples, positioning the spacer between the target tissue and the surgical pad can comprise positioning the first protrusion adjacent to and in contact with a first portion of the first surface of the surgical pad on a first side of the first and second locations. Positioning the second protrusion adjacent to and in contact with a second portion of the first surface of the surgical pad to a second side of the first and second locations oriented away from the first side.

As described herein, the spacer can comprise a first protrusion laterally spaced from a second protrusion, a third protrusion laterally spaced from the second protrusion, a first intermediate portion extending perpendicularly or substantially perpendicularly between the first and second protrusions and a second intermediate portion extending perpendicularly or substantially perpendicularly between the second and third protrusions. The first, second and third protrusions can extend from a same side of the first and second intermediate portions. In some examples, positioning a spacer between the target tissue and the surgical pad can comprise positioning the first protrusion adjacent to and in contact with a first portion of the first surface of the surgical pad on a first side of the first pair of locations. The second protrusion can be positioned adjacent to and in contact with a second portion of the first surface of the surgical pad on a second side of the first pair of locations and between the first pair of locations and the second pair of locations. The third protrusion can be positioned adjacent to and in contact with a third portion of the first surface of the surgical pad to a second side of the second pair of locations oriented away from the second side of the first pair of locations. In some examples, the first protrusion, second protrusion, and third protrusion can comprise an orientation parallel or substantially parallel to the first, second and third lateral dimensions.

In some examples, the first and second locations on the surgical pad are a first pair of locations. The third and fourth locations can be a second pair of locations. The fifth and sixth locations can be a third pair of location. The first pair of locations, second pair of locations, and third pair of locations can be at respective positions along a curved path. In some examples, the spacer can comprise a first protrusion laterally spaced from a second protrusion and an intermediate portion comprising a curved configuration and extending between the first and second protrusions. The first and second protrusions can extend from a same side of the intermediate portion and be oriented toward one another. Positioning the spacer between the target tissue and the surgical pad can comprise positioning the first protrusion adjacent to and in contact with a first portion of the first surface of the surgical pad to a first side of the second pair of locations between the first pair of locations and the second pair of locations. The second protrusion can be positioned adjacent to and in contact with a second portion of the first surface of the surgical pad to a second side of the second pair of locations between the third pair of locations and the second pair of locations. In some examples, positioning the spacer between the target tissue and the surgical pad can comprise positioning the spacer adjacent to and in contact with a first portion of the first surface of the surgical pad between the first pair of locations and the second pair of locations or adjacent to and in contact with a second portion of the first surface of the surgical pad between the second pair of locations and the third pair of locations.

As described herein, a surgical pad, such as the surgical pad 900 described with reference to FIG. 9, can comprise a plurality of elongate ribs over a second surface of a flexible pad portion of the surgical pad. For example, the surgical pad can comprise a first elongate rib, a second elongate rib and a third elongate rib over the second surface, where each of the elongate ribs comprises a lumen extending therethrough. A first tether and second tether can be extended through a lumen of the first elongate rib from an outer edge distal end to a center portion distal end. A third tether and fourth tether can be extended through a lumen of a second elongate rib from an outer edge distal end to a center portion distal end. The fifth tether and sixth tether can be extended through a lumen of the third elongate rib from an outer edge distal end to a center portion distal end. The first, second, third, fourth, fifth and sixth tethers can be secured to one another over the center portion of the second surface. In some examples, positioning the spacer between the target tissue and the surgical pad can comprise positioning the spacer adjacent to and in contact with a center portion of the first surface of the surgical pad.

In some examples, the surgical pad can comprise a surgical pad described with reference to FIGS. 12-17. For example, positioning the surgical pad over the target tissue can comprise positioning the surgical pad over a portion of the target tissue surrounding an opening in the target tissue and aligning a central opening of the surgical pad with the opening. The first surgical cord and the second surgical cord can comprise a first anchor cord and a second anchor cord, respectively. For example, the first portion of the first anchor cord and the first portion of the second anchor cord can be configured to extend from within the target tissue from a respective position adjacent to the opening in the target tissue.

In some examples, the suture system can comprise a third anchor cord and a fourth anchor cord, and a fifth anchor cord and a sixth anchor cord. Each of the third and fourth anchor cords, and the fifth and sixth anchor cords can comprise a respective first portion extending from a respective position adjacent to the opening in the target tissue and a respective second portion embedded within the target tissue. The third anchor cord and the fourth anchor cord can be extended through the surgical pad from the first surface to the second surface at a second location on the surgical pad. The fifth anchor cord and the sixth anchor cord can be extended through the surgical pad from the first surface to the second surface at a third location on the surgical pad. The third and fourth anchor cords can be secured to the surgical pad. The fifth and sixth anchor cords can be secured to the surgical pad. In some examples, the first location, second location, and third location are at respective positions along a curved path.

In some examples, the spacer comprises a first protrusion laterally spaced from a second protrusion, and an intermediate portion comprising a curved configuration and extending between the first and second protrusions. The first and second protrusions can extend from a same side of the intermediate portion and be oriented toward one another. Positioning the spacer between the target tissue and the surgical pad can comprises positioning the first protrusion adjacent to and in contact with a first portion of the first surface of the surgical pad to a first side of the second location between the first location and the second location. The second protrusion can be positioned adjacent to and in contact with a second portion of the first surface of the surgical pad to a second side of the second location between the third location and the second location.

In some examples, the spacer can be a wedge-shaped spacer. In some examples, the spacer can be positioned adjacent to and in contact with a first portion of the first surface of the surgical pad between the first location and the second location or adjacent to and in contact with a second portion of the first surface of the surgical pad between the second location and the third location.

FIG. 30 shows a process flow diagram for another example of a procedure 3000 for adjusting tension in surgical cords secured to a surgical pad. In block 3002, the procedure 3000 can comprise positioning a surgical pad over a target tissue. A first surface of the surgical pad can be configured to be oriented toward the target tissue and a second surface of the surgical pad can be configured to be oriented away from the target tissue. In block 3004, the procedure 3000 can comprise providing a first surgical cord and a second surgical cord, each of the first and second surgical cords comprising a first portion extending externally of the target tissue and a second portion embedded within the target tissue. In block 3006, the procedure 3000 can comprise extending the first portion of the first surgical cord through the surgical pad from the first surface to the second surface and extending the first portion of the second surgical cord through the surgical pad from the first surface to the second surface. In block 3008, the procedure 3000 can comprise securing the first surgical cord and the second surgical cord to one another over the second surface of the surgical pad. In block 3010, the procedure 3000 can comprise positioning a spacer between the second surface of the surgical pad and portions of the first and second surgical cords positioned over the second surface of the surgical pad. The spacer can provide a corresponding separation between the target tissue and the surgical pad and tension to the first and second surgical cords secured to the surgical pad.

In some examples, extending the first surgical cord through the surgical pad and extending the second surgical cord through the surgical pad comprises extending the first and second surgical cords through the surgical pad at a respective first and second location on the surgical pad, and where securing the first and second surgical cords comprises forming a knot over the second surface of the surgical pad using respective portions of the first and second surgical cords. In some examples, positioning the spacer between the second surface of the surgical pad and the portions of the first and second surgical cords positioned over the second surface of the surgical pad comprises positioning the spacer between the knot and the second surface of the surgical pad.

As described herein, in some examples, a plurality of the spacer can be positioned between the target tissue and the surgical pad. In some examples, the plurality of spacers can be stacked one over the other. For example, the plurality of the spacers to share a vertical plane, such as a plane perpendicular or substantially perpendicular to a surface of the target tissue over which the spacers are positioned. In some examples, at last one of the plurality of spacers can be laterally positioned relative to another of the plurality of spacers. For example, the plurality of spacers can be laterally spaced from one another over the target tissue. In some examples, each of the plurality of spacers can be positioned adjacent to and in contact with a respective portion of the first surface of the surgical pad. The plurality of spacers may or may not be identical to one another. In some examples, at least one of the plurality of spacers can comprise a feature different from that of another of the plurality of spacers.

One or more spacers as described herein can be affixed directly or indirectly to the surgical pad and/or the target tissue. Any number of means for securing the spacer to the target tissue and/or surgical pad can be applicable, including for example sutures, glue, and/or staples.

ADDITIONAL EXAMPLES

Depending on the example, certain acts, events, or functions of any of the processes or algorithms described herein can be performed in a different sequence, may be added, merged, or left out altogether. Thus, in certain examples, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain examples include, while other examples do not include, certain features, elements and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain examples require at least one of X, at least one of Y and at least one of Z to each be present.

It should be appreciated that in the above description of examples, various features are sometimes grouped together in a single example, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular example herein can be applied to or used with any other example(s). Further, no component, feature, step, or group of components, features, or steps are necessary or indispensable for each example. Thus, it is intended that the scope of the disclosure and claims below should not be limited by the particular examples described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example examples belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A surgical pad comprising:
a flexible pad portion configured to be positioned over an opening in a target tissue, the flexible pad portion comprising a first surface configured to be oriented toward the target tissue and a second surface configured to be oriented away from the target tissue;
a plurality of designated locations around an outer edge portion of the second surface, each of the plurality of designated locations being configured to couple to corresponding tethers extending from the opening in the target tissue; and
a plurality of elongate ribs associated with the second surface and coupled to the flexible pad portion, the plurality of elongate ribs being disconnected from each other and configured to provide mechanical reinforcement for the flexible pad portion to counter forces exerted upon the flexible pad portion by the corresponding tethers, each of the plurality of elongate ribs comprising a first end at a center portion of the second surface and a second end spaced from a nearest portion of an outer edge of the flexible pad portion, and the surgical pad being configured to assume a reduced profile state to provide the surgical pad in a folded state in which the first end of each of the plurality of elongate ribs are oriented in a first direction and the second end of each of the plurality of elongate ribs are oriented in a second opposing direction.

2. The surgical pad of claim 1, wherein the plurality of elongate ribs is arranged in a radially-extending pattern over the second surface.

3. The surgical pad of claim 1, wherein the plurality of elongate ribs is distributed evenly across the second surface.

4. The surgical pad of claim 1, wherein each of the plurality of elongate ribs is at least one of a solid rib, a linear rib, and a cylindrical rod.

5. The surgical pad of claim 1, wherein the plurality of elongate ribs is sutured to the flexible pad portion.

6. The surgical pad of claim 1, wherein the flexible pad portion comprises a plurality of fasteners extending from the second surface and corresponding portions of each of the plurality of elongate ribs are configured to be inserted between a respective fastener and the second surface to couple the plurality of elongate ribs to the flexible pad portion.

7. The surgical pad of claim 1, wherein the plurality of designated locations is evenly distributed around the outer edge portion of the second surface.

8. The surgical pad of claim 1, wherein the plurality of designated locations comprises a designated location between each respective second end of each of the plurality of elongate ribs and a corresponding nearest portion of the outer edge of the flexible pad portion.

9. The surgical pad of claim 1, wherein the plurality of designated locations is between the second ends of the plurality of elongate ribs.

10. The surgical pad of claim 1, wherein the flexible pad portion has a circular shape.

11. The surgical pad of claim 1, wherein the flexible pad portion comprises a non-biodegradable cross-linked tissue.

12. The surgical pad of claim 11, wherein the plurality of elongate ribs comprises a non-biodegradable material.

13. The surgical pad of claim 1, wherein the plurality of elongate ribs is arranged in a radial pattern and the surgical pad assumes an umbrella configuration in the reduced profile state.

14. A surgical pad comprising:
a flexible pad portion comprising a first surface and a second opposing surface and configured to be positioned over an opening in a target tissue, the flexible pad portion transformable from a folded configuration to an unfolded configuration; and
a plurality of elongate ribs configured to provide mechanical reinforcement for the flexible pad portion and associated with a surface of the flexible pad portion configured to be oriented away from the target tissue, the plurality of elongate ribs being disconnected from each other and each comprising a first end oriented toward a center portion of the surface and a second end oriented away from the center portion and spaced from a nearest portion of an outer edge of the flexible pad portion, the first end of each of the plurality of elongate ribs being configured to be oriented proximally and the second end of each of the plurality of elongate ribs being configured to be oriented distally with the flexible pad portion in the folded configuration.

15. The surgical pad of claim 14, wherein the flexible pad portion in the folded configuration comprises a fold along at least one of the plurality of elongate ribs.

16. The surgical pad of claim 14, wherein the plurality of elongate ribs is coupled to an outwardly facing surface of the flexible pad portion in the folded configuration.

17. The surgical pad of claim 14, wherein a center of the flexible pad portion in the folded configuration forms a point.

\* \* \* \* \*